(12) United States Patent
Galloway et al.

(10) Patent No.: US 8,603,996 B2
(45) Date of Patent: Dec. 10, 2013

(54) MODULAR APTAMER-REGULATED RIBOZYMES

(75) Inventors: Katie Galloway, Pasadena, CA (US); Christina D. Smolke, Pasadena, CA (US); Maung Nyan Win, San Gabriel, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/418,507

(22) Filed: Mar. 13, 2012

(65) Prior Publication Data

US 2012/0263691 A1  Oct. 18, 2012

Related U.S. Application Data

(62) Division of application No. 11/938,220, filed on Nov. 9, 2007, now Pat. No. 8,158,595.

(60) Provisional application No. 60/857,824, filed on Nov. 9, 2006, provisional application No. 60/875,774, filed on Dec. 19, 2006.

(51) Int. Cl.
| C12N 15/11 | (2006.01) |
| C07H 21/02 | (2006.01) |
| C12Q 1/68 | (2006.01) |
| C12P 19/34 | (2006.01) |
| C12P 21/06 | (2006.01) |

(52) U.S. Cl.
USPC .......... 514/44; 435/6.13; 435/6.19; 435/69.1; 435/91.31; 435/325; 536/24.5

(58) Field of Classification Search
None
See application file for complete search history.

(56) References Cited

U.S. PATENT DOCUMENTS

| 4,235,871 A | 11/1980 | Papahadjopoulos et al. |
| 4,426,330 A | 1/1984 | Sears |
| 4,501,728 A | 2/1985 | Geho et al. |
| 4,534,899 A | 8/1985 | Sears |
| 4,737,323 A | 4/1988 | Martin et al. |
| 4,837,028 A | 6/1989 | Allen |
| 4,897,355 A | 1/1990 | Eppstein et al. |
| 5,013,556 A | 5/1991 | Woodle et al. |
| 5,013,830 A | 5/1991 | Ohtsuka et al. |
| 5,093,246 A | 3/1992 | Cech et al. |
| 5,108,921 A | 4/1992 | Low et al. |
| 5,176,996 A | 1/1993 | Hogan et al. |
| 5,213,804 A | 5/1993 | Martin et al. |
| 5,214,135 A | 5/1993 | Srivastava et al. |
| 5,227,170 A | 7/1993 | Sullivan |
| 5,256,775 A | 10/1993 | Froehler |
| 5,264,221 A | 11/1993 | Tagawa et al. |
| 5,264,423 A | 11/1993 | Cohen et al. |
| 5,264,564 A | 11/1993 | Matteucci |
| 5,270,163 A | 12/1993 | Gold et al. |
| 5,276,019 A | 1/1994 | Cohen et al. |
| 5,354,844 A | 10/1994 | Beug et al. |
| 5,356,633 A | 10/1994 | Woodle et al. |
| 5,395,619 A | 3/1995 | Zalipsky et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,500,357 A | 3/1996 | Taira et al. |
| 5,512,295 A | 4/1996 | Kornberg et al. |
| 5,521,291 A | 5/1996 | Curiel et al. |
| 5,525,719 A | 6/1996 | Srivastava et al. |
| 5,527,528 A | 6/1996 | Allen et al. |
| 5,534,259 A | 7/1996 | Zalipsky et al. |
| 5,543,152 A | 8/1996 | Webb et al. |
| 5,543,158 A | 8/1996 | Gref et al. |
| 5,547,932 A | 8/1996 | Curiel et al. |
| 5,556,948 A | 9/1996 | Tagawa et al. |
| 5,580,575 A | 12/1996 | Unger et al. |
| 5,582,981 A | 12/1996 | Toole et al. |
| 5,583,020 A | 12/1996 | Sullivan |
| 5,591,721 A | 1/1997 | Agrawal et al. |
| 5,595,756 A | 1/1997 | Bally et al. |
| 5,736,392 A | 4/1998 | Hawley-Nelson et al. |
| 5,756,291 A | 5/1998 | Griffin et al. |

(Continued)

FOREIGN PATENT DOCUMENTS

| AU | 2004206255 A1 | 8/2004 |
| WO | WO-88/04300 A1 | 6/1988 |

(Continued)

OTHER PUBLICATIONS

Kertsberg (Nucl. Acids Res. 30(21):4599-4606, 2002).*
Sekella et al (RNA (2002), 8:1242-1252).*
Aagaard et al., "Engineering and optimization of the miR-1 06b cluster for ectopic expression of multiplexed anti-HIV RNAs," *Gene Ther.*, 15:1536-1549 (2008).
Aagard and Rossi, "RNAi Therapeutics: Principles, Prospects and Challenges," *Adv. Drug Deliv. Rev.*, 59(2-3):75-86 (2007).
Abbas-Terki et al., "Lentiviral-Mediated RNA interference," *Hum. Gene Ther*, 13: 2197-2201 (2002).
Agrawal et al., "RNA interference: biology, mechanism, and applications," *Microbiology and Molecular Biology Reviews*, 67:657-685 (2003).

(Continued)

*Primary Examiner* — Richard Schnizer
(74) *Attorney, Agent, or Firm* — McCarter & English, LLP; Elizabeth A. Hanley; Yu Lu

(57) ABSTRACT

An extensible RNA-based framework for engineering ligand-controlled gene regulatory systems, called ribozyme switches, that exhibit tunable regulation, design modularity, and target specificity is provided. These switch platforms typically contain a sensor domain, comprised of an aptamer sequence, and an actuator domain, comprised of a hammerhead ribozyme sequence. A variety of modes of standardized information transmission between these domains can be employed, and this application demonstrates a mechanism that allows for the reliable and modular assembly of functioning synthetic hammerhead ribozyme switches and regulation of ribozyme activity in response to various effectors. In some embodiments aptamer-regulated cis-acting hammerhead ribozymes are provided.

17 Claims, 47 Drawing Sheets

(56) References Cited

U.S. PATENT DOCUMENTS

| | | | |
|---|---|---|---|
| 5,767,099 | A | 6/1998 | Harris et al. |
| 5,777,153 | A | 7/1998 | Lin et al. |
| 5,780,053 | A | 7/1998 | Ashley et al. |
| 5,830,430 | A | 11/1998 | Unger et al. |
| 5,830,653 | A | 11/1998 | Froehler et al. |
| 5,851,548 | A | 12/1998 | Dattagupta et al. |
| 5,855,910 | A | 1/1999 | Ashley et al. |
| 6,458,559 | B1 | 10/2002 | Shi et al. |
| 6,706,474 | B1 | 3/2004 | Lu et al. |
| 2002/0106648 | A1 | 8/2002 | Lizardi et al. |
| 2002/0150996 | A1 | 10/2002 | Nilsen-Hamilton |
| 2002/0166132 | A1 | 11/2002 | Scherman et al. |
| 2003/0105051 | A1 | 6/2003 | McSwiggen |
| 2003/0124595 | A1 | 7/2003 | Lizardi |
| 2003/0157030 | A1 | 8/2003 | Davis et al. |
| 2004/0063654 | A1 | 4/2004 | Davis et al. |
| 2004/0072785 | A1 | 4/2004 | Wolff et al. |
| 2004/0086884 | A1 | 5/2004 | Beach et al. |
| 2004/0162235 | A1 | 8/2004 | Trubetskoy et al. |
| 2004/0204377 | A1 | 10/2004 | Rana |
| 2005/0003362 | A1 | 1/2005 | Krylov et al. |
| 2005/0026286 | A1 | 2/2005 | Chi et al. |
| 2005/0037496 | A1 | 2/2005 | Rozema et al. |
| 2005/0042227 | A1 | 2/2005 | Zankel et al. |
| 2005/0048647 | A1 | 3/2005 | Taira et al. |
| 2005/0064595 | A1 | 3/2005 | MacLachlan et al. |
| 2005/0176017 | A1* | 8/2005 | Breaker ............................ 435/6 |
| 2005/0256071 | A1 | 11/2005 | Davis |
| 2005/0265957 | A1 | 12/2005 | Monahan et al. |
| 2006/0008910 | A1 | 1/2006 | MacLachlan et al. |
| 2006/0088864 | A1 | 4/2006 | Smolke et al. |
| 2006/0105975 | A1 | 5/2006 | Pendergrast et al. |
| 2006/0121510 | A1 | 6/2006 | Breaker et al. |
| 2006/0172925 | A1 | 8/2006 | Gorenstein et al. |
| 2006/0178327 | A1 | 8/2006 | Yeung |
| 2006/0240093 | A1 | 10/2006 | MacLachlan et al. |
| 2007/0077571 | A1 | 4/2007 | Ellington et al. |
| 2007/0083947 | A1 | 4/2007 | Huang et al. |
| 2007/0231392 | A1 | 10/2007 | Wagner et al. |
| 2008/0038296 | A1 | 2/2008 | Brahmbhatt et al. |
| 2008/0107694 | A1 | 5/2008 | Trogden et al. |
| 2008/0112916 | A1 | 5/2008 | Wagner et al. |
| 2008/0152661 | A1 | 6/2008 | Rozema et al. |
| 2009/0082217 | A1 | 3/2009 | Smolke et al. |
| 2009/0098561 | A1 | 4/2009 | Smolke et al. |
| 2009/0143327 | A1 | 6/2009 | Smolke et al. |
| 2009/0234109 | A1 | 9/2009 | Han et al. |
| 2010/0226901 | A1 | 9/2010 | Smolke et al. |
| 2010/0255545 | A1 | 10/2010 | Smolke et al. |

FOREIGN PATENT DOCUMENTS

| | | | |
|---|---|---|---|
| WO | WO-88/09810 A1 | 12/1988 | |
| WO | WO-89/10134 A1 | 11/1989 | |
| WO | WO-90/11364 A1 | 10/1990 | |
| WO | WO-90/14074 A1 | 11/1990 | |
| WO | WO-91/16024 A1 | 10/1991 | |
| WO | WO-91/17424 A1 | 11/1991 | |
| WO | WO-92/03568 A1 | 3/1992 | |
| WO | WO-97/42317 A1 | 11/1997 | |
| WO | WO-98/13526 A1 | 4/1998 | |
| WO | WO-99/04800 A1 | 2/1999 | |
| WO | WO-99/27133 A1 | 6/1999 | |
| WO | WO-99/54506 A1 | 10/1999 | |
| WO | WO-00/20040 A1 | 4/2000 | |
| WO | WO-2004/033653 A2 | 4/2004 | |
| WO | WO-2004/048545 A2 | 6/2004 | |
| WO | WO-2004/065601 A2 | 8/2004 | |
| WO | WO-2005/001039 A2 | 1/2005 | |
| WO | WO-2005/111238 A2 | 11/2005 | |
| WO | WO-2006/086669 A2 | 8/2006 | |
| WO | WO-2007/089607 A2 | 8/2007 | |
| WO | WO-2008/036825 A2 | 3/2008 | |
| WO | WO-2008/058291 A2 | 5/2008 | |

OTHER PUBLICATIONS

Al-Douahji et al., The cyclin kinase inhibitor p21WAF1/C1P1 is required for glomerular hypertrophy in experimental diabetic nephropathy. 1999 Kidney Int 56:1691-1699.

Amarzguioui et al., "Tolerance for mutations and chemical modifications in a siRNA," *Nucleic Acid Research*, 31:589-595 (2003).

An et al., "Artificial control of gene expression in mammalian cells by modulating RNA interference through aptamer-small molecule interaction," *RNA*, 12:710-716 (2006).

Anderson et al., "Environmental signal integration by a modular AND gate," *Mol. Syst. Biol.*, 3:133 (2007).

Araki et al., "Allosteric regulation of a ribozyme activity through ligand-induced conformational change," *Nucleic Acids Res.*, 26(14): 3379-3384 (1998).

Baker et al., "Engineering life: building a Fab for biology," *Scientific American*, 294:44-51 (2006).

Banerjee et al., "Control of developmental timing by small temporal RNAs: a paradigm for RNA-mediated regulation of gene expression," *Bioessays*, 24:119-129 (2002).

Barrick et al., "New RNA motifs suggest an expanded scope for riboswitches in bacterial genetic control," *Proc. Natl. Acad. Sci. USA*, 101:6421-6426 (2004).

Bartel, "MicroRNAs: genomics, biogenesis, mechanism, and function," *Cell*, 116:281-297 (2004).

Bartlett and Davis, "Insights into the kinetics of siRNA-mediated gene silencing from live-cell and live-animal bioluminescent imaging," *Nucleic Acids Res.*, 34:322-333 (2006).

Basu et al., "Spatiotemporal control of gene expression with pulse-generating networks," *Proc. Natl. Acad. Sci. USA*, 101:6355-6360 (2004).

Batzer et al., "Enhanced evolutionary PCR using oligonucleotides with inosine at the 3'-terminus," *Nucleic Acids Res.*, 19:5081 (1991).

Bauer et al., "Engineered riboswitches as novel tools in molecular biology," *J. Biotechnology*, 124:4-11 (2006).

Bauer et al., "Prevention of interferon-stimulated gene expression using microRNA-designed hairpins," *Gene Ther.*, 16:142-147 (2009).

Baulcombe, "Diced defence," *Nature*, 409(6818):295-296 (2001).

Bayer et al., "Programmable ligand-controlled riboregulators of eukaryotic gene expression," *Nat. Biotechnol.*, 23(3): 337-343 (2005).

Bayer et al., "Synthetic control of a fitness tradeoff in yeast nitrogen metabolism," *J. Biol. Eng.* 3:1 (2009).

Been and Cech, "One binding site determines sequence specificity of Tetrahymena pre-rRNA self-splicing, trans-splicing, and RNA enzyme activity," *Cell*, 47:207-216 (1986).

Beisel et al., "Design principles for riboswitch function," *PLoS Comp. Biol.*, 5:e1000363 (2009).

Beisel et al., "Model-guided design of ligand-regulated RNAi for programmable control of gene expression," *Molecular Systems Biology*, 4:224 (2008).

Benenson et al., "An autonomous molecular computer for logical control of gene expression," *Nature*, 429:423-429 (2004).

Benenson, "Small hairpin RNA as a small molecule sensor," *Mol. Sys. Biol.*, 4:227 (2008).

Benoist et al., "In vivo sequence requirements of the SV40 early promotor region," *Nature*, 290:304-310 (1981).

Berens et al., "A Tetracycline-binding RNA Aptamer," *Bioorg. Med. Chem.*, 9:2549-2556 (2001).

Berens et al., "Synthetic riboregulators—an alternative means to control gene expression," *Gene Therapy and Molecular Biology* 9:417-422 (2005).

Berezovski et al., "Nonequilibrium Capillary Electrophoresis of Equilibrium Mixtures: A Universal Tool for Development of Aptamers," *J. Am. Chem. Soc.* 127:3165-3171 (2005).

Berge et al., "Pharmaceutical Salts," *J. of Pharm Sci.*, 66:1-19 (1977).

Biesecker et al, "Derivation of RNA aptamer inhibitors of human complement C5," *Immunopharmacology*, 42(1-3):219-230 (1999).

Birikh et al., "The structure, function and application of the hammerhead ribozyme," *Eur. J. BioChem.* 245:1-16 (1997).

Blind et al., "Cytoplasmic RNA modulators of an inside-out signal-transduction cascade," *Proc. Nat'l. Acad. Sci. USA*, 96:3606-3610 (1999).

(56) References Cited

OTHER PUBLICATIONS

Blount and Uhlenbeck, "The structure-function dilemma of the hammerhead ribozyme," *Annu. Rev. Biophys. Biomol. Struct.*, 34:415-440 (2005).
Boiziau et al., "Identification of Aptamers Against the DNA Template for In Vitro Transcription of the HIV-1 TAR Element," *Antisense Nucleic Acid Drug Dev.* 7(4):369-380 (1997).
Boiziau et al. "DNA Aptamers Selected Against the HIV-1 trans-Activation responsive RNA Element Form RNA-DNA Kissing Complexes," *J. Biol. Chem.*, 274(18):12730-12737 (1999).
Boudreau et al., "Artificial microRNAs as siRNA shuttles: improved safety as compared to shRNAs in vitro and in vivo," *Mol. Ther.* 17(1): 169-175 (2009).
Breaker, "Engineered allosteric ribozymes as biosensor components," *Curr. Opin. Biotechnol.*, 13:31-39 (2002).
Breaker, "Complex riboswitches," *Science*, 319:1795-1797 (2008).
Brennecke et al., "Towards a complete description of the microRNA complement of animal genomes," *Genome Biol.*, 4:228.1-228.3 (2003).
Brinster et al., "Regulation of metallothionein-thymidine kinase fusion plasmids injected into mouse eggs," *Nature*, 296:39-42 (1982).
Brockstedt et al., "In vitro evolution of RNA aptamers recognizing carcinogenic aromatic amines," *Biochem. Biophys. Res. Commun.*, 313(4):1004-1008 (2004).
Brown et al., "Endogenous microRNA can be broadly exploited to regulate transgene expression according to tissue, lineage and differentiation state," *Nat. Biotechnol.*, 25:1457-1467 (2007).
Brummelkamp et al., "A system for stable expression of short interfering RNAs in mammalian cells," *Science*, 296:550-553 (2002).
Bunka and Stockley, "Aptamers come of age—at last," *Nat. Rev. Microbiol.*, 4:588-596 (2006).
Burke and Greathouse, "Low-magnesium, trans-cleavage activity by type III, tertiary stabilized hammerhead ribozymes with stem 1 discontinuities," *BMC BioChem.*, 6:14 (2005).
Burke et al., "RNA aptamers to the adenosine moiety of S-adenosyl methionine: structural inferences from variations on a theme and the reproducibility of SELEX," *Nucleic Acids Res.*, 25(10): 2020-2024 (1997).
Buskirk et al., "Engineering a ligand-dependent RNA transcriptional activator," *Chem. Biol* 11:1157-1163 (2004).
Buskirk et al., "In Vivo Evolution of an RNA-Based Transcriptional Activator," *Chemistry and Biology*, 10:533-540 (2003).
Cai et al., "Human microRNAs are processed from capped, polyadenylated transcripts that can also function as mRNAs," *RNA* 10:1957-1966 (2004).
Calin et al., "MiR-15a and miR-16-1 cluster functions in human leukemia," *Proc. Natl. Acad. Sci. USA*, 105:5166-5171 (2008).
Canny et al., "Fast cleavage kinetics of a natural hammerhead ribozyme," *J. Am. Chem. Soc,.* 126(35):10848-10849 (2004).
Caplen et al., "Specific inhibition of gene expression by small double-stranded RNAs in invertebrate and vertebrate systems," *Proc. Natl. Acad. Sci. USA*, 98:9742-9747 (2001).
Caponigro et al., "A small segment of the MAT.alpha.1 transcript promotes mRNA decay in *Saccharomyces cerevisiae*: a stimulatory role for rare codons," *Mol. Cell Biol.*, 13(9):5141-5148 (1993).
Carmell et al., "RNase III enzymes and the initiation of gene silencing," *Nature Structural and Molecular Biology*, 11:214-218 (2004).
Chen et al., "Genetic control of mammalian T-cell proliferation with synthetic RNA regulatory systems," *Proc. Natl. Acad. Sci. USA*, 107:8531-8536 (2010).
Chen et al., "Synthesis of oligodeoxyribonucleotide N3' -> P5' phosphoramidates," *Nucleic Acids Res.*, 23:2661-2668 (1995).
Chiu and Rana, "RNAi in Human Cells: Basic Structural and Functional Features of Small Interfering RNA," *Mol. Cell*, 10: 549-561 (2002).
Chiu and Rana, "siRNA function in RNAi: A chemical modification analysis," *RNA*, 9:1034-1048 (2003).

Cox et al., "Automated selection of aptamers against protein targets translated in vitro: from gene to aptamer," *Nucleic Acids Res.*, 30:e108 (2002).
Cox et al., "Programming gene expression with combinatorial promoters," *Mol. Syst. Biol.*, 3:145 (2007).
Croft et al., "Is prokaryotic complexity limited by accelerated growth in regulatory overhead?" *Genome Biology*, 5:P2 (2003).
Culler et al., "Functional selection and systematic analysis of intronic splicing elements identifies active sequence motifs and associated splicing factors," *Nuc. Acids Res.*, 38: 5152-5165 (2010).
Dambach, "Potential adverse effects associated with inhibition of p38a/β MAP kinases," *Curr. Top. Med. Chem.* 5(10):929-939 (2005).
Daniels, "A tenascin-C aptamer identified by tumor cell SELEX: Systematic evolution of ligands by exponential enrichment," *Proc. Natl. Acad. Sci. USA*, (2003) 100(26): 15416-15421.
Danilova et al., "RNAKinetics: a web server that models secondary structure kinetics of an elongating RNA," *J. Bioinform. Comput. Biol.*, 4:589-596 (2006).
Davidson et al., "Synthetic RNA circuits," *Nature Chemical Biology* 3(1):23-28 (2007).
De La Pena et al., "Peripheral regions of natural hammerhead ribozymes greatly increase their self-cleavage activity," *Embo J.*, 22(20):5561-5570 (2003).
Deans et al., "A Tunable Genetic Switch Based on RNAi and Repressor Proteins for Regulating Gene Expression in Mammalian Cells," *Cell*, 130:363-372 (2007).
Desai et al., "Genetic screens and selections for small molecules based on a synthetic riboswitch that activates protein translation," *J. Am. Chem. Soc.*, 126:13247-13254 (2004).
Dirks et al., "Triggered amplification by hybridization chain reaction," *Proc. Natl. Acad. Sci. USA*, 101:15275-15278 (2004).
Drabovich et al., "Selection of Smart Aptamers by Equilibrium Capillary Electrophoresis of Eauilibrium Mixtures (ECEEM)," *J. Am. Chem. Soc.* 127:11224-11225 (2005).
Dragun et al., "ICAM-1 antisense oligodesoxynucleotides prevent reperfusion injury and enhance immediate graft function in renal transplantation," *Kidney Int.*, 54:590-602 (1998).
Dragun et al., "Inhibition of intercellular adhesion molecule-1 with antisense deoxynucleotides prolonos renal isograft survival in the rat," *Kidney Int.*, 54:2113-2122 (1998).
Duconge and Toulme, "In vitro selection identifies key determinants for loop-loop interactions: RNA aptamers selective for the TAR RNA element of HIV-1," *RNA*, 5: 1605-1614 (1999).
Dueber et al., "Engineering synthetic signaling proteins with ultrasensitive input-output control," *Nat. Biotechnol.*, 25:660-662 (2007).
Egholm et al., "PNA hybridizes to complementary oligonucleotides obeying the Watson-Crick hydrogen-bonding rules," *Nature*, 365:566-568 (1993).
Elbashir et al., "Duplexes of 21-nucleotide RNAs Mediate RNA interference in cultured mammalian cells," *Nature* 411:494-498 (2001).
Elion, "The Ste5p scaffold," *J. Cell Sci.*, 114(22):3967-3978 (2001).
Ellington et al., "In vitro selection of RNA molecules that bind specific ligands," *Nature*, 346:818-822 (1990).
Elowitz and Leibler, "A synthetic oscillatory network of transcriptional regulators," *Nature*, 403:335-338 (2000).
Endy, "Foundations for engineering biology," *Nature*, 438:449-453 (2005).
Eulberg et al., "Development of an automated in vitro selection protocol to obtain RNA-based aptamers: identification of a biostable substance P antagonist," *Nucleic Acids Res.*, 33(4): e45 (2005).
Famulok, "Bringing Picomolar Protein Detection Into Proximity," *Nature Biotechnology*, 20:448-449 (2002).
Famulok, "Oligonucleotide aptamers that recognize small molecules," *Curr. Opin. Struct. Biol.*, 9:324-329 (1999).
Fedor, et al., "The catalytic diversity of RNAs," *Natl. Rev. Mol. Cell. Biol.*, 6:399-412(2005).
Flinders et al., "Recognition of planar and nonplanar ligands in the malachite green-RNA aptamer complex," *ChemBioChem.*, 5(I):62-72 (2004).
Flotte, "Size does matter: overcoming the adeno-associated virus packaging limit," *Respir. Res.*, 1:16-18 (2000).

(56) References Cited

OTHER PUBLICATIONS

Fredriksson et al., "Protein Detection Using Proximity-Dependent DNA Ligation Assays," *Nature Biotechnology*, 20:473-477 (2002).
Friedman et al., "Most mammalian mRNAs are conserved targets of microRNAs," *Genome Res.*, 19:92-105 (2009).
Fukusaki et al., "DNA aptamers that bind to chitin," *Bioorg. Med. Chem. Lett.* 10(5):423-425 (2000).
Gardner et al., "Construction of a genetic toggle switch in *Escherichia coli*," *Nature* 403:339-342 (2000).
Gardner et al., "Inferring genetic networks and identifying compound mode of action via expression profiling," *Science* 301:102-105 (2003).
Gautier et al., "α-DNA. IV: α-anomeric and β-anomeric tetrathymidylates covalently linked to intercalating oxazolopyridocarbazole. Synthesis, physicochemical properties and poly (rA) Binding," *Nucleic Acids Res.*, 15:6625-6641 (1987).
Gebhardt, "RNA aptamers to s-adenosylhomocysteine: kinetic properties, divalent cation dependency, and comparison with anti-s-adenosylhomocysteine antibody," *Biochemistry*, 39(24):7255-7265 (2000).
Geiger et al., RNA aptamers that bind L-arginine with sub-micromolar dissociation constants and high enantioselectivity, *Nucleic Acids Res.*, 24(6):1029-1036 (1996).
Gil et al., "Induction of apoptosis by the dsRNA-dependent protein kinase (PKR): mechanism of action," *Apoptosis*, 5:107-114 (2000).
Gilbert et al., "RNA aptamers that specifically bind to a K Ras-derived farnesylated peptide," *Bioorg. Med. Chem.*, 5(6):1115-1122 (1997).
Good, "Diverse antisense mechanisms and applications," *Cell Mol Life Sci* 60:823-824 (2003).
Good, "Translation repression by antisense sequences," *Cell Mol Life Sci* 60:854-861 (2003).
Gopinath et al., "An efficient RNA aptamer against human influenza B virus hemagglutinin," *J. Biochem.* (Tokyo) 139(5):837-846 (2006).
Gossen and Bujard, "Tight control of gene expression in mammalian cells by tetracycline-responsive promoters," *Proc. Natl. Acad. Sci. USA* 89:5547-5551 (1992).
Gouda et al., "Free energy calculations for theophylline binding to an RNA aptamer: Comparison of MM-PBSA and thermodynamic integration methods," *Biopolymers* 68:16-34 (2003).
Grassi et al., "Cleavage of collagen RNA transcripts by hammerhead ribozymes in vitro is mutation-specific and shows competitive binding effects," *Nucleic Acids Res.*, 25(17):3451-3458 (1997).
Grate and Wilson, "Inducible regulation of the *S. cerevisiae* cell cycle mediated by an RNA aptamer-ligand complex," *Bioorg. Med. Chem.*, 9:2565-2570 (2001).
Gregory et al., "The Microprocessor complex mediates the genesis of microRNAs," *Nature*, 432:235-240 (2004).
Gregory et al., "Human RISC couples microRNA biogenesis and post transcriptional gene silencing," *Cell* 123:631-640 (2005).
Grieger and Samulski, "Packaging capacity of adeno-associated virus serotypes: impact of larger genomes on infectivity and postentry steps," *J. Virol.*, 79:9933-9944 (2005).
Griffiths-Jones et al., "miRBase: microRNA sequences, targets and gene nomenclature," *Nucleic Acids Res.*, 34:D140-144 (2006).
Griffiths-Jones, "The microRNA Registry," *Nucleic Acids Res.*, 32:D109-111 (2004).
Grimm et al., "Fatality in mice due to oversaturation of cellular microRNA/short hairpin RNA pathways," *Nature*, 441:537-541 (2006).
Grundy and Henkin, "From ribosome to riboswitch: control of gene expression in bacteria by RNA structural rearrangements," *Crit. Rev. BioChem. Mol. Biol.*, 41:329-338 (2006).
Guet et al., "Combinatorial synthesis of genetic networks," *Science* 296:1466-1470 (2002).
Guil et al., "The multifunctional RNA-binding protein hnRNP A1 is required for processing of miR-18a," *Nat. Struct. Mol. Biol.*, 14: 591-596 (2007).
Hall et al., "Computational selection of nucleic acid biosensors via a slip structure model," *Biosens. Bioelectron.*, 22:1939-1947 (2007).
Haller et al., "In vitro selection of a 7-methyl-guanosine binding RNA that inhibits translation of capped mRNA molecules," *Proc. Natl. Acad. Sci. USA*, 94:8521-8526 (1997).
Haller et al., "Antisense oligonucleotides for ICAM-1 attenuate reperfusion injury and renal failure in the rat," *Kidney Int.*, 50:473-480 (1996).
Hamada et al., "Effects on RNA Interference in Gene Expression (RNAi) in Cultured Mammalian Cells of Mismatches and the Introduction of Chemical Modifications at the 3'-Ends of siRNAs," *Antisense Nucleic Acid Drug Dev.* 12(5):301-309 (2002).
Hamm et al., "Anti-idiotype RNA selected with an anti-nuclear export signal antibody is actively transported in oocytes and inhibits Rev- and cap-dependent RNA export," *Proc. Natl. Acad. Sci. USA*, 94:12839-12844 (1997).
Hammann et al., "Dissection of the ion-induced folding of the hammerhead ribozyme using 19F NMR," *Proc. Natl. Acad. Sci. USA*, 98(10):5503-5508 (2001).
Hammond et al., "Argonaute2, a Link Between Genetic and Biochemical Analyses of RNAi," *Science*, 293(5532):1146-1150 (2001).
Han et al., "Molecular basis for the recognition of primary microRNAs by the Drosha-DGCR8 complex," *Cell*, 125: 887-901 (2006).
Han et al., "Posttranscriptional crossregulation between Drosha and DGCR8," *Cell*, 136: 75-84 (2009).
Han et al., "The Drosha-DGCR8 complex in primary microRNA processing," *Genes Dev.*, 18: 3016-3027 (2004).
Hanahan and Weinberg, "The Hallmarks of Cancer," *Cell*, 100(1):57-70 (2000).
Hanson et al., "Tetracycline-aptamer-Mediated translational regulation in yeast," *Mol. Microbiol.*, 49(6):1627-1637 (2003).
Harborth et al., "Sequence, Chemical, and Structural Variation of Small Interfering RNAs and Short Hairpin RNAs and the Effect on Mammalian Gene Silencing," *Antisense Nucleic Acid Drug Dev.*, 13(2): 83-105 (2003).
Haseloff et al., "Simple RNA enzymes with new and highly specific endoribonuclease activities," *Nature* 334:585-591 (1988).
Hawkins et al., "Production of benzylisoquinoline alkaloids in *Saccharomyces cerevisiae*," *Nat. Chem. Biol.*, 4:564-573 (2008).
Hawkins et al., "The regulatory roles of the galactose permease and kinase in the induction response of the GAL network in *Saccharomyces cerevisiae*," *J. Biol. Chem,*. 281:13485-13492 (2006).
Hebert et al., "Loss of microRNA cluster miR-29a-b-1 in sporadic Alzheimer's disease correlates with increased BACE1-13-secretase expression," *Proc. Natl. Acad. Sci. USA* 105:6415-6420 (2008).
Heidenreich et al., "RNase H-independent antisense activity of oligonucleotide N3' -> P5 ' phosphoramidates," *Nucleic Acids Res.*, 25:776-780 (1997).
Hermann et al., "Adaptive Recognition by Nucleic Acid Aptamers," *Science*, 287:820-825 (2000).
Hesselberth et al., "In Vitro Selection of RNA Molecules That Inhibit the Activity of Ricin A-chain," *J. Biol., Chem.*, 275(7): 4937-4942 (2000).
Hesselberth et al., "Simultaneous detection of diverse analytes with an aptazyme ligase array," *Anal. BioChem.*, 312:106-112 (2003).
Hicke et al., "Tenascin-C Aptamers Are Generated Using Tumor Cells and Purified Protein," *J. Biol. Chem.*, 276(52):48644-48654 (2001).
Hirao et al., "RNA Aptamers That Bind to and Inhibit the Ribosome-inactivating Protein, Pepocin," *J. Biol. Chem.*, 275(7): 4943-4948 (2000).
Hirschbein et al., "31P NMR spectroscopy in oligonucleotide research and development," *Antisense Nucleic Acid Drug Dev.*, 7:55-61 (1997).
Hoff et al., "Fluorescence detection of a protein-bound 2Fe2S cluster," *ChemBioChem.* 10:667-670 (2009).
Hoff et al., "In vivo fluorescent detection of Fe-S clusters coordinated by human GRX2," *Chem. Biol.*, 16:1299-1308 (2009).
Hooshangi et al., "Ultrasensitivity and noise propagation in a synthetic transcriptional cascade," *Proc. Natl. Acad. Sci. USA*, 102: 3581-3586 (2005).
Hornung et al., "In vitro selected RNA molecules that bind to elongation factor tu," *Biochemistry*, 37:7260-7267 (1998).

(56) References Cited

OTHER PUBLICATIONS

Huang and Ferrell, Ultrasensitivity in the mitogen-activated protein kinase cascade. 1996 *Proc. Natl. Acad. Sci. USA*, 93:10078-10083.
Huizenga et al., "A DNA Aptamer that Binds Adenosine and ATP," *Biochemistry*, 34(2):656-665 (1995).
Hutvagner et al., "Sequence-specific inhibition of small RNA function," *PLoS Biol.* 2:E98 (2004).
Hwang et al., "A Hexanucleotide Element Directs MicroRNA Nuclear Import," *Science*, 315:97-100 (2007).
Inoue et al., "Sequence-dependent hydrolysis of RNA using modified oligonucleotide splints and RNase H," *FEBS Lett.*, 215:327-330 (1987).
Inoue et al., "Synthesis and hybridization studies on two complementary nona(2'-O-methyl) ribonucleotides," *Nucleic Acids Res.*, 15:6131-6148 (1987).
International Search Report in International Application No. PCT/US07/84364 (Aug. 19, 2008).
Isaacs et al., "Engineered riboregulators enable post-transcriptional control of gene expression," *Nat. Biotechnol.*, 22(7):841-847 (2004).
Isaacs et al., "Plug and play with RNA," *Nat. Biotechnol.*, 23:306-307 (2005).
Isaacs et al., "RNA synthetic biology," *Nat. Biotechnol.*, 24(5):545-554 (2006).
Javaherian et al., "Selection of aptamers for a protein target in cell lysate and their application to protein purification," *Nucleic Acids Res.*, 37(8):e62 (2009).
Jenison et al., "High-Resolution Molecular Discrimination by RNA," Science 263:1425-1429 (1994).
Jeong et al., "In vitro selection of the RNA aptamer against the sialyl lewis x and its inhibition of the cell adhesion," *Biochem. Biophys. Res. Comm.*, 281(I):237-243 (2001).
Jhaveri et al., "In vitro selection of signaling aptamers," *Nat. Biotechnol.* 18:1293-1297 (2000).
Jose et al., "Cooperative binding of effectors by an allosteric ribozyme," *Nucleic Acids Res.*, 29:1631-1637 (2001).
Kato et al., "In vitro selection of DNA aptamers which bind to cholic acid," *Biochim. Biophys. Acta*, 1493(1-2):12-18 (2000).
Keasling, "From yeast to alkaloids," *Nat. Chem. Biol.*, 4:524-525 (2008).
Kedde et al., "RNA-binding protein Dnd1 inhibits microRNA access to target mRNA," *Cell*, 131: 1273-1286 (2007).
Kertsburg et al., "A versatile communication module for controlling RNA folding and catalysis," *Nucleic Acids Res.*, 30(21):4599-4606 (2002).
Ketting et al., "Dicer functions in RNA interference and in synthesis of small RNA involved in developmental timing in *C. elegans*," *Genes Dev.*, 15:2654-2659 (2001).
Khosla et al., "Metabolic engineering for drug discovery and development," *Nat. Rev. Drug Discov.*, 2:1019-1025 (2003).
Khvorova et al., "Sequence elements outside the hammerhead ribozyme catalytic core enable intracellular activity," *Nat. Struct. Biol.*, 10(9):708-712 (2003).
Kiga et al., "An RNA aptamer to the xanthine-guanine base with a distinctive mode of purine recognition," *Nucleic Acids Res.*, 26:1755-1760 (1998).
Kim et al., "An artificial riboswitch for controlling pre-mRNA splicing," *RNA*, 11:1667-1677 (2005).
Kim et al., "Synthetic dsRNA Dicer substrates enhance RNAi potency and efficacy," *Nature Biotech.* 23: 222-226 (2008).
Kim, "Small RNAs: classification, biogenesis, and function," *Mol. Cells*, 19:1-15 (2005).
Kimoto et al., "Anti-(Raf-1) RNA aptamers that inhibit Ras-induced Raf-1 activation," *Eur. J. Biochem.*, 269(2): 697-704 (2002).
Kimoto et al., "RNA aptamers that specifically bind to the Ras-binding domain of Raf-1," *FEBS Lett.*, 441(2): 322-326 (1998).
Kipshidze et al., "Local delivery of c-myc neutrally charged antisense oligonucleotides with transport catheter inhibits myointimal hyperplasia and positively affects vascular remodeling in the rabbit balloon injury model," *Catheter Cardiovasc. Interv.*, 54:247-256 (2001).

Kipshidze et al., "Intramural coronary delivery of advanced antisense oligonucleotides reduces neointimal formation in the porcine stent restenosis model," *J. Am Coll. Cardiol.*, 39:1686-1691 (2002).
Kobayashi et al., "Programmable cells: Interfacing natural and engineered gene networks," *Proc. Natl. Acad. Sci. USA* 101(22):8414-8419 (2004).
Koch, "The Metabolism of Methylpurines by *Escherichia coli*," *J. Biol. Chem.*, 219:181-188 (1956).
Koizumi et al., "Allosteric selection of ribozymes that respond to the second messengers cGMP and cAMP," *Nat. Struct. Biol.*, 6(11):1062-1071 (1999).
Koizumi et al., "Molecular recognition of cAMP by an RNA aptamer," *Biochemistry*, 39(30):8983-8992 (2000).
Kok et al., "Human TRBP and PACT directly interact with each other and associate with dicer to facilitate the production of small interfering RNA," *J. Biol. Chem.*, 282:17649-17657 (2007).
Kramer et al., "BioLogic gates enable logical transcription control in mammalian cells," *Biotechnol. Bioeng.*, 87:478-484 (2004).
Kramer et al., "Role for antisense RNA in regulating circadian clock function in *Neurospora crassa*," *Nature*, 421:948-952 (2003).
Kraus et al, "Cutting Edge: Novel RNA Ligands Able to Bind CD4 Antigen and Inhibit CD4+ T Lymphocyte Function," *J. Immunol.*, 160(II): 5209-5212 (1998).
Kutryk et al., "Local intracoronary administration of antisense oligonucleotide against c-myc for the prevention of in-stent restenosis: results of the randomized investigation by the Thoraxcenter of antisense DNA using local delivery and IVUS after coronary stenting (ITALICS) trial," *J. Am. Coll. Cardiol.*, 39:281-287 (2002).
Kuwabara et al., "Allosterically controllable maxizyme-mediated suppression of progression of leukemia in mice," *Biomacromolecules*, 2:1220-1228 (2001).
Kuwabara et al., "Allosterically controllable ribozymes with biosensor functions," *Curr. Opin. Chem. Biol.*, 4:669-677 (2000).
Kuwabara et al., "Allosterically controlled single-chained maxizymes with extremely high and specific activity," *Biomacromolecules*, 2:788-799 (2001).
Lavorana et al., "In search of antisense," *Trends BioChem. Sci.*, 29:88-94 (2004).
Lee et al., "In vitro and in vivo assays for the activity of Drosha complex," *Methods Enzymol.*, 427:89-106 (2007).
Lee et al., "MicroRNA maturation: stepwise processing and subcellular localization," *EMBO J.*, 21(17): 4663-4670 (2002).
Lee et al., "The nuclear RNase III Drosha initiates microRNA processing," *Nature*, 425:415-419 (2003).
Lee et al., "Aptamer database," *Nucleic Acids Res.*, 32:D95-100 (2004).
Lee et al., "The role of PACT in the RNA silencing pathway," *EMBO J.*, 25:522-532 (2006).
Legiewicz et al., "A More Complex Isoleucine Aptamer with a Cognate Triplet," *J. Biol. Chem.*, 280(20):19815-19822 (2005).
Lemaitre et al., "Specific antiviral activity of a poly(L-lysine)-conjugated oligodeoxyribonucleotide sequence complementary to vesicular stomatitis virus N protein mRNA initiation site," *Proc. Natl. Acad. Sci. USA*, 84:648-652 (1987).
Lescoute and Westhof, "Topology of three-way junctions in folded RNAs," *RNA*, 12:83-93 (2006).
Letsinger et al., "Cholesteryl-conjugated oligonucleotides: synthesis, properties, and activity as inhibitors of replication of human immunodeficiency virus in cell culture," *Proc. Natl. Acad. Sci. USA*, 86:6553-6556 (1989).
Levine et al., "Quantitative Characteristics of Gene Regulation by Small RNA," *PLoS Biol.*, 5(e229):1998-2010 (2007).
Li and Breaker, "Kinetics of RNA Degradation by Specific Base Catalysis of Transesterification Involving the 2'-Hydroxyl Group," *J. Am. Chem. Soc.*, 121: 5364-5372 (1999).
Lilley, The origins of RNA catalysis in ribozymes. 2003 Trends BioChem. Sci 28:495-501.
Liu, et al., "RNA aptamers specific for bovine thrombin," *J. Mol. Recog.*, 16(1):23-27 (2003).

(56) References Cited

OTHER PUBLICATIONS

Liu et al., "Soafenib blocks the RAF/MEK/ERK pathway, inhibits tumor angiogenesis, and induces tumor cell apoptosis in hepatocellular carcinoma model PLC/PRF/5," *Cancer Res.*, 66(24):11851-11858 (2006).
Long and Uhlenbeck, "Self-cleaving catalytic RNA," *Faseb J.*, 7(1):25-30 (1993).
Lorsch et al., "In vitro selection of RNA aptamers specific for cyanocobalamin," *Biochemistry*, 33(4):973-982 (1994).
Lozupone et al., "Selection of the simplest RNA that binds isoleucine," *RNA*, 9(II):1315-1322 (2003).
Lutz and Bujard, "Independent and tight regulation of transcriptional units in *Escherichia coli* via the LacR/O, the TetR/O and AraC/$I_1$-$I_2$ regulatory elements," *Nucleic Acids Res.*, 25(6):1203-1210 (1997).
Luzi et al., "New Trends in Affinity Sensing: Aptamers for Ligand Binding," *Trends in Analytical Chemistry*, 22:810-818 (2003).
Lynch et al., "A high-throughput screen for synthetic riboswitches reveals mechanistic insights their function," *Chem. Biol.*, 14:173-184 (2007).
MacRae et al., "Structural Basis for Double-Stranded RNA Processing by Dicer," *Science*, 311(5758):195-198 (2006).
Malphettes and Fussenegger, "Impact of RNA interference on gene networks," *Metab. Eng.*, 8:672-683 (2006).
Mandal and Breaker, "Gene regulation by riboswitches," *Natl. Rev. Mol. Cell Biol.*, 5:451-463 (2004).
Mandal et al., "A glycine-dependent riboswitch that uses cooperative binding to control gene expression," *Science*, 306:275-279 (2004).
Mandal et al., "Adenine riboswitches and gene activation by disruption of a transcription terminator," *Nat. Struct. Mol. Biol.*, 11:29-35 (2004).
Mandel et al., "Gene regulation by riboswitches," *Natl. Rev. Mol. Cell Biol.*, 5:451-463 (2004).
Mannironi et al., "In vitro selection of dopamine RNA ligands," *Biochemistry*, 36:9726-9734 (1997).
Marschall et al., "Inhibition of gene expression with ribozymes," *Cell Mol. Neurobiol.*, 14(5):523-538 (1994).
Martin et al., "Redesigning cells for the production of complex organic molecules," *ASM News*, 68:336-343 (2002).
Mateus et al., "Destabilized green fluorescent protein for monitoring dynamic changes in yeast gene expression with flow cytometry," *Yeast*, 16:1313-1323 (2000).
Mathews et al., "Incorporating chemical modification constraints into a dynamic programming algorithm for prediction of RNA secondary structure," *Proc. Natl. Acad. Sci. USA*, 101:7287-7292 (2004).
Mathews et al., "Prediction of RNA secondary structure by free energy minimization," *Curr. Opin. Struct. Biol.*,16:270-278 (2006).
Matranga et al., "Passenger-strand cleavage facilitates assembly of siRNA into Ag02—containing RNAi enzyme complexes," *Cell*, 123:607-620 (2005).
McBride et al., "Artificial miRNAs mitigate shRNA-mediated toxicity in the brain: Implications for the therapeutic development of RNAi," *Proc. Natl. Acad. Sci. USA*, 105: 5868 (2008).
McCaffrey et al., "RNA interference in adult mice," *Nature*, 418:38-39 (2002).
McCormick, "Signalling Networks that Cause Cancer," *Trends Cell Biol.*, 9(12):M53-M56 (1999).
McManus et al., "Gene silencing using micro-RNA designed hairpins," *RNA*, 8:842-850 (2002).
Meister, "Sequence-specific inhibition of microRNA- and siRNA-induced RNA silencing," *RNA* 10:544-550 (2004).
Mendonsa et al., "In Vitro Evolution of Functional DNA Using Capillary Electrophoresis," *J. Am. Chem. Soc.*, 126:20-21 (2004).
Mendonsa et al., "In Vitro Selection of Aptamers with Affinity for Neuropeptide Y Using D Capillary Electrophoresis," *J. Am. Chem. Soc.*, 127:9382-9383 (2005).
Mendonsa et al., "In Vitro Selection of High-Affinity DNA Ligands for Human IgE Using Capillary Electrophoresis," *Anal. Chem.*, 76:5387-5392 (2004).

Misono et al. "Selection of RNA aptamers against human influenza virus hemagglutinin using surface plasmon resonance," *Anal. Biochem.* 342(2):312-317 (2005).
Muller et al., "Thermodynamic characterization of an engineered tetracycline-binding riboswitch," *Nucleic Acids Res.*, 34(9): 2607-2617 (2006).
Nagai et al., "A variant of yellow fluorescent protein with fast and efficient maturation for cell-biological applications," *Nat. Biotechnol.*, 20:87-90 (2002).
Ng and Abelson, "Isolation and sequence of the gene for actin in *Saccharomyces cerevisiae*," *Proc. Natl. Acad. Sci. USA*, 77(7):3912-3916 (1980).
Nickols et al., "Suppression of androgen receptor-mediated gene expression by a sequence-specific DNA-binding polyamide," *Proc. Natl. Acad. Sci. USA*, 104:10418-10423 (2007).
Nishiwaki et al., "Structure of the yeast HIS5 gene responsive to general control of amino acid biosynthesis," *Mol. Gen. Genet.*, 208:159-167 (1987).
Novina, et al., "The RNAi revolution," *Nature*, 430(6996):161-164 (2004).
Nutiu et al., "Structure-Switching Signaling Aptamers," *J. Am. Chem. Soc.*, 125:4771-4778 (2003).
Nutiu et al., "Structure-Switching Signaling Aptamers: Transducing Molecular Recognition Into Fluorescence Signaling," *Chem. Eur. J.*, 10:1868-1876 (2004).
Ogawa and Maeda, "An artificial aptazyme-based riboswitch and its cascading system in *E. coli*," *ChemBioChem.*, 9:206-209 (2008).
Ogawa et al., "Purification, Characterization, and Gene Cloning of Purine Nucleosidase from *Ochrobactrum anthropi*," *Appl. Environ. Microbial.*, 67(1):1783-1787 (2001).
Ohrt et al., "Fluorescence correlation spectroscopy and fluorescence cross-correlation spectroscopy reveal the cytoplasmic origination of loaded nuclear RISC in vivo in human cells," *Nucleic Acids Res.*, 36(20): 6439-6449 (2008).
Ohtsuka et al., "An alternative approach to deoxyoligonucleotides as hybridization probes by insertion of deoxyinosine at ambiguous codon positions," *J. Biol. Chem.*, 260:2605-2608 (1985).
Osborne et al., "Nucleic Acid Selection and the Challenge of Combinatorial Chemistry," *Chem. Rev.*, 97:349-370 (1997).
Paddison et al., "Short hairpin RNAs (shRNAs) induce sequence-specific silencing in mammalian cells," *Genes Dev.*, 16:948-958 (2002).
Paddison et al., "Stable suppression of gene expression by RNAi in mammalian cells," *Proc. Natl. Acad. Sci. USA*, 99:1443-1448 (2002).
Pan et al., "A self-processing ribozyme cassette: utility against human papillomavirus 11 E6/E7 mRNA and hepatitis B virus," *Mol. Ther.*, 9(4):596-606 (2004).
Parisien et al., "The MC-Fold and MC-Sym pipeline infers RNA structure from sequence data," *Nature*, 452:51-55 (2008).
Park et al., "Rewiring MAP kinase pathways using alternative scaffold assembly mechanisms," *Science*, 299:1061-1064 (2003).
Pelletier and Sonenberg, "Insertion mutagenesis to increase secondary structure within the 5' noncoding region of a eukaryotic mRNA reduces translational efficiency," *Cell*, 40:515-526 (1985).
Penchovsky et al., "Computational design and experimental validation of oligonucleotide-sensing allosteric ribozymes," *Nat. Biotechnol.*, 23:1424-1433 (2005).
Penedo et al., "Folding of the natural hammerhead ribozyme is enhanced by interaction of auxiliary elements," *RNA*, 10(5):880-888 (2004).
Perry-O'Keefe et al., Peptide nucleic acid pre-gel hybridization: an alternative to Southern hybridization. 1996 *Proc. Natl. Acad. Sci. USA* 93:14670-14675.
Pfleger et al., "Combinatorial engineering of intergenic regions in operons tunes expression of multiple genes," *Nat. Biotech.* 24:1027-1032 (2006).
Piganeau et al., in vitro selection of allosteric ribozymes: theory and experimental validation. 2001 J Mol Biol 312:1177-1190.
Pley et al., "Three-dimensional structure of a hammerhead ribozyme," *Nature*, 372:68-74 (1994).
Qi and Elion, "MAP Kinase Pathways," *J. Cell Sci.*, 118(16):3569-3571 (2005).

(56) References Cited

OTHER PUBLICATIONS

Raab and Stephanopoulos, "Dynamics of gene silencing by RNA interference," *Biotechnol. Bioeng.*, 88:121-132 (2004).
Rand et al., "Argonaute2 cleaves the anti-guide strand of siRNA during RISC activation," *Cell*, 123:621-629 (2005).
Rinaudo et al., "A universal RNAi-based logic evaluator that operates in mammalian cells," *Nat. Biotechnol.*, 25:795-801 (2007).
Robertson et al., "Design and optimization of effector-activated ribozyme ligases," *Nucleic Acids Res.*, 28:1751-1759 (2000).
Robertson et al., "In vitro selection of an allosteric ribozyme that transduces analytes to amplicons," *Nat. Biotechnol.*, 17:62-66 (1999).
Rodionov et al., "Reconstruction of regulatory and metabolic pathways in metal-reducing δ-proteobacteria," *Genome Biol.*, 5:R90.1-R90.27 (2004).
Rossi, "Targeted cleavage: Tuneable cis-cleaving ribozymes," *Proc. Natl. Acad. Sci. USA*, 104(38):14881-14882 (2007).
Rossolini et al., "Use of deoxyinosine-containing primers vs degenerate primers for polymerase chain reaction based on ambiguous sequence information," *Mol. Cell Probes*, 8:91-98, (1994).
Roth et al., "Selection in vitro of allosteric ribozymes," *Methods Mol. Bio.*, 252:145-164 (2004).
Roychowdhury-Saha et al., "Flavin recognition by an RNA aptamer targeted toward FAD," *Biochemistry*, 41 (8):2492-2499 (2002).
Ruckman et al., "2'-Fluoropyrimidine RNA-based Aptamers to the 165-Amino Acid Form of Vascular Endothelial Growth Factor (VEGF165)," *J. Biol. Chem.*, 273(32): 20556-20567 (1998).
Rusconi et al., "Blocking the initiation of coagulation by RNA aptamers to factor VIIa," *Thromb. Haemost.*, 84(5):841-848 (2000).
Saksmerprome et al., "Artificial tertiary motifs stabilizing transcleaving hammerhead ribozymes under conditions of submillimolar divalent ions and high temperatures," *RNA*, 10(12)1 916-1924 (2004).
Salehi-Ashtiani and Szostak, "In vitro evolution suggests multiple origins for the hammerhead ribozyme," *Nature*, 414:82-84 (2001).
Samarsky et al., "A small nucleolar RNA:ribozyme hybrid cleaves a nucleolar RNA target in vivo with near-perfect efficiency," *Proc. Natl. Acad. Sci. USA*, 96:6609-6614 (1999).
Saran et al., "The tyranny of adenosine recognition among RNA aptamers to coenzyme A," *BMC Evol. Biol.*, 3(I):26 (2003).
Sarin et al., "Inhibition of acquired immunodeficiency syndrome virus by oligodeoxynucleoside methylphosphonates," *Proc. Natl. Acad. Sci. USA*, 85:7448-7451 (1988).
Sarver et al., "Ribozymes as potential anti-HIV-1 therapeutic agents," *Science*, 247:1222-1225 (1990).
Scherer et al., "Approaches for the sequence-specific knockdown of mRNA," *Nat. Biotechnol.* 21:1457-1465 (2003).
Scherer et al., "Recent applications of RNAi in mammalian systems," *Curr. Pharm. Biotechnol.*, 5:355-360 (2004).
Scherr et al., "Specific hammerhead ribozyme-mediated cleavage of mutant N-*ras* mRNA in vitro and ex vivo," *J. Biol. Chem.*, 272(22):14304-14313 (1997).
Schneider et al, "Selective enrichment of RNA species for tight binding to *Escherichia coli* rho factor," *FASEB J.* (1993) 7(I): 201-207.
Schwarz et. al., "Evidence that siRNAs Function as Guides, Not Primers, in the Drosophila and Human RNAi Pathways," *Mol. Cell*, 10: 537-548 (2002).
Seelig et al, "Enzyme-Free Nucleic Acid Logic Circuits," *Science*, 314: 1585-1588 (2006).
Shalgi et al., "Global and Local Architecture of the Mammalian microRNA-Transcription Factor Regulatory Network," *PLoS Comput. Biol.*, 3:e131 (2007).
Shapiro, "Discovering New MPA Kinase Inhibitors," *Chem. Biol.*, 13(8):807-809 (2006).
Shapiro et al., "RNA computing in a living cell," *Science*, 322:387-388 (2008).
Silverman, "Rube Goldberg Goes (RIBO)Nuclear? Molecular Switches and Sensors Made From RNA," *RNA*, 9:377-383 (2003).
Smolke et al., "Coordinated, differential expression of two genes through directed mRNA cleavage and stabilization by secondary structures," *Appl. Environ. Microbiol.*, 66:5399-5405 (2000).
Smolke et al., "Controlling the metabolic flux through the carotenoid pathway using directed mRNA processing and stabilization," *Met. Eng.*, 3:313-321 (2001).
Smolke et al., "Effects of transcription induction homogeneity and transcript stability on expression of two genes in a constructed operon," *Appl. Micro. Biotech.*, 57:689-696 (2001).
Smolke et al., "Effect of copy number and mRNA processing and stabilization on transcript and protein levels from an engineered dual-gene operon," *Biotech. Bioeng.*, 78:412-424 (2002).
Smolke et al., "Effect of gene location, mRNA secondary structures, and RNase sites on expression of two genes in an engineered operon," *Biotech. Bioeng.*, 80:762-776 (2002).
Smolke et al., "Molecular Switches for Cellular Sensors," *Engineering and Science*, 67(4):2837 (2005).
Smolke, "Building outside of the box: iGEM and the BioBricks Foundation," *Nat. Biotech.* 27:1099-2102 (2009).
Smolke, "Its the DNA that counts," *Science*, 324:1156-1157 (2009).
Sontheimer, "Assembly and Function of RNA Silencing Complexes," *Nat. Rev. Mol. Cell Biol.*, 6(2):127-138 (2005).
Soukup and Breaker, "Engineering precision RNA molecular switches," *Proc. Natl. Acad. Sci. USA*, 96:3584-3589 (1999).
Soukup and Breaker, "Relationship between internucleotide linkage geometry and the stability of RNA," *RNA*, 5:1308-1325 (1999).
Soukup et al., "Engineering precision RNA molecular switches," *Proc. Natl. Acad. Sci. USA*, 96:3584-3589 (1999).
Soukup et al., "Nucleic acid molecular switches," *TIBTECH*, 17: 469-476 (1999).
Soukup et al., "Design of allosteric hammerhead ribozymes activated by ligand-induced structure stabilization," *Structure* 7:783-791 (1999).
Soukup et al., "Altering molecular recognition of RNA aptamers by allosteric selection," *J. Mol. Biol.*, 298:623-632 (2000).
Soukup et al., "Generating new ligand-binding RNAs by affinity maturation and disintegration of allosteric ribozymes," *RNA*, 7:524-536 (2001).
Soukup and Soukup, "Riboswitches exert genetic control through metabolite-induced conformational change," *Current Opinions in Structural Biology*, 14:344 (2004).
Stein et al., "Oligodeoxynucleotides as inhibitors of gene expression: a review," *Cancer Res.*, 48:2659-2668 (1988).
Stein et al., "Physicochemical properties of phospborothioate oligodeoxynucleotides," *Nucleic Acids Res.*, 16:3209-3221 (1988).
Stern et al., "A system for Cre regulated RNA interference in vivo," *Proc. Natl. Acad. Sci. USA*, 105:13895-13900 (2008).
Stojanovic et al., "A deoxyribozyme-based molecular automaton," *Nat. Biotechnol.*, 21:1069-1074 (2003).
Stojanovic et al., "Modular aptameric sensors," *J. Am. Chem. Soc.*, 126:9266-9270 (2004).
Sudarsan et al., "Metabolite-binding RNA domains are present in the genes of eukaryotes," *RNA*, 9:644-647 (2003).
Sudarsan et al., "Tandem riboswitch architectures exhibit complex gene control functions," *Science*, 314(5797):300-304 (2006).
Suel et al., "Tunability and noise dependence in differentiation dynamics," *Science*, 315:1716-1719 (2007).
Suess et al., "Conditional gene expression by controlling translation with tetracycline-binding aptamers," *Nucleic Acids Res.*, 31:1853-1858 (2003).
Suess et al., "A theophylline responsive riboswitch based on helix slipping controls gene expression in vivo," *Nucleic Acids Res.*, 32(4):1610-1614 (2004).
Suess et al., "Engineered riboswitches: overview, problems and trends," *RNA Biol.*, 5(1):1-6 (2008).
Sui et al., "A DNA vector-based RNAi technology to suppress gene expression in mammalian cells," *Proc. Natl. Acad. Sci. USA* 99:5515-5520 (2002).
Sun et al., "Multi-miRNA hairpin method that improves gene knockdown efficiency and provides linked multi-gene knockdown," *Biotechniques*, 41:59-63 (2006).

(56) References Cited

OTHER PUBLICATIONS

Tahiri-Alaoui et al., "High affinity nucleic acid aptamers for streptavidin incorporated into bispecific capture ligands," *Nucleic Acids Res.*, 30(10): e45 (2002).
Taira et al., "Construction of a novel RNA-transcript-trimming plasmid which can be used both in vitro in place of run-off and (G)-free transcriptions and in vivo as multi-sequences transcription vectors," *Nucleic Acids Res.*, 19:5125-5130 (1991).
Takeno et al., "Selection of an RNA Molecule that Specifically Inhibits the Protease Activity of Subtilisin," *J. Biochem.*, 125(6):1115-1119 (1999).
Tang et al., "Rational design of allosteric ribozymes," *Chem. Biol.*, 4:453-459 (1997).
Tao et al., "Arginine-binding RNAs resembling tar identified by in vitro selection," *Biochemistry*, 35(7):2229-2238 (1996).
Thompson et al., "Group I aptazymes as genetic regulatory switches," *BMC Biotechnol.*, 2:21 (2002).
Tuerk et al., "RNA pseudoknots that inhibit human immunodeficiency virus type 1 reverse transcriptase," *Proc. Natl. Acad. Sci. USA*, 89:6988-6992 (1992).
Tuerk et al., "Systematic evolution of ligands by exponential enrichment: RNA ligands to bacteriophage T4 DNA polymerase," *Science*, 249:505-510 (1990).
Tuleuova et al., "Modulating endogenous gene expression of mammalian cells via RNA-small molecule interaction," *BioChem. Biophys. Res. Commun.*, 376:169-173 (2008).
U.S. Appl. No. 12/218,628, filed Mar. 26, 2009, Christina D. Smolke.
Ulrich et al., "In vitro selection of RNA molecules that displace cocaine from the membrane-bound nicotinic acetylcholine receptor," *Proc. Natl. Acad. Sci. USA*, 95(24): 1 4051-14056 (1998).
Urvil et al., "Selection of RNA aptamers that bind specifically to the NS3 protease of hepatitis C virus," *Eur. J. Biochem.*, 248(I):130-138 (1997).
Vacek et al., "Antisense-mediated redirection of mRNA splicing," *Cell Mol. Life Sci.*, 60:825-833 (2003).
Vaish et al., "A novel, modification-dependent ATP-binding aptamer selected from an RNA library incorporating a cationic functionality," *Biochemistry*, 42(29):8842-8851 (2003).
van der Krol et al., "Modulation of eukaryotic gene expression by complementary RNA or DNA sequences," *Biotechniques*, 6:958-976 (1988).
Ventura et al., "Targeted Deletion Reveals Essential and Overlapping Functions of the miR-17-92 Family of miRNA Clusters," *Cell.*, 132:875-886 (2008).
Villemaire et al., "Reprogramming Alternative Pre-messenger RNA Splicing through the Use of Protein-binding Antisense Oligonucleotides," *Biol. Chem.*, 278(50): 50031-50039 (2003).
Voigt, "Genetic parts to program bacteria," *Curr. Opin. Biotechnol.*, 17:548-557 (2006).
Vuyisich et al., "Controlling protein activity with ligand-regulated RNA aptamers," *Chemistry and Biology*, 9:907-913 (2002).
Wagner et al., "Nucleotide sequence of the thymidine kinase gene of herpes simplex virus type 1," *Proc. Natl. Acad. Sci. USA*. 78:1441-1445 (1981).
Wagner, "Gene inhibition using antisense oligodeoxynucleotides," *Nature*, 372:333-335 (1994).
Wallace et al., "In vitro selection and characterization of streptomycin-binding RNAs: Recognition discrimination between antibiotics," *RNA*, 4(I):112-123 (1998).
Wang et al., "RNA molecules that specifically and stoichiometrically bind aminoglycoside anitibiotics with high affinities," *Biochemistry*, 35(38):12338-12346 (1996).
Wang et al., "A general approach for the use of oligonucleotide effectors to regulate the catalysis of RNA-cleaving ribozymes and DNAzymes," *Nucleic Acids Res.*, 30:1735-1742 (2002).
Wang et al., "A general strategy for effector-mediated control of RNA-cleaving ribozymes and DNA enzymes," *J. Mol. Biol.*, 318:33-43 (2002).
Wang et al., "General and Specific Functions of Exonic Splicing Silencers in Splicing Control," *Molecular Cell*, 23:61-70 (2006).

Wang et al., "Recent patents on the identification and clinical application of microRNAs and target genes," *Recent Pat DNA Gene Seq.*, 1:116-124 (2007).
Wang et al., "MicroRNA-based therapeutics for cancer," *BioDrugs*, 23:15-23 (2009).
Watkins et al., "Metabolomics and biochemical profiling in drug discovery and development," *Curr. Opin. Mol. Ther.*, 4:224-228 (2002).
Weigand and Suess, "Tetracycline aptamer-controlled regulation of pre-mRNA splicing in yeast," *Nucleic Acids Res.*, 35:4179-4185 (2007).
Weigand et al., "Screening for engineered neomycin riboswitches that control translation initiation," *RNA*, 14:89-97 (2008).
Weinberg and Rossi, "Comparative single-turnover kinetic analyses of trans-cleaving hammerhead ribozymes with naturally derived non-conserved sequence motifs," *FEBS Lett* 579(7):1619-1624 (2005).
Weinberg et al., "Effective anti-hepatitis B virus hammerhead ribozymes derived from multimeric precursors," *Oligonucleotides*, 17(1):104-112 (2007).
Weiss et al., "Antisense RNA gene therapy for studying and modulating biological processes," *Cell Mol. Life Sci.*, 55:334-358 (1999).
Welz et al., "Ligand binding and gene control characteristics of tandem riboswitches in *Bacillus anthracis*," *RNA*, 13:573 (2007).
Werstuck et al., "Controlling gene expression in living cells through small molecule-RNA interactions," *Science*, 282:296-298 (1998).
Westerhout and Berkhout, "A systematic analysis of the effect of target RNA structure on RNA interference," *Nucleic Acids Res.*, 35(13):4322-4330 (2007).
Wieland and Hartig, "Improved aptazyme design and in vivo screening enable riboswitching in bacteria," *Angew. Chem. Int. Ed. Eng.*, 147:2604-2607 (2008).
Wieland et al., "Artificial riboswitches: synthetic mRNA-based regulators of gene expression," *ChemBioChem.*, 9:1873-1878 (2008).
Wieland et al., "Artificial ribozyme switches containing natural riboswitch aptamer domains," *Angew. Chem. Int. Ed. Eng.*, 148: 2715-2718 (2009).
Wilda et al., "Killing of leukemic cells with a BCRIABL fusion gene by RNA interference I (RNAi)," *Oncogene*, 21:5716-5724 (2002).
Wilson et al., "The interaction of intercalators and groove-binding agents with DNA triplehelical structures: the influence of ligand structure, DNA backbone modifications and sequence," *J. Mol. Recognit.*, 7:89-98 (1994).
Wilson et al., "Functional requirements for specific ligand recognition by a biotin-binding RNA pseudoknot," *Biochemistry*, 37:14410-14419 (1998).
Wilson et al., "In vitro selection of functional nucleic acids," *Annu. Rev. Biochem.*, 68:611-647 (1999).
Win et al., "Codeine-binding RNA aptamers and rapid determination of their binding constants using a direct coupling surface plasmon resonance assay," *Nuc. Acids Res.* 34:5670-5682 (2006).
Win et al., "RNA as a Versatile and Powerful Platform for Engineering Genetic Regulatory Tools," *Biotechnology and Genetic Engineering Reviews* 24:311-346 (2007).
Win et al., "A modular and extensible RNA-based gene-regulatory platform for engineering cellular function," *Proc. Natl. Acad. Sci. USA*, 104(36):14283-14288 (2007).
Win et al., "Higher-order cellular information processing with synthetic RNA devices," *Science*, 322:456-460 (2008).
Win et al., "Frameworks for programming biological function through RNA parts and devices," *Chem. Biol.*, 16:298-310 (2009).
Winkler et al., "An mRNA Structure that Controls Gene Expression by Binding FMN," *Proc. Natl. Acad. Sci. USA*, 99:15908-15913 (2002).
Winkler et al., "Thiamine derivatives bind messenger RNAs directly to regulate bacterial gene expression," *Nature*, 419:952-956 (2002).
Winkler et al., "Genetic Control by Metabolite-Binding Riboswitches," *ChemBioChem.*, 4:1024-1032 (2003).
Winkler et al., "Control of gene expression by a natural metabolite-responsive ribozyme," *Nature*, 428:281-286 (2004).
Woodside et al., "Nanomechanical measurements of the sequence-dependent folding landscapes of single nucleic acid hairpins," *Proc. Natl. Acad. Sci. USA*, 103:6190-6195 (2006).

(56) References Cited

OTHER PUBLICATIONS

Xia et al., "Multiple shRNAs expressed by an inducible pol II promoter can knock down the expression of multiple target genes," *Biotechniques*, 41:64-68 (2006).

Yamamoto et al., "Identification of a functional promoter in the long terminal repeat of *Rous sarcoma* virus," *Cell*, 22:787-797 (1980).

Yang et al., "DNA ligands that bind tightly and selectively to cellobiose," *Proc. Natl. Acad. Sci. USA*, 95(10): 5462-5467 (1998).

Yelin et al., "Widespread occurrence of antisense transcription in the human genome," Nat *Biotechnol.*, 21:379-386 (2003).

Yen et al., "Exogenous control of mammalian gene expression through modulation of RNA self-cleavage," *Nature*, 431:471-476 (2004).

Yeom et al., "Characterization of DGCR8/Pasha, the essential cofactor for Drosha in primary miRNA processing," *Nucleic Acids Res.*, 34(16):4622-4629 (2006).

Yi et al., "Exportin-5 mediates the nuclear export of premicroRNAs and short hairpin RNAs," *Genes Dev.*, 17:3011-3016 (2003).

Yi et al., "Overexpression of exportin 5 enhances RNA interference mediated by short hairpin RNAs and micro RNAs," *RNA*, 11:220-226 (2005).

Yokobayashi et al., "Directed evolution of a genetic circuit," *Proc. Natl. Acad. Sci. USA*, 99:16587-16591 (2002).

Yu et al., "RNA interference by expression of short-interfering RNAs and hairpin RNAs in mammalian cells," *Proc. Natl. Acad. Sci. USA*, 99:6047-6052 (2002).

Yunusov et al., "Kinetic capillary electrophoresis-based affinity screening of aptamer clones," *Anal Chim Acta.*, 631(1):102-107 (2009).

Zaug et al., "A labile phosphodiester bond at the ligation junction in a circular intervening sequence RNA," *Science*, 224:574-578 (1984).

Zaug et al., "The intervening sequence RNA of Tetrahymena is an enzyme," *Science*, 231:470-475 (1986).

Zaug et al., "The Tetrahymena ribozyme acts like an RNA restriction endonuclease," *Nature*, 324:429-433 (1986).

Zeng et al., "Both natural and designed micro RNAs can inhibit the expression of cognate mRNAs when expressed in human cells," *Mol. Cell*, 9:1327-1333 (2002).

Zeng et al., "Sequence requirements for micro RNA processing and function in human cells," *RNA*, 9:112-123 (2003).

Zeng et al., "Structural requirements for pre-microRNA binding and nuclear export by Exportin 5," *Nucleic Acids Res.*, 32(16): 4776-4785 (2004).

Zeng et al., "Efficient processing of primary microRNA hairpins by Drosha requires flanking nonstructured RNA sequences," *J. Biol. Chem.*, 280:27595-27603 (2005).

Zeng et al., "Recognition and cleavage of primary microRNA precursors by the nuclear processing enzyme Drosha," *EMBO J.*, 24:138-148 (2005).

Zhou et al., "Novel Dual Inhibitory Function Aptamer-mRNA Delivery System for HIV-1 Therapy," *Molecular Therapy*, 16:1481-1489 (2008).

Zimmermann et al., "Interlocking structural motifs mediate molecular discrimination by a theophylline-binding RNA," *Nat. Struct. Biol.*, 4:644-649 (1997).

Zimmermann et al., "Molecular interactions and metal binding in the theophylline-binding core of an RNA aptamer," *RNA*, 6:659-667 (2000).

Zon, "Oligonucleotide analogues as potential chemotherapeutic agents," *Pharm. Res.*, 5:539-549 (1988).

\* cited by examiner

SEQ ID NO: 26

SEQUENCE LISTING

<160> NUMBER OF SEQ ID NOS: 31

<210> SEQ ID NO 1
<211> LENGTH: 97
<212> TYPE: RNA
<213> ORGANISM: Artificial Sequence
<220> FEATURE:
<223> OTHER INFORMATION: Synthetic RNA aptamer

<400> SEQUENCE: 1
ccuaggaaac aaacaaagcu gucaccggau gugcuuuccg gucugaugag uccgugagga    60
cgaaacagca aaaagaaaaa uaaaaacucg agaaaaa                            97

<210> SEQ ID NO 2
<211> LENGTH: 100
<212> TYPE: RNA
<213> ORGANISM: Artificial Sequence
<220> FEATURE:
<223> OTHER INFORMATION: Synthetic RNA aptamer

<400> SEQUENCE: 2
gcugucaccg gaugugcuuu ccggucugau gaguccgugu ccauaccagc aucgucuuga    60
ugcccuuggc agggacggga cgaggacgaa acagcaaaaa                         100

<210> SEQ ID NO 3
<211> LENGTH: 102
<212> TYPE: RNA
<213> ORGANISM: Artificial Sequence
<220> FEATURE:
<223> OTHER INFORMATION: Synthetic RNA aptamer

<400> SEQUENCE: 3
gcugucaccg gaugugcuuu ccggucugau gaguccgugu ugcugauacc agcaucgucu    60

-continued

```
ugaugcccuu ggcagcagug gacgaggacg aaacagcaaa aa                  102

<210> SEQ ID NO 4
<211> LENGTH: 97
<212> TYPE: RNA
<213> ORGANISM: Artificial Sequence
<220> FEATURE:
<223> OTHER INFORMATION: Synthetic RNA aptamer

<400> SEQUENCE: 4
gcugucaccg gaugugcuuu ccggucugau gaguccgucc uggauaccag caucgucuug    60
augcccuugg cagucauaga ggacgaaaca gcaaaaa                            97

<210> SEQ ID NO 5
<211> LENGTH: 100
<212> TYPE: RNA
<213> ORGANISM: Artificial Sequence
<220> FEATURE:
<223> OTHER INFORMATION: Synthetic RNA aptamer

<400> SEQUENCE: 5
gcugucaccg gaugugcuuu ccggucugau gaguccgcgu ccauaccagc aucgucuuga   60
ugcccuuggc agggacggga cgaggacgaa acagcaaaaa                        100

<210> SEQ ID NO 6
<211> LENGTH: 48
<212> TYPE: RNA
<213> ORGANISM: Artificial Sequence
<220> FEATURE:
<223> OTHER INFORMATION: Synthetic RNA aptamer

<400> SEQUENCE: 6
aaaacauacc agauuucgau cuggagaauc caccagcuua agaagugg               48

<210> SEQ ID NO 7
<211> LENGTH: 118
<212> TYPE: RNA
<213> ORGANISM: Artificial Sequence
<220> FEATURE:
<223> OTHER INFORMATION: Synthetic RNA aptamer

<400> SEQUENCE: 7
gcugucaccg gaugugcuuu ccggucugau gaguccgugu ccaaaacaua ccagauuucg   60
aucuggagaa ggugaagaau ucgaccaccu ggacgggacg aggacgaaac agcaaaaa   118

<210> SEQ ID NO 8
<211> LENGTH: 57
<212> TYPE: RNA
<213> ORGANISM: Artificial Sequence
<220> FEATURE:
<223> OTHER INFORMATION: Synthetic RNA aptamer

<400> SEQUENCE: 8
gcugucaccg gaugugcuuu ccgguacgug agguccguga ggacagaaca gcaaaaa     57

<210> SEQ ID NO 9
<211> LENGTH: 57
<212> TYPE: RNA
<213> ORGANISM: Artificial Sequence
<220> FEATURE:
<223> OTHER INFORMATION: Synthetic RNA aptamer

<400> SEQUENCE: 9
uccggucuga ugaguccgug aggacgaaac agcugugcuu gcugucaccg gaaaaaa     57
```

```
<210> SEQ ID NO 10
<211> LENGTH: 80
<212> TYPE: RNA
<213> ORGANISM: Artificial Sequence
<220> FEATURE:
<223> OTHER INFORMATION: Synthetic RNA aptamer

<400> SEQUENCE: 10
gcugucaccg gaauaccagc aucgucuuga ugcccuuggc aguccggucu gaugaguccg    60
ugaggacgaa acagcaaaaa                                                80

<210> SEQ ID NO 11
<211> LENGTH: 83
<212> TYPE: RNA
<213> ORGANISM: Artificial Sequence
<220> FEATURE:
<223> OTHER INFORMATION: Synthetic RNA aptamer

<400> SEQUENCE: 11
gcugucaccg gaugugcuuu ccggucugau gaguccauac cagcaucguc uugaugcccu    60
uggcagggac gaaacagcaa aaa                                            83

<210> SEQ ID NO 12
<211> LENGTH: 95
<212> TYPE: RNA
<213> ORGANISM: Artificial Sequence
<220> FEATURE:
<223> OTHER INFORMATION: Synthetic RNA aptamer

<400> SEQUENCE: 12
gcugucaccg gauguaguga uaccagcauc gucuugaugc ccuuggcagc acugcuuucc    60
ggucugauga guccgugagg acgaaacagc aaaaa                               95

<210> SEQ ID NO 13
<211> LENGTH: 95
<212> TYPE: RNA
<213> ORGANISM: Artificial Sequence
<220> FEATURE:
<223> OTHER INFORMATION: Synthetic RNA aptamer

<400> SEQUENCE: 13
gcugucaccg gaugugcuuu ccggucugau gaguccguag ugauaccagc aucgucuuga    60
ugcccuuggc agcacugagg acgaaacagc aaaaa                               95

<210> SEQ ID NO 14
<211> LENGTH: 100
<212> TYPE: RNA
<213> ORGANISM: Artificial Sequence
<220> FEATURE:
<223> OTHER INFORMATION: Synthetic RNA aptamer

<400> SEQUENCE: 14
gcugucaccg gaugugcuuu ccggucugau gaguccugugu ucauaccagc aucgucuuga   60
ugcccuuggc agggacggga cgaggacgaa acagcaaaaa                          100

<210> SEQ ID NO 15
<211> LENGTH: 100
<212> TYPE: RNA
<213> ORGANISM: Artificial Sequence
<220> FEATURE:
<223> OTHER INFORMATION: Synthetic RNA aptamer

<400> SEQUENCE: 15
```

```
gcugucaccg gaugugcuuu ccggucugau gaguccgugu ucauaccagc aucgucuuga    60
ugcccuuggc agggacgggg cgaggacgaa acagcaaaaa                        100

<210> SEQ ID NO 16
<211> LENGTH: 100
<212> TYPE: RNA
<213> ORGANISM: Artificial Sequence
<220> FEATURE:
<223> OTHER INFORMATION: Synthetic RNA aptamer

<400> SEQUENCE: 16
gcugucaccg gaugugcuuu ccggucugau gaguccgugu ccauaccagc aucgucuuga    60
ugcccuuggc agggacggga cgaggacgaa acagcaaaaa                        100

<210> SEQ ID NO 17
<211> LENGTH: 100
<212> TYPE: RNA
<213> ORGANISM: Artificial Sequence
<220> FEATURE:
<223> OTHER INFORMATION: Synthetic RNA aptamer

<400> SEQUENCE: 17
gcugucaccg gaugugcuuu ccggucugau gaguccgugu ccauaccagc aucgucuuga    60
ugcccuuggc agggacggga cgaggacgaa acagcaaaaa                        100

<210> SEQ ID NO 18
<211> LENGTH: 102
<212> TYPE: RNA
<213> ORGANISM: Artificial Sequence
<220> FEATURE:
<223> OTHER INFORMATION: Synthetic RNA aptamer

<400> SEQUENCE: 18
gcugucaccg gaugugcuuu ccggucugau gaguccgugu ccgauaccag caucgucuug    60
augcccuugg cagcggacgg gacgaggacg aaacagcaaa aa                    102

<210> SEQ ID NO 19
<211> LENGTH: 102
<212> TYPE: RNA
<213> ORGANISM: Artificial Sequence
<220> FEATURE:
<223> OTHER INFORMATION: Synthetic RNA aptamer

<400> SEQUENCE: 19
gcugucaccg gaugugcuuu ccggucugau gaguccguug uccauaccag caucgucuug    60
augcccuugg cagggacggg acagaggacg aaacagcaaa aa                    102

<210> SEQ ID NO 20
<211> LENGTH: 102
<212> TYPE: RNA
<213> ORGANISM: Artificial Sequence
<220> FEATURE:
<223> OTHER INFORMATION: Synthetic RNA aptamer

<400> SEQUENCE: 20
gcugucaccg gaugugcuuu ccggucugau gaguccguug uccauaccag caucgucuug    60
augcccuugg cagggacggg acggaggacg aaacagcaaa aa                    102

<210> SEQ ID NO 21
<211> LENGTH: 105
<212> TYPE: RNA
<213> ORGANISM: Artificial Sequence
```

```
<220> FEATURE:
<223> OTHER INFORMATION: Synthetic RNA aptamer

<400> SEQUENCE: 21
gcugucaccg gaugugcuuu ccggucugau gaguccguug uccaauacca gcaucgucuu      60
gaugcccuug gcaguggaug gggacggagg acgaaacagc aaaaa                    105

<210> SEQ ID NO 22
<211> LENGTH: 102
<212> TYPE: RNA
<213> ORGANISM: Artificial Sequence
<220> FEATURE:
<223> OTHER INFORMATION: Synthetic RNA aptamer

<400> SEQUENCE: 22
gcugucaccg gaugugcuuu ccggucugau gaguccgugu ugcugauacc agcaucgucu      60
ugaugcccuu ggcagcagug gacgaggacg aaacagcaaa aa                       102

<210> SEQ ID NO 23
<211> LENGTH: 101
<212> TYPE: RNA
<213> ORGANISM: Artificial Sequence
<220> FEATURE:
<223> OTHER INFORMATION: Synthetic RNA aptamer

<400> SEQUENCE: 23
gcugucaccg gaugugcuuu ccggucugau gaguccgugu gcugauacca gcaucgucuu      60
gaugcccuug gcagcagugg acgaggacga aacagcaaaa a                        101

<210> SEQ ID NO 24
<211> LENGTH: 100
<212> TYPE: RNA
<213> ORGANISM: Artificial Sequence
<220> FEATURE:
<223> OTHER INFORMATION: Synthetic RNA aptamer

<400> SEQUENCE: 24
gcugucaccg gaugugcuuu ccggucugau gaguccgugu gcugauacca gcaucgucuu      60
gaugcccuug gcagcaguga cgaggacgaa acagcaaaaa                          100

<210> SEQ ID NO 25
<211> LENGTH: 37
<212> TYPE: RNA
<213> ORGANISM: Artificial Sequence
<220> FEATURE:
<223> OTHER INFORMATION: Synthetic RNA aptamer
<220> FEATURE:
<221> NAME/KEY: variation
<222> LOCATION: (1)...(4)
<223> OTHER INFORMATION: N = A, T, G or U
<220> FEATURE:
<221> NAME/KEY: variation
<222> LOCATION: 6
<223> OTHER INFORMATION: N = A, T or U
<220> FEATURE:
<221> NAME/KEY: variation
<222> LOCATION: (7)...(14)
<223> OTHER INFORMATION: N = A, T, G or U
<220> FEATURE:
<221> NAME/KEY: variation
<222> LOCATION: 19
<223> OTHER INFORMATION: N = A, T, G or U
<220> FEATURE:
<221> NAME/KEY: variation
<222> LOCATION: (23)...(28)
<223> OTHER INFORMATION: N = A, T, G or U
<220> FEATURE:
<221> NAME/KEY: variation
```

```
<222> LOCATION: (34)...(37)
<223> OTHER INFORMATION: N = A, T, G or U

<400> SEQUENCE: 25
nnnnunnnnn nnnncugang agnnnnnncg aaannnn                             37

<210> SEQ ID NO 26
<211> LENGTH: 50
<212> TYPE: RNA
<213> ORGANISM: Artificial Sequence
<220> FEATURE:
<223> OTHER INFORMATION: Synthetic RNA aptamer

<400> SEQUENCE: 26
cugucaccgg augugcuuuc cggucugaug aguccgugag gacgaaacag               50

<210> SEQ ID NO 27
<211> LENGTH: 46
<212> TYPE: RNA
<213> ORGANISM: Artificial Sequence
<220> FEATURE:
<223> OTHER INFORMATION: Synthetic RNA aptamer

<400> SEQUENCE: 27
gguaguaacu gaacugauga gucgcugaaa ugcgacgaaa ggcaca                   46

<210> SEQ ID NO 28
<211> LENGTH: 18
<212> TYPE: RNA
<213> ORGANISM: Artificial Sequence
<220> FEATURE:
<223> OTHER INFORMATION: Synthetic RNA aptamer

<400> SEQUENCE: 28
ugugccucuu cagcuacc                                                  18

<210> SEQ ID NO 29
<211> LENGTH: 64
<212> TYPE: RNA
<213> ORGANISM: Artificial Sequence
<220> FEATURE:
<223> OTHER INFORMATION: Synthetic RNA aptamer

<400> SEQUENCE: 29
agcaguaaca aauucuuaaa acaacugaug agucgcugaa augcgacgaa accauguggu    60
cucu                                                                 64

<210> SEQ ID NO 30
<211> LENGTH: 36
<212> TYPE: RNA
<213> ORGANISM: Artificial Sequence
<220> FEATURE:
<223> OTHER INFORMATION: Synthetic RNA aptamer

<400> SEQUENCE: 30
agagaccaca uggcuuguu agaauuuguu acugcu                               36

<210> SEQ ID NO 31
<211> LENGTH: 9
<212> TYPE: DNA
<213> ORGANISM: Artificial Sequence
<220> FEATURE:
<223> OTHER INFORMATION: Synthetic catalytic core sequence
```

```
<400> SEQUENCE: 31 ctagatgag                                                                9
```

MODULAR APTAMER-REGULATED RIBOZYMES

CROSS-REFERENCE TO RELATED APPLICATIONS

This application is a divisional application of U.S. Ser. No. 11/938,220, filed Nov. 9, 2007, now U.S. Pat. No. 8,158,595, which claims the benefit of and priority to U.S. Provisional Application No. 60/857,824 filed on Nov. 9, 2006, and U.S. Provisional Application No. 60/875,774 filed on Dec. 19, 2006, the contents of which applications are incorporated herein by reference in their entirety.

STATEMENT REGARDING FEDERALLY SPONSORED R & D

This invention was made with government support under Grant No. W911NF-05-1-0281 awarded by the United States Army Research Office and under Grant No. GM074767 awarded by the National Institute of Health. The government has certain rights in the invention.

BACKGROUND OF THE INVENTION

Basic and applied biological research and biotechnology are limited by our ability to get information into and out from living systems, and to act on information inside living systems. Endy (2005) Nature 438:449-53; Voigt (2006) Curr Opin Biotechnol 17:548-57; and Kobayashi et al. (2004) Proc Natl Acad Sci USA 101:8414-9. For example, there are only a small number of inducible promoter systems available to provide control over gene expression in response to exogenous molecules. Gossen et al. (1992) Proc Natl Acad Sci USA 89:5547-51; and Lutz et al. (1997) Nucleic Acids Res 25:1203-10. Many of the molecular inputs to these systems are not ideal for broad implementation, as they can be expensive and introduce undesired pleiotropic effects. In addition, broadly-applicable methods for getting information out of cells non-invasively have been limited to strategies that rely on protein and promoter fusions to fluorescent proteins, which enable researchers to monitor protein levels and localization and transcriptional outputs of networks, leaving a significant amount of the cellular information content currently inaccessible.

To address these challenges scalable platforms are needed for reporting on, responding to, and controlling any intracellular component in a living system. A striking example of a biological communication and control system is the class of RNA regulatory elements called riboswitches, comprised of distinct sensor and actuation (gene regulatory) functions, that control gene expression in response to specific ligand concentrations. Mandal et al. (2004) Nat Rev Mol Cell Biol 5:451-63. Building on these natural examples, engineered riboswitch elements have been developed for use as synthetic ligand-controlled gene regulatory systems. Kim et al. (2005) RNA 11:1667-77; An C I et al. (2006) RNA 12:710-6; Bayer et al. (2005) Nat Biotechnol 23:337-43; and Isaacs et al. (2006) Nat Biotechnol 24:545-54. However, as versatile as these early examples of riboswitch engineering are, there are additional challenges posed, such as greater ease in portability across organisms and systems, and improved modularity and component reuse.

There is a need, therefore, to develop a universal and extensible RNA-based platform that will provide a framework for the reliable design and construction of gene regulatory systems that can control the expression of specific target genes in response to various effector molecules.

SUMMARY OF THE INVENTION

Implementing five engineering design principles (DPs) in addressing the challenge of developing a universal and extensible RNA-based platform, this application describes an extensible RNA-based framework for engineering ligand-controlled gene regulatory systems, called ribozyme switches, that exhibit tunable regulation, design modularity, and target specificity. In particular, the subject ribozyme switches address: scalability (DP1: a sensing platform enabling de novo generation of ligand-binding elements for implementation within the sensor domain); portability (DP2: a regulatory element that is independent of cell-specific machinery or regulatory mechanisms for implementation within the actuator domain); utility (DP3: a mechanism through which to modularly couple the control system to functional level components); composability (DP4: a mechanism by which to modularly couple the actuator and sensor domains without disrupting the activities of these individual elements); and reliability (DP5: a mechanism through which to standardize the transmission of information from the sensor domain to the actuator domain).

One aspect of the invention relates to an aptamer-regulated cis-acting hammerhead ribozyme. In general this regulated ribozyme includes a cis-acting hammerhead ribozyme (or "chRz"), e.g., a ribozyme comprising of a catalytic core with stem I, stem II and stem III duplex regions extending therefrom. Each of the stem I and stem II duplexes include a single-stranded loop region opposite to the catalytic core, these loops being referred to as loop I and loop II respectively. An example of this structure is shown in FIG. 1. The regulated ribozyme also includes at least one aptamer directly coupled through an information transmission domain to loop I and/or loop II. The aptamer can be chosen based on its ability to bind a ligand or otherwise "sense" a change in environment (such as pH, temperature, osmolarity, salt concentration, etc) in a manner that alters the base-pairing with the information transmission domain that is carried over as a structural change in the hammerhead ribozyme. In certain embodiments, the aptamer and information transmission domains are integrated such that binding of the ligand to the aptamer causes a change in the interaction of the information transmission domain with one or more of the loop, the stem or the catalytic core such that the ribozyme undergoes self-cleavage of a backbone phosphodiester bond at a rate dependent upon the presence or absence of the ligand. In certain embodiments, the presence of ligand will increase the rate of self-cleavage relative to the absence of ligand, while in other embodiments the rate of self-cleavage is greater in the absence of ligand relative to the presence of ligand. In certain preferred embodiments, the difference in the rate of cleavage is at least 100 fold, and even more preferably 1000 or 10,000 fold.

In certain embodiments, the hammerhead ribozyme core comprises the polynucleotide sequence 5'- . . . UCH . . . UWYGANGA . . . GAAA . . . -3', wherein H is selected from A, C, and U; W is selected from C, U, and A; Y is selected from C and U; and N is selected from A, C, G, and U.

In certain embodiments, binding of the ligand to the aptamer alters the size of the loop I or loop II to which the information transmission domain and aptamer are coupled, and thereby alters the ability of the ribozyme to undergo self-cleavage in a manner dependent on the ligand, such as by altering tertiary structural contacts involving the loop to which the information transmission domain and aptamer are coupled.

In certain embodiments, binding of the ligand to the aptamer alters the size of the catalytic core, thereby altering the ability of the ribozyme to undergo self-cleavage in a manner dependent on the ligand.

In certain embodiments, binding of the ligand to the aptamer can cause helix-slipping involving the information transmission domain.

In certain embodiments, binding of the ligand to the aptamer causes strand-displacement involving the information transmission domain.

In certain embodiments, a single information transmission domain and aptamer are coupled to loop I, while in others a single information transmission domain and aptamer are coupled to loop II. However, the present invention contemplates ribozymes having 2 or more (e.g., 2, 3, 4, 5) information transmission domain/aptamers coupled through loops I and II. For instance, the ribozyme can be engineered to have a first aptamer coupled to loop I through a first information transmission domain and a second aptamer coupled to loop II through a second information transmission domain. The aptamers can be chosen to bind the same ligand, including binding to the same ligand but with different affinities, or the aptamers can be chosen to bind different ligands from one another.

In certain embodiments, the aptamer is chosen to bind a small molecule, such as one having a molecular weight less than 2500 amu and/or one which is cell permeable. In other embodiments, the aptamer is chosen to bind a metal ion.

In certain embodiments, the aptamer is chosen to bind a ligand which is a natural product, such as a signal transduction second messenger molecule.

The aptamer can be chose to selectively bind a protein, and in certain embodiments, that selectivity can be for a post-translationally modified form of the protein, or the unmodified protein. The aptamer may also be selected to be able to selectively bind a particular splice variant of a protein.

To further illustrate, the aptamer can be one which binds a ligand selected from the group consisting of polypeptides, peptides, nucleic acids, carbohydrates, fatty acids and lipids, a non-peptide hormone (such as steroids) and metabolic precursors or products thereof.

It may be an aptamer that senses a change in substrate or product of a metabolic process, such as binding a ligand selected from the group consisting of enzyme co-factors, enzyme substrates and products of enzyme-mediated reactions.

In certain embodiments, the ribozymes described herein (cis or trans) can be generated using RNA or an analog thereof. In certain embodiments, the ribozyme is comprised of RNA or an analog thereof, and DNA or an analog thereof. For instance, the ribozyme core can be RNA or an analog thereof, and the one or more of the stems of the ribozyme can be DNA or an analog thereof. Merely to illustrate, a aptamer-regulated ribozyme of the present invention may include at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

In addition to the nucleic acid that is itself functional as the regulated ribozyme, the present invention also provides expression constructs that include a "coding sequence" which, when transcribed to RNA, produces the aptamer regulated cis-acting hammerhead ribozyme, and may include one or more transcriptional regulatory sequences that regulate transcription of that sequence in a cell containing the expression construct.

In certain embodiments, the expression construct can be designed to include one or more ribozymes in an RNA transcript, such as in the 3' untranslated region (3'-UTR), so as to regulate transcription, stability and/or translation of that RNA transcript in a manner dependent on the ligand. To further illustrate, the expression construct can include a coding sequence for a polypeptide such that the mRNA transcript includes both the polypeptide coding sequence as well as one or more of the regulated ribozymes. In this way, expression of the polypeptide can be rendered dependent on the ligand to which the aptamer binds.

The present invention also provides cells that have been engineered to include such expression constructs. Still another aspect of the invention relates to methods for regulating expression of a recombinant gene. Those methods include providing such a cell, and contacting the cell with the ligand in an amount that alters the activity of the ribozyme, and therefore, the expression of the recombinant gene.

Still another aspect of the invention relates to an aptamer-regulated trans-acting hammerhead ribozyme. In general, the regulated trans-ribozyme includes a trans-acting hammerhead ribozyme (or "thRz"), e.g., a ribozyme having a catalytic core, a 5' targeting arm which hybridizes to a 3' sequence of a target nucleic acid, a 3' targeting arm which hybridizes to a 5' sequence of the target nucleic acid, and a stem duplex region extending from the catalytic core with a single-stranded loop region opposite the catalytic core. An example of this structure is shown in FIG. 20. The ribozyme includes an aptamer and an information transmission domain having a first and second end, wherein the information transmission domain is directly coupled to the loop through the first end and the aptamer through said second end. The aptamer can be chosen based on its ability to bind a ligand or otherwise "sense" a change in environment (such as temperature, pH, etc) in a manner that alters the interaction of the information transmission domain with one or more of the loop, the stem or the catalytic core, such that the ribozyme cleaves the target nucleic acid at a rate dependent upon the presence or absence of said ligand. In certain embodiments, the presence of ligand will increase the rate of cleavage relative to absence of the ligand, while in other embodiments the rate of cleavage is greater in the absence of ligand relative to the presence of ligand. In certain preferred embodiments, the difference in the rate of cleave is at least 100 fold, and even more preferably 1000 or 10,000 fold.

In certain embodiments, binding of the ligand to the aptamer alters the size of the loop, and thereby alters the ability of the ribozyme to cleave the target nucleic acid in a manner dependent on the ligand.

In certain embodiments, binding of the ligand to the aptamer alters the size of the catalytic core, thereby altering the ability of the ribozyme to cleave the target nucleic acid in a manner dependent on the ligand.

In certain embodiments, binding of the ligand to the aptamer can cause helix-slipping involving the information transmission domain.

In certain embodiments, binding of the ligand to the aptamer causes strand-displacement involving the information transmission domain.

In certain embodiments, the aptamer is chosen to bind a small molecule, such as one having a molecular weight less than 2500 amu and/or one which is cell permeable. In other embodiments, the aptamer is chosen to bind a metal ion.

In certain embodiments, the aptamer is chosen to bind a ligand which is a natural product, such as a signal transduction second messenger molecule. The aptamer can be chosen to selectively bind a protein, and in certain embodiments, that selectivity can be for a post-translationally modified form of the protein, or the unmodified protein. The aptamer may also be selected to be able to selectively bind a particular splice variant of a protein.

To further illustrate, the aptamer can be one which binds a ligand selected from the group consisting of polypeptides, peptides, nucleic acids, carbohydrates, fatty acids and lipids, a non-peptide hormone (such as steroids) and metabolic precursors or products thereof.

It may be an aptamer that senses a change in substrate or product of a metabolic process, such as binding a ligand selected from the group consisting of enzyme co-factors, enzyme substrates and products of enzyme-mediated reactions.

In certain embodiments, the ribozymes described herein (cis or trans) can be generated using RNA or an analog thereof. In certain embodiments, the ribozyme is comprised of RNA or an analog thereof, and DNA or an analog thereof. For instance, the ribozyme core can be RNA or an analog thereof, and the one or more of the stems of the ribozyme can be DNA or an analog thereof.

In addition to the nucleic acid that is itself functional as the regulated ribozyme, the present invention also provides expression constructs that include a "coding sequence" which, when transcribed to RNA, produces the aptamer regulated trans-acting hammerhead ribozyme, and may include one or more transcriptional regulatory sequences that regulate transcription of that sequence in a cell containing the expression construct. The present invention also provides cells that have been engineered to include such expression constructs. Still another aspect of the invention relates to methods for regulating expression of a target gene (or other RNA species). Those methods include providing such a cell wherein the trans-acting ribozyme, in its active form, cleave an mRNA that is transcribed in the cell, and contacting the cell with the ligand in an amount that alters the activity of the ribozyme, and therefore, the expression of the target gene.

Another aspect of the invention provides a cell having a metabolic pathway of one or more reactions, and in which one or more of the subject aptamer-regulated trans-acting hammerhead ribozymes act as control elements on the metabolic pathway by inhibiting expression of one or more target genes. In such embodiments, ligand binding to the aptamer causes a change in the trans-acting ribozyme between two conformational states, in one of which the trans-acting ribozyme inhibits expression of a target gene and in the other of which the trans-acting ribozyme does not inhibit expression of the target gene. In this embodiment, the metabolic pathway is regulated at least in part by the activity level of the trans-acting nucleic acid, and therefore, the level of aptamer present. Such embodiments may be used to regulate a metabolic pathway that includes at least one reaction mediated by an enzyme, such as where the trans-acting ribozyme regulates expression of the enzyme.

Likewise, another aspect of the invention provides a cell having a metabolic pathway of one or more reactions, and in which one or more of the subject aptamer-regulated cis-acting hammerhead ribozymes act as control elements on the metabolic pathway by inhibiting expression of one or more target genes into which the cis-acting ribozymes has been engineered so as to be part of the mRNA transcript of the gene, preferably as part of the 3'-UTR. In such embodiments, the ligand binding to the aptamer causes a change in the cis-acting ribozyme between two conformational states, in one of which the cis-acting ribozyme inhibits expression of the target gene by undergoing self-cleavage, and in the other of which the trans-acting ribozyme does not cleave itself. In this embodiment, the metabolic pathway is regulated at least in part by the activity level of the cis-acting nucleic acid, and therefore, the level of aptamer present. Such embodiments may be used to regulate a metabolic pathway that includes at least one reaction mediated by an enzyme, such as where the cis-acting ribozyme regulates expression of the enzyme.

Another aspect of the invention provides a method for rendering expression of a target gene in a cell dependent on the presence or absence of a ligand, by utilizing a version of the subject aptamer-regulated trans-acting ribozyme that, in it's active form, cleaves a transcript produced by transcription of the target gene, and thereby inhibits expression of the target gene in a manner dependent on the presence or absence of the ligand. Such embodiments can be designed to rely on ligands that are produced by the cell, or designed to rely on ligands that are cell permeable agents contacted with the cell.

Likewise, the aptamer-regulated cis-acting ribozymes of the invention can be used to render expression of a target gene in a cell dependent on the presence or absence of a ligand. In these embodiments, the cell is engineered with an expression construct that includes a coding sequence for the target gene, which when transcribed to an mRNA transcript, also includes one or more aptamer-regulated cis-acting ribozymes in the mRNA. Ligand binding to the aptamer causes a change in the cis-acting ribozyme between two conformational states, in one of which the cis-acting ribozyme inhibits expression of the target gene present with the ribozyme in the same transcript, while in the other the cis-acting ribozyme does not inhibit expression of the target gene. In this way, the cis-acting ribozyme(s) present in the transcript can regulate transcription, stability and/or translation of the mRNA in a manner dependent on the ligand. Such embodiments can be designed to rely on ligands that are produced by the cell, or designed to rely on ligands that are cell permeable agents contacted with the cell.

In still another embodiment, the present invention provides a method for determining the amount of an analyte in a cell which expresses a reporter gene by way of the cell also containing an aptamer-regulated trans-acting ribozyme that cleaves the reporter gene in a manner dependent on the level of analyte. Binding of the analyte to the aptamer induces a conformational change between active and inactive forms the trans-acting ribozyme, and the active form inhibits expression of the reporter. The method can include measuring the amount of expression of the reporter gene, and correlating the amount of expression of the reporter gene with the amount of analyte, thereby determining the amount of the ligand in the cell. Exemplary reporter molecules include, without limitation, fluorescent or luminescent reporter proteins such as green fluorescent protein (GFP) or luciferase, enzymatic reporters such as alkaline phosphatase, or colorimetric reporters such as lacZ.

Likewise, in other embodiments, the present invention provides a method for determining the amount of an analyte in a cell which expresses a reporter gene that produces an mRNA that includes one or more aptamer-regulated cis-acting ribozyme that regulate the transcription, stability and/or translation of the mRNA transcript in a manner dependent on the level of analyte. Binding of the analyte to the aptamer causes a change in the cis-acting ribozyme between two conformational states, in one of which the cis-acting ribozyme inhibits (or otherwise reduces) expression of the reporter gene and in the other of which the cis-acting ribozyme does not inhibit expression of the reporter gene. The method can include measuring the amount of expression of the reporter gene, and correlating the amount of expression of the reporter gene with the amount of analyte, thereby determining the amount of the ligand in the cell. Exemplary reporter molecules include, without limitation, fluorescent or luminescent reporter proteins such as green fluorescent protein (GFP) or luciferase, enzymatic reporters such as alkaline phosphatase, or colorimetric reporters such as lacZ.

Yet another aspect of the invention provides methods and compositions for treating or preventing infection by a pathogenic agent. Such methods include administering, to a patient, a sufficient amount of an aptamer-regulated trans-acting ribozyme that cleaves a pathogen or cellular gene, e.g. required for pathogenesis, in a manner dependent on aptamer binding of a ligand that is produced as a consequence of pathogenic infection.

Another aspect of the invention provides a method for causing phenotypic regulation of cell growth, differentiation or viability in cells of a patient. Such methods include introducing one of the subject aptamer-regulated trans-acting ribozymes into cells of the patient. In these embodiments, the aptamer binds to a ligand present in the patient which has a concentration that is dependent on cellular phenotype. Binding of the ligand to the aptamer induces a conformational change between active and inactive forms of the trans-acting ribozyme, where the active form of the trans-acting ribozyme inhibits expression of a target gene that alters the regulation of cell growth, differentiation or viability in the cells. The target of the ribozyme can be selected to either induce or prevent cell death, induce or inhibit differentiation, or induce or inhibit proliferation of the cells in a manner dependent on the presence of the ligand. In certain embodiments, the ribozyme, or an expression construct for transcribing the ribozyme in cells, is introduced ex vivo into cells which are then transplanted into the patient.

Likewise, the present invention provides a method for causing phenotypic regulation of cell growth, differentiation or viability in cells transplanted into a patient, by introducing into cells ex vivo an expression construct that produces a transcript that includes a coding sequence for a polypeptide that causes phenotypic regulation, and one or more of the subject aptamer-regulated cis-acting ribozymes that regulate the level of expression of the polypeptide in a manner dependent on the concentration of ligand, and the concentration of the ligand is in turn dependent on the cellular phenotype. In such embodiments, ligand binding to the aptamer causes a change in the cis-acting ribozyme between two conformational states, in one of which the cis-acting ribozyme inhibits expression of the polypeptide and in the other of which the cis-acting ribozyme does not inhibit expression of the polypeptide. Thus, expression of the polypeptide alters regulation of cell growth, differentiation or viability in the cells in a manner dependent on the concentration of ligand.

Merely for illustration, the method can be used to prevent the growth of hyperplastic or tumor cells, or even the unwanted proliferation of normal cells. It can be used to induce the death of fat cells. It can also be used to regulate growth and differentiation of stem cells, or to regulate activation of an immune response.

Another aspect of the invention provides pharmaceutical preparations and compositions comprising an aptamer-regulated ribozyme of the present invention, an expression construct which, when transcribed, produces an RNA including the ribozyme, and a pharmaceutically acceptable carrier suitable for administration use to a human or non-human patient. Optionally, the pharmaceutically acceptable carrier is selected from pharmaceutically acceptable salts, ester, and salts of such esters. In certain preferred embodiments, the present invention provides a pharmaceutical package or kit comprising the pharmaceutical preparation which includes at least one aptamer-regulated ribozyme and a pharmaceutically acceptable carrier, in association with instructions (written and/or pictorial) for administering the preparation to a human patient.

Still another aspect of the present invention provides a method of conducting a pharmaceutical business comprising: (a) identifying an aptamer-regulated trans-ribozyme which, when switched "on," inhibits proliferation of target cells in vivo and reduces the effects of a disorder involving unwanted proliferation of the target cells; (b) conducting therapeutic profiling of the an aptamer-regulated trans-ribozyme identified in step (a) for efficacy and toxicity in animals; and (c) formulating a pharmaceutical preparation including one or more of the aptamer-regulated trans-ribozymes identified in step (b) as having an acceptable therapeutic profile.

The method of conducting a pharmaceutical business may further comprise an additional step of establishing a distribution system for distributing the pharmaceutical preparation for sale, and optionally, establishing a sales group for marketing the pharmaceutical preparation.

Yet still another aspect of the present invention provides a method of conducting a pharmaceutical business comprising: (a) identifying an aptamer-regulated trans-ribozyme which, when switched "on," inhibits proliferation of target cells in vivo and reduces the effects of a disorder involving unwanted proliferation of the target cells; (b) (optionally) conducting therapeutic profiling of an aptamer-regulated trans-ribozyme identified in step (a) for efficacy and toxicity in animals; and (c) licensing, to a third party, the rights for further development of the aptamer-regulated trans-ribozyme.

The skilled artisan recognizes that an aptamer-regulated trans-ribozyme that is useful for treating any disorder, including, but not limited to inhibiting pathogenic replication and/or infection, regulation of the immune response, or modulation of the cellular state of a cell, may be used in the methods of conducting a pharmaceutical business as described herein.

Still other aspects of the invention provide a library of aptamer-regulated ribozymes, such as libraries having a variegated population of ribozymes having different aptamers and/or different ribozyme regions (such as targeting sequences, stem or loop sequences, as described above). These libraries may have diversity among the aptamers with respect to the types of ligands that can be bound (specificity) and/or the variation in affinity for the same ligand.

Certain embodiments are also directed to a method of establishing a conditional genetic network. The method may comprise engineering a cell to include an aptamer-regulated trans-acting ribozyme, wherein the aptamer domain is responsive to a ligand and the ribozyme domain is targeted to a gene, the expression of which is otherwise unassociated with a signaling, metabolic, enzymatic, or any biochemical pathway that produces the ligand or modulates the level of the ligand. Thus, when switched "on", the ribozyme modulates expression of the gene, thereby establishing a conditional genetic network. A conditional genetic network may be useful, for example, in engineering an intracellular signaling network.

Likewise, the aptamer-regulated cis-acting ribozymes of the invention can be used to establish a conditional genetic network. In these embodiments, the cell is engineered with an expression construct that includes a coding sequence for the target gene, which when transcribed to an mRNA transcript, also includes one or more aptamer-regulated cis-acting ribozymes in the mRNA. The expression of the target gene is otherwise unassociated with a signaling, metabolic, enzymatic, or any biochemical pathway that produces the ligand or modulates the level of the ligand. This, when switched "on", the ribozyme modulates expression of the gene, thereby establishing a conditional genetic network.

DETAILED DESCRIPTION OF THE INVENTION

I. Overview

Figure 1A:
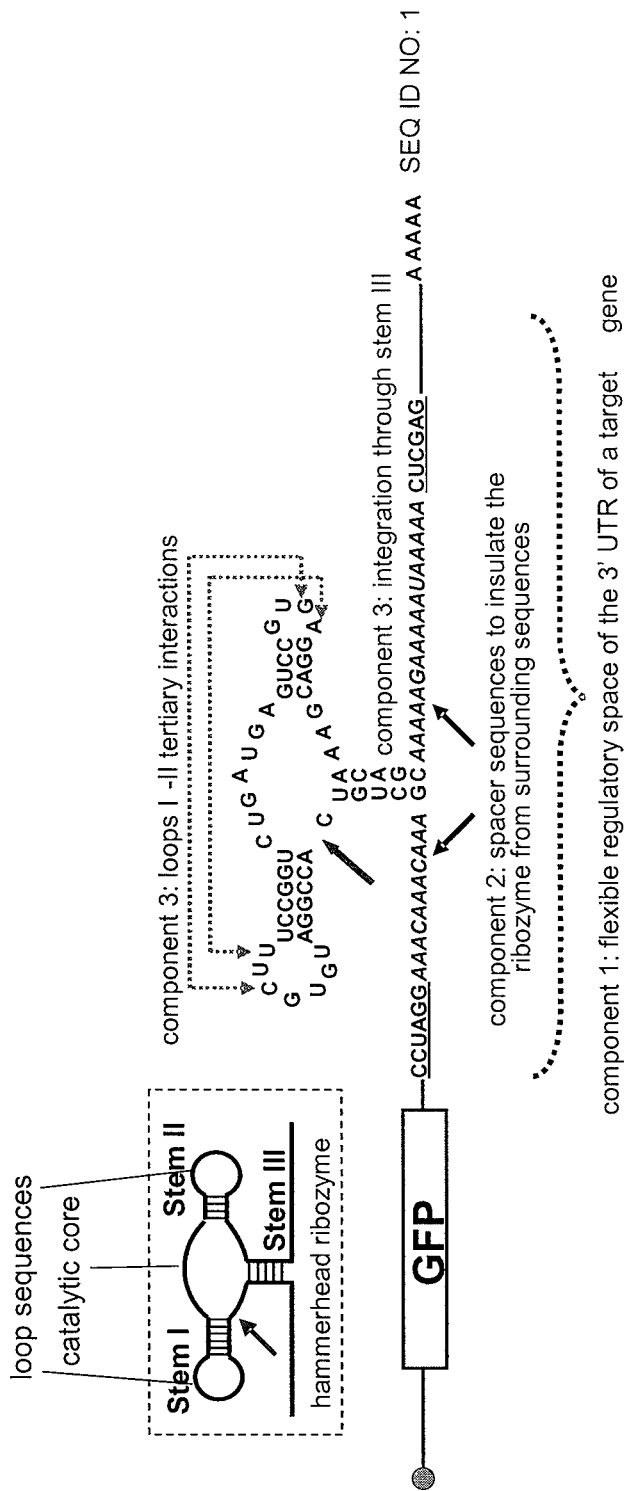
FIG. 1. General design strategy for engineering ribozyme switches. The arrow indicates the cleavage site. (A) General compositional framework and design strategy for engineering cis-acting hammerhead ribozyme-based regulatory systems; restriction enzyme sites are underlined. (B) Modular coupling strategies of the sensor and regulatory domains to maintain in vivo activity of the individual domains.

Engineered biological systems hold promise in addressing pressing human needs in chemical processing, energy production, materials construction, and maintenance and enhancement of human health and the environment. However, significant advancements in our ability to engineer biological systems have been limited by the foundational tools available for reporting on, responding to, and controlling intracellular components in living systems. Portable and scalable platforms are needed for the reliable construction of such communication and control systems across diverse organisms.

The present invention provides an extensible RNA-based framework for engineering ligand-controlled gene regulatory systems, called ribozyme switches, that exhibit tunable regulation, design modularity, and target specificity. These switch platforms contain a sensor domain, comprised of an aptamer sequence, and an actuator domain, comprised of a hammerhead ribozyme sequence. As described in further detail below, the aptamer is directly coupled to a loop of the hammerhead ribozyme. In addition, a variety of modes of standardized information transmission between these domains can be employed, and this application demonstrates a mechanism that allows for the reliable and modular assembly of functioning synthetic hammerhead ribozyme switches and regulation of ribozyme activity in response to various effectors. In addition to demonstrating the first examples of small molecule-responsive, in vivo functional allosteric hammerhead ribozymes, this application describes a general approach for the construction of portable and scalable gene regulatory systems. The versatility of the platform in implementing application-specific control systems for small molecule-mediated regulation of cell growth and non-invasive in vivo sensing of metabolite production is described.

This application describes a framework for the reliable de novo construction of modular, portable, and scalable control systems that can be used to achieve flexible regulatory properties, such as up- and down-regulation of target expression levels and tuning of regulatory response to fit application-specific performance requirements, thereby expanding the utility of our platforms to a broader range of applications. For example, these switch platforms may be applied to the construction of transgenic regulatory control systems that are responsive to cell permeable, exogenous molecules of interest for a given network. In regulating sets of functional proteins, these switches can act to rewire information flow through cellular networks and reprogram cellular behavior in response to changes in the cellular environment. In regulating reporter proteins, ribozyme switches can serve as synthetic cellular sensors to monitor temporal and spatial fluctuations in the levels of diverse input molecules. The switch platforms described here represent powerful tools for constructing ligand-controlled gene regulatory systems tailored to respond to specific effector molecules and enable regulation of target genes in various living systems. Due to their general applicability, our platforms offer broad utility for applications in synthetic biology, biotechnology, and health and medicine.

II. Definitions

Hammerhead Ribozyme: A hammerhead ribozyme contains a core, three stems that extend from the core, referred to herein as stem I, stem II, and stem III, and at least one loop, which is located on the opposite end of a stems from the core. In embodiments where the ribozyme is a trans-acting ribozyme, it contains one loop, e.g., at the end of stem II, and is referred to as loop II. In embodiments of cis-acting ribozymes, the ribozyme contains two loops, one located at the end of stem I and is referred to as loop I, and the other located at the end of stem II and is referred to as loop II.

As used herein, a "cis-cleaving hammerhead ribozyme" is a hammerhead ribozyme that, prior to cleavage, is comprised of a single polynucleotide. A cis-cleaving hammerhead ribozyme is capable of cleaving itself.

As used herein, a "trans-cleaving hammerhead ribozyme" is a hammerhead ribozyme that, prior to cleavage, is comprised of at least two polynucleotides. One of the polynucleotides is the target sequence that is cleaved.

Complementary: Complementary refers to a nucleotide or nucleotide sequence that hybridizes to a given nucleotide or nucleotide sequence. For instance, for DNA, the nucleotide A is complementary to T and vice versa, and the nucleotide C is complementary to G and vice versa. For instance, in RNA, the nucleotide A is complementary to the nucleotide U and vice versa, and the nucleotide C is complementary to the nucleotide G and vice versa. Complementary nucleotides include those that undergo Watson and Crick base pairing and those that base pair in alternative modes. For instance, as used herein for RNA, the nucleotide G is complementary to the nucleotide U and vice versa, and the nucleotide A is complementary to the nucleotide G and vice versa. Therefore, in an RNA molecule, the complementary base pairs are A and U, G and C, G and U, and A and G. Other combinations, e.g., A and C or C and U, are considered to be non-complementary base pairs.

A complementary sequence is comprised of individual nucleotides that are complementary to the individual nucleotides of a given sequence, where the complementary nucleotides are ordered such that they will pair sequentially with the nucleotides of the given sequence. Such a complementary sequence is said to be the "complement" of the given sequence. For example, complements of the given sequence, 5'-ACUAGUC-3', include 3'-UGAUCAG-5' and 3'-UG-GACGG-3', among others. In the latter sequence, the third and sixth base pairs are both non-Watson and Crick G/U complementary base pairs.

Stem: A stem is a nucleic acid motif that extends from the ribozyme core, at least a portion of which is double-stranded. In certain embodiments, there is a loop at the opposite end of the stem from the ribozyme core, and this loop connects the two strands of the double-stranded stem. In certain embodiments, a stem comprises 2 to 20 complementary base pairs. In certain embodiments, a stem comprises 3, 4, 5, 6, 7, 8, or 9 complementary base pairs.

Stems are numbered according to where they extend from the core sequence. In certain embodiments, a hammerhead ribozyme contains three stems, which are referred to as stem I stem II, and stem III. In certain embodiments, stem I extends from the core between the sequence UCH and the sequence WYGANGA. In certain embodiments, stem II extends from the core between the sequence WYGANGA and the sequence GAAA. In certain embodiments, stem III extends from the core between the sequence GAAA and the sequence UCH. Thus, in certain embodiments, a ribozyme may be configured as follows: 5'-[first strand of stem III] UCH [first strand of stem I] . . . [second strand of stem I] WYGANGA [first strand of stem II] . . . [second strand of stem II] GAAA [second strand of stem III]-3'. The ellipses in this example represent loop sequences that connect the first and second strands of stem I and stem II.

In certain embodiments, at least 30% of the nucleotides in a stem are part of a complementary base pair. The remaining base pairs may be mismatched, non-complementary base pairs, or may be part of a bulge. In certain embodiments, at least 40% of the nucleotides in a stem are part of a complementary base pair. In certain embodiments, at least 50% of the nucleotides in a stem are part of a complementary base pair. In certain embodiments, at least 60% of the nucleotides in a stem are part of a complementary base pair. In certain embodiments, at least 70% of the nucleotides in a stem are part of a complementary base pair. In certain embodiments, at least 80% of the nucleotides in a stem are part of a complementary base pair. In certain embodiments, at least 90% of the nucleotides in a stem are part of a complementary base pair. In certain embodiments, at least 95% of the nucleotides in a stem are part of a complementary base pair. In certain embodiments, at least 99% of the nucleotides in a stem are part of a complementary base pair. In certain embodiments, 100% of the nucleotides in a stem are part of a complementary base pair.

Loop: A loop is a sequence of nucleotides that is not paired with another strand and is located at the distal end of a stem that is opposite the core. In certain embodiments, a loop is between 1 to 20 nucleotides long. In certain embodiments, a loop is between 2 and 10 nucleotides long. In certain embodiments, a loop is between 3 and 8 nucleotides long. The loop is numbered according to the stem to which it is attached. Therefore, loop I is located at the end of stem I opposite the core, loop II is located at the end of stem II opposite the core, and loop III is located at the end of stem III opposite the core.

As used herein, a "stem/loop" refers to the entire stem, along with any bulges within that stem, and the loop at the end of the stem. For example, stem/loop I includes stem I, including any bulges within stem I, and loop I. If a stem lacks a loop, then stem/loop refers to the stem, along with any bulges within that stem.

Bulge: As used herein, a "bulge" is a sequence of nucleotides that is not paired with another strand and is flanked on both sides by double-stranded nucleic acid sequences. In certain embodiments, a bulge is located within a stem. When a bulge is located within a stem, the nucleotides of the bulge are considered to be part of the stem. In certain embodiments, a hammerhead ribozyme comprises more than one bulge. In certain embodiments, a bulge within a stem is located two base pairs from the core. In certain embodiments, one or both strands of the stem contain a bulge.

Directly Coupled: As used herein, an information transmission domain is directly coupled to a loop of a ribozyme where the loop, relative to active ribozyme structure in the absence of the aptamer, is interrupted at one only backbone phosphodiester bond between two residues of the loop, the backbone phosphodiester bond being replaced with phosphodiester bonds to the 5' and 3' ends of the aptamer. In the active form of the aptamer-regulated ribozyme, the 5' and 3' residues of the information transmission domain are based paired to one another to form a duplex region in order to preserve the structure of the otherwise interrupted loop.

Nucleotide: Refers to naturally- and non-naturally-occurring nucleotides and nucleotide analogs. Nucleotides include, but are not limited to, adenosine, cytosine, guanosine, thymidine, uracil, 4-acetylcytosine, 8-hydroxy-N-6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine and 2,6-diaminopurine.

Nucleic Acid: "nucleic acid sequence," "nucleic acid molecule," and "polynucleotide" refer to a DNA sequence or analog thereof, or an RNA sequence or analog thereof. Nucleic acids are formed from nucleotides, including, but not limited to, the nucleotides listed above.

Low $Mg^{2+}$: Refers to a concentration of less than about 1 mM. In certain embodiments, the $Mg^{2+}$ concentration is less than about 0.5 mM $Mg^{2+}$. In certain embodiments, the $Mg^{2+}$ concentration is less than about 0.1 mM $Mg^{2+}$.

Actuator Domain: A switch domain that encodes the system control function. As used here, the actuator domain encodes the gene regulatory function and is comprised of a hammerhead ribozyme sequence.

Communication Module: A sequence element that typically forms an imperfectly paired double-stranded stem that can adopt different base pairs between nucleotides through a 'slip-structure' mechanism. As used here, a communication module is a type of information transmission domain that transmits the binding state of the aptamer domain to the adjacent actuator domain through a helix slipping mechanism. As demonstrated in this work, a communication module does not act in a modular fashion with other switch domains. The term is retained here from earlier work in the field of nucleic acid engineering.

Competing Strand: The nucleic acid sequence within a strand displacement domain that is bound to the general transmission region of the switch when the sensor domain is in the restored conformation (i.e., in the presence of ligand). The competing strand competes for binding with the switching strand, which is initially bound to this transmission region in the absence of ligand.

Component: A part of a system that encodes a distinct activity or function.

Composability: A property of a system that indicates its ability to be comprised of components that can be selected and assembled in a modular fashion to achieve a desired system performance. As used here, composability refers to the ability of the individual domains of the control system to be modularly linked without disrupting their activities.

Helix Slipping Domain: A subset of information transmission domains that act through a helix slipping mechanism. The helix slipping domain is also referred to as the communication module.

Helix Slipping Mechanism: An information transmission mechanism that is based on an information transmission domain that functions through a helix slipping event and does not allow for rational design. Such a helix slipping event utilizes a communication module (or helix slipping domain) within the general transmission region of the switch (the base stem of the aptamer) to result in disruption or restoration of the actuator domain in response to restoration of the sensor domain.

Information Transmission Domain: A switch domain that encodes the function of transmitting information between the sensor domain and the actuator domain.

Information Transmission Mechanism: A general mechanism for transmitting information between the sensor domain and the actuator domain of a switch. As used here, this mechanism regulates the activity of the actuator domain in response to the binding state of the sensor domain.

Ligand: "Ligand" or "analyte" or grammatical equivalents herein is meant to refer to any molecule or compound to be detected and that can interact with an aptamer to be designed and/or selected as described here. Suitable ligands or analytes include, but are not limited to, small chemical molecules such as environmental or clinical chemicals, pollutants or biomolecules, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including prokaryotic (such as pathogenic bacteria) and eukaryotic cells, including mammalian tumor cells), viruses, spores, etc. Illustrative analytes that are proteins include, but are not limited to, enzymes; drugs; cells; antibodies; antigens; cellular membrane antigens and receptors (neural, hormonal, nutrient, and cell surface receptors) or their natural ligands.

Modular: A property of a system comprised of modules, which indicates that the modules can by interchanged as parts without changing the interface between modules or the modules themselves.

Portability: A property of a system that indicates its ability to be implemented in environments different from that which it was originally designed. As used here, portability refers to the ability of the control system to be implemented in different organisms.

Scalability: A property of a system that indicates its ability to handle increasing work. As used here, scalability refers to the ability of the control system to be implemented across broad application space by being able to forward design its response to different molecular information.

Switch: A molecule that can adopt at least two different conformational states, where each state is associated with a different activity of the molecule. Often a ligand can bind to one or more conformations of the switch, such that the presence of the ligand shifts the equilibrium distribution across the adoptable conformations and therefore regulates the activity of the switch molecule. As used here, switch refers to an RNA molecule that can adopt different structures that correspond to different gene regulatory activities. An RNA switch is then a ligand-controlled gene regulatory system.

Switch Domain: A component of a switch that encodes a distinct activity or function.

Switching Strand: The nucleic acid sequence within a strand displacement domain that is bound to the general transmission region of the switch when the sensor domain is in the disrupted conformation (i.e., in the absence of ligand). The switching strand is displaced by the competing strand in the presence of ligand.

Sensor Domain: A switch domain that encodes a ligand binding function. As used here, the sensor domain is comprised of an RNA aptamer sequence.

Strand Displacement Domain: A subset of information transmission domains that act through a strand displacement mechanism.

Strand Displacement Mechanism: An information transmission mechanism that is based on the rational design of an information transmission domain that functions through a strand displacement event. Such a strand displacement event utilizes competitive binding of two nucleic acid sequences (the competing strand and the switching strand) to a general transmission region of the switch (the base stem of the aptamer) to result in disruption or restoration of the actuator domain in response to restoration of the sensor domain.

III. Exemplary Embodiments

The hammerhead ribozyme (hRz) is an RNA motif which is capable of sustaining either in trans or in cis cleavage of a phosphodiester bond. The cis-acting hammerhead ribozyme (chRz) is a catalytic RNA that undergoes self-cleavage of its own backbone to produce two RNA products. Cis-acting hammerhead ribozymes contain three base-paired stems and a highly conserved core of residues required for cleavage. The cleavage reaction proceeds by an attack of a 2' hydroxyl oxygen of a catalytic site cytosine on the phosphorus atom attached to the 3' carbon of the same residue. This breaks the sugar phosphate backbone and produces a 2',3' cyclic phosphate.

The minimal hammerhead sequence that is required for the self-cleavage reaction includes approximately 13 conserved or invariant "core" nucleotides, most of which are not involved in forming canonical Watson-Crick base-pairs. The core region is flanked by stems I, II and III, which are in general comprised of canonical Watson-Crick base-pairs but are otherwise not constrained with respect to sequence.

Cleavage specificity of the trans-acting hammerhead ribozyme (thRz) is controlled by the hybridizing arms of the ribozyme, which anneal with the substrate in a complementary fashion and direct cleavage of the scissile phosphodiester bond. This activity is specifically directed to occur after the third nucleotide of the cleavage triplet.

The present invention provides aptamer-regulated trans-acting hammerhead ribozymes and aptamer-regulated cis-acting hammerhead ribozymes. The subject aptamer-regulated thRzs and chRzs are a versatile class of ribozymes that can be readily engineered to be responsive to a variety of ligands, and are useful in many applications. For example, aptamer-regulated thRzs and chRzs can be designed to modulate the activity of targeted genes in a ligand-dependent manner, and are therefore useful for modulating the expression of endogenous or heterologous genes.

The ribozyme domain (also herein the effector domain) can have at least two conformational states, an "off" state and an "on" state, that is defined by its activity level (reaction rate, for example) for either undergoing self-cleavage in the case of chRzs, or cleaving a target sequence in the case of thRzs. The effector domains of the invention can be switched between their "on" and "off" conformational states in response to ligand binding to the aptamer domain. Aptamer-regulated ribozymes of the invention, therefore, act as a switch whose activity is turned "on" and "off" in response to ligand binding. In certain embodiments, the ribozyme domain's function is starkly dependent on the presence or absence of the ligand, or can show a more dose-response like dependency on concentration of the ligand available to bind to the aptamer domain.

The choice of ligand to which the aptamer binds, and the ribozyme therefore is regulated by, are vast. In certain instances, the ligand is a small molecule having a molecular weight less than 2500 amu.

These can be naturally or non-naturally occurring molecules, including peptides, small organic molecules (including drugs and certain metabolites and intermediates, cofactors, etc), and metal ions merely to illustrate. Exemplary ligands that bind to an aptamer include, without limitation, small molecules, such as drugs, metabolites, intermediates, cofactors, transition state analogs, ions, metals, nucleic acids, and toxins. Aptamers may also bind natural and synthetic polymers, including proteins, peptides, nucleic acids, polysaccharides, glycoproteins, hormones, receptors and cell surfaces such as cell walls and cell membranes. The binding of a ligand to an aptamer, which is typically RNA, alters the base-pairing with the information transmission domain that is carried over as a structural change in the ribozyme domain and alters its ability to mediate cleavage of a phosphodiester bond (either self-cleavage or cleavage of a target sequence). Therefore, ligand binding affects the effector domain's ability to mediate gene inactivation, transcription, translation, or otherwise interfere with the normal activity of the target gene or mRNA, for example. An aptamer will most typically have been obtained by in vitro selection for binding of a target molecule. However, in vivo selection of an aptamer is also possible. Aptamers have specific binding regions which are capable of forming complexes with an intended target molecule in an environment wherein other substances in the same environment are not complexed to the nucleic acid. The specificity of the binding is defined in terms of the comparative dissociation constants ($K_d$) of the aptamer for its ligand as compared to the dissociation constant of the aptamer for other materials in the environment or unrelated molecules in general. A ligand is one which binds to the aptamer with greater affinity than to unrelated material. Typically, the $K_d$ for the aptamer with respect to its ligand will be at least about 10-fold less than the $K_d$ for the aptamer with unrelated material or accompanying material in the environment. Even more preferably, the $K_d$ will be at least about 50-fold less, more preferably at least about 100-fold less, and most preferably at least about 200-fold less. An aptamer will typically be between about 10 and about 300 nucleotides in length. More commonly, an aptamer will be between about 30 and about 100 nucleotides in length.

Aptamers are readily made that bind to a wide variety of molecules. Each of these molecules can be used as a modulator of the associated ribozyme using the methods of the invention. For example, organic molecules, nucleotides, amino acids, polypeptides, target features on cell surfaces, ions, metals, salts, saccharides, have all been shown to be suitable for isolating aptamers that can specifically bind to the respective ligand. For instance, organic dyes such as Hoechst 33258 have been successfully used as target ligands for in vitro aptamer selections (Werstuck and Green, Science 282: 296-298 (1998)). Other small organic molecules like dopamine, theophylline, sulforhodamine B, and cellobiose have also been used as ligands in the isolation of aptamers. Aptamers have also been isolated for antibiotics such as kanamycin A, lividomycin, tobramycin, neomycin B, viomycin, chloramphenicol and streptomycin. For a review of aptamers that recognize small molecules, see Famulok, Science 9:324-9 (1999).

In certain embodiments, the ligand of the aptamer of an aptamer-regulated ribozyme of the invention is a cell-permeable, small organic molecule. Small organic molecules which do not have a general inhibitory effect on translation are preferred as ligands. The small molecule preferably also exhibits in vivo persistence sufficient for achieving the desired level of inhibition of translation. The molecules also can be screened to identify those that are bioavailable after, for example, oral administration. In certain embodiments of the invention, the ligand is nontoxic. The ligand may optionally be a drug, including, for example, a steroid. However, in some of the methods of controlling gene expression, it is preferable that the ligand be pharmacologically inert. In some embodiments, the ligand is a polypeptide whose presence in the cell is indicative of a disease or pathological condition. In other embodiments, the ligand for an aptamer is an antibiotic, such as chloramphenicol. In an alternative embodiment, the ligand of the aptamer is an organic dye such as Hoeschst dye 33258. In still another embodiment, the ligand may be a metal ion. In a specific embodiment, the aptamer domain of an aptamer-regulated nucleic acid responds to binding to caffeine.

Aptamers are typically developed to bind particular ligands by employing known in vivo or in vitro (most typically, in vitro) selection techniques known as SELEX (Ellington et al., Nature 346, 818-22 (1990); and Tuerk et al., Science 249, 505-10 (1990)). Methods of making aptamers are also described in, for example, U.S. Pat. No. 5,582,981, PCT Publication No. WO 00/20040, U.S. Pat. No. 5,270,163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291.

Generally, in their most basic form, in vitro selection techniques for identifying aptamers involve first preparing a large pool of oligonucleotides of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques, although any means that will allow faithful, efficient amplification of selected nucleic acid sequences can be employed. The DNA pool is then in vitro transcribed to produce RNA transcripts. The RNA transcripts may then be subjected to affinity chromatography, although any protocol which will allow selection of nucleic acids based on their ability to bind specifically to another molecule (e.g., a protein or any target molecule) may be used. In the case of affinity chromatography, the transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand. Once an aptamer sequence has been successfully identified, the aptamer may be further optimized by performing additional rounds of selection starting from a pool of oligonucleotides comprising the mutagenized aptamer sequence. For use in the present invention, the aptamer is preferably selected for ligand binding in the presence of salt concentrations and temperatures which mimic normal physiological conditions.

One can generally choose a suitable ligand without reference to whether an aptamer is yet available. In most cases, an aptamer can be obtained which binds the ligand of choice by someone of ordinary skill in the art. The unique nature of the in vitro selection process allows for the isolation of a suitable aptamer that binds a desired ligand despite a complete dearth of prior knowledge as to what type of structure might bind the desired ligand.

For an aptamer to be suitable for use in the present invention, the binding affinity of the aptamer for the ligand must be sufficiently strong and the structure formed by the aptamer when bound to its ligand must be significant enough so as to switch an aptamer-regulated ribozyme of the invention between "on" and "off" states or tune the functional level of an aptamer-regulated ribozyme.

The association constant for the aptamer and associated ligand is preferably such that the ligand functions to bind to the aptamer and have the desired effect at the concentration of ligand obtained upon administration of the ligand. For in vivo use, for example, the association constant should be such that binding occurs well below the concentration of ligand that can be achieved in the serum or other tissue. Preferably, the required ligand concentration for in vivo use is also below that which could have undesired effects on the organism.

Accordingly, certain embodiments provide methods of designing and selecting aptamers or aptamer domains that are responsive to one or more pre-selected or pre-determined ligands. The subject aptamer-regulated ribozymes may also be "tuned" so that their switching behavior is more or less responsive to ligand binding. Aptamer-regulated ribozymes may also be "tuned" so that the binding affinity of the aptamer domain is more or less sensitive to its ligand. For instance, the thermodynamic properties of intramolecular duplex formation and other 2° and 3° structures in the aptamer-regulated ribozymes may be altered so that the aptamer domain is more or less amenable to ligand binding, i.e., such as may be manifest in the dissociation constant ($K_d$) or other kinetic parameters (such as $K_{on}$ and $K_{off}$ rates). Alternatively, allosteric changes in the ribozyme domain may be more or less responsive to ligand binding upon alterations in hybridization and other intramolecular interactions that may effect 2° and 3° structures of the ribozyme domain. Forward engineering strategies for altering the thermodynamic properties of nucleic acid structures are well known in the art. For instance, increased complementary nucleic acid pairing may increase the stability of a ribozyme domain or aptamer domain.

EXAMPLE 1

Generation of Modular and Scalable Aptamer-Regulated Cis-Ribozymes

To satisfy the engineering design principle of scalability (DP1) we chose RNA aptamers (11), nucleic acid ligand-binding molecules, as the sensing platform for the universal control system. Our choice of sensing platform was driven by the proven versatility of RNA aptamers. Standard in vitro selection strategies or SELEX (12, 13) have been used to generate RNA aptamers de novo to a wide variety of ligands, including small molecules, peptides, and proteins (14). In addition, the specificity and affinity of an aptamer can be tuned through the selection process to meet the specific performance requirements of a given application. The continued selection of new aptamers to appropriate cellular molecules that function under in vivo conditions will enable these elements to be implemented as sensors in RNA-based control systems.

To satisfy the engineering design principle of portability (DP2) we chose the hammerhead ribozyme, a catalytic RNA, as the regulatory element in the universal control system. Our choice of regulatory element was driven by the ability of the hammerhead ribozyme to exhibit self-cleavage activity across various organisms and its demonstrated potential in biomedical and biotechnological applications owing to its small size, relative ease of design, and rapid kinetics (15). The utility of hammerhead ribozymes as gene regulatory elements has been demonstrated in various systems (16-18). In addition, several research groups have engineered a special class of synthetic hammerhead ribozymes referred to as allosteric hammerhead ribozymes that contain separate catalytic and ligand-binding domains, which interact in a ligand-dependent manner to control the activity of the ribozyme (19-22). While this class of ribozymes enables a better control system due to the presence of the integrated ligand-binding domain, there has been no success in translating them to in vivo environments.

Figure 1B:
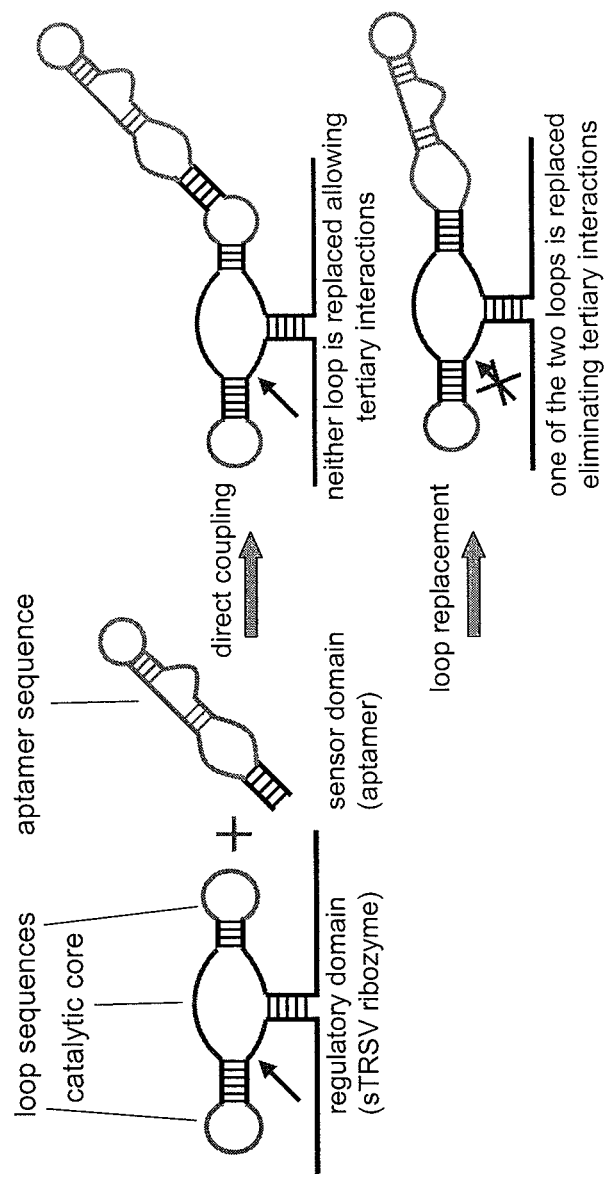

Design Strategies for Engineering Portability, Utility, and Composability into a Biological Control System To support a framework for engineering ligand-controlled gene regulatory systems, we specified a design strategy that is in accordance with our engineering principles stated above (FIG. 1A, B). This strategy is comprised of three components that address mechanisms for the portability (DP2), utility (DP3), and composability (DP4) of the control system and are critical to the development of a general ribozyme switch platform. First, the cis-acting hammerhead ribozyme constructs are integrated into the flexible regulatory space of the 3' UTR (FIG. 1A). We chose to locate the synthetic ribozymes within the 3' UTR of their target gene as opposed to the 5' UTR in order to isolate their specific cleavage effects on transcript levels from their non-specific structural effects on translation initiation, as secondary structures have been demonstrated to repress efficient translation when placed in the 5' UTR (23; K. Hawkins and C.D.S., unpublished observations). In addition, cleavage within the 3' UTR is a universal mechanism for transcript destabilization in eukaryotic and prokaryotic organisms. Second, each ribozyme construct is insulated from surrounding sequences, which may disrupt its structure and therefore its activity, by incorporating spacer sequences immediately 5' and 3' of stem III (FIG. 1A). By implementing these two components, we ensure that these control systems will be portable across organisms and modular to coupling with different coding regions. The third component was necessitated by the fact that previous engineered in vitro allosteric ribozyme systems, which replace stem loops I or II with part of the aptamer domain (FIG. 1B, lower right), do not function in vivo. From previous studies on the satellite RNA of tobacco ringspot virus (sTRSV) hammerhead ribozyme (17), we suspect that this lack of in vivo functionality in earlier designs results from removal of stem loop sequences that may play a critical role in tertiary interactions that stabilize the catalytically active conformation under physiological $Mg^{2+}$ concentrations. To develop ribozyme switches that function in vivo, we chose to integrate the hammerhead ribozyme into the target transcript through stem III and couple the sensor domain directly to the ribozyme through stem loops I or II to maintain these potentially essential sequence elements (FIG. 1B, upper right). Construction and characterization of the regulatory activity of a series of ribozyme control constructs in the eukaryotic model organism Saccharomyces cerevisiae (FIG. 1A) indicate that maintenance of loop I and II sequences and thus integration through stem III are essential for their in vivo functionality (Example 2, FIG. 7).

Engineering Mechanisms for Information Transmission Between the Modular Switch Domains The final design challenge in building a universal switch platform is to develop a standardized means of transmitting information (encoded within an information transmission domain) from the sensor (aptamer) domain to the regulatory (ribozyme) domain (DP5). There are two different strategies for transmitting information between the aptamer and ribozyme domains: strand displacement and helix slipping. We constructed and characterized ribozyme switch platforms based on both mechanisms.

Figure 2A:
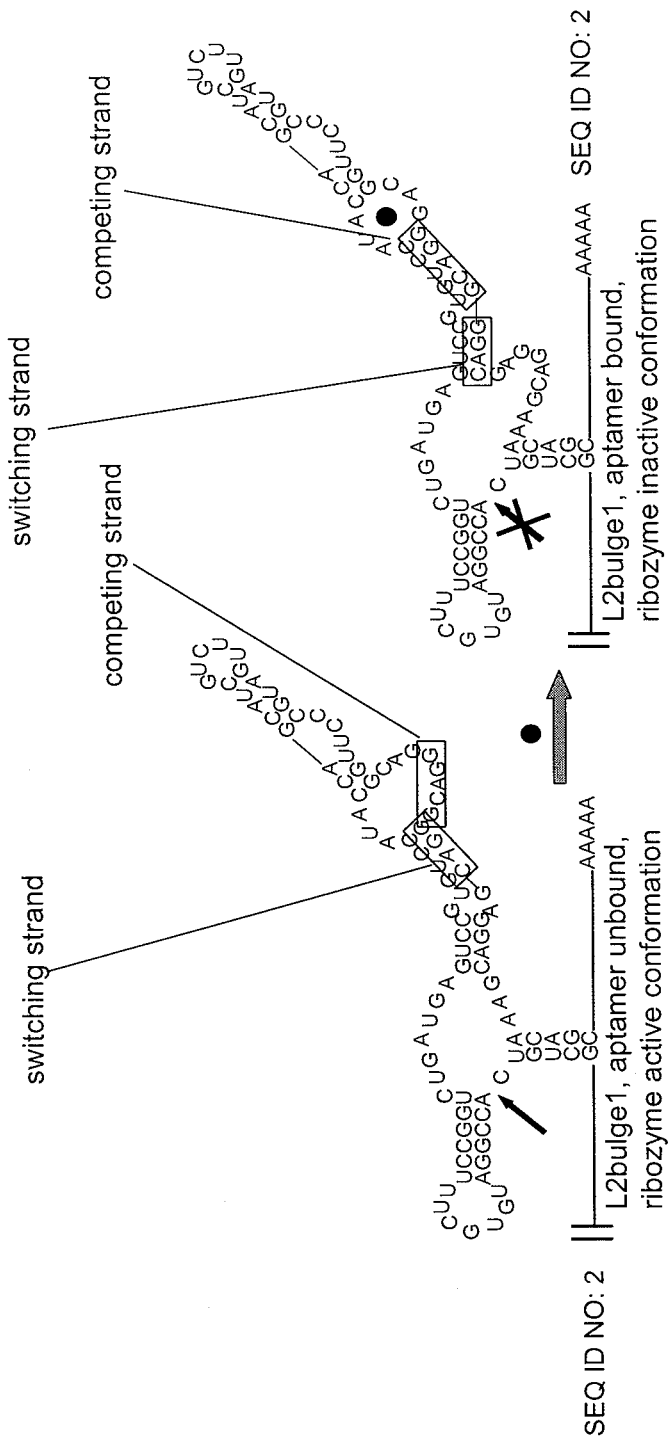
FIG. 2. Regulatory properties of the strand displacement information transmission mechanism. (A) Gene expression 'ON' ribozyme switch platform, L2bulge1. (B) Gene expression 'OFF' ribozyme switch platform, L2bulgeOff1. The theophylline-dependent gene regulatory behavior of (C) L2bulge1 ('ON' switch), (D) L2bulgeOff1 ('OFF' switch), and L2Theo (non-switch control). Gene expression levels are reported in fold as defined in Example 2 and normalized to the expression levels in the absence of effector.
Figure 2B:
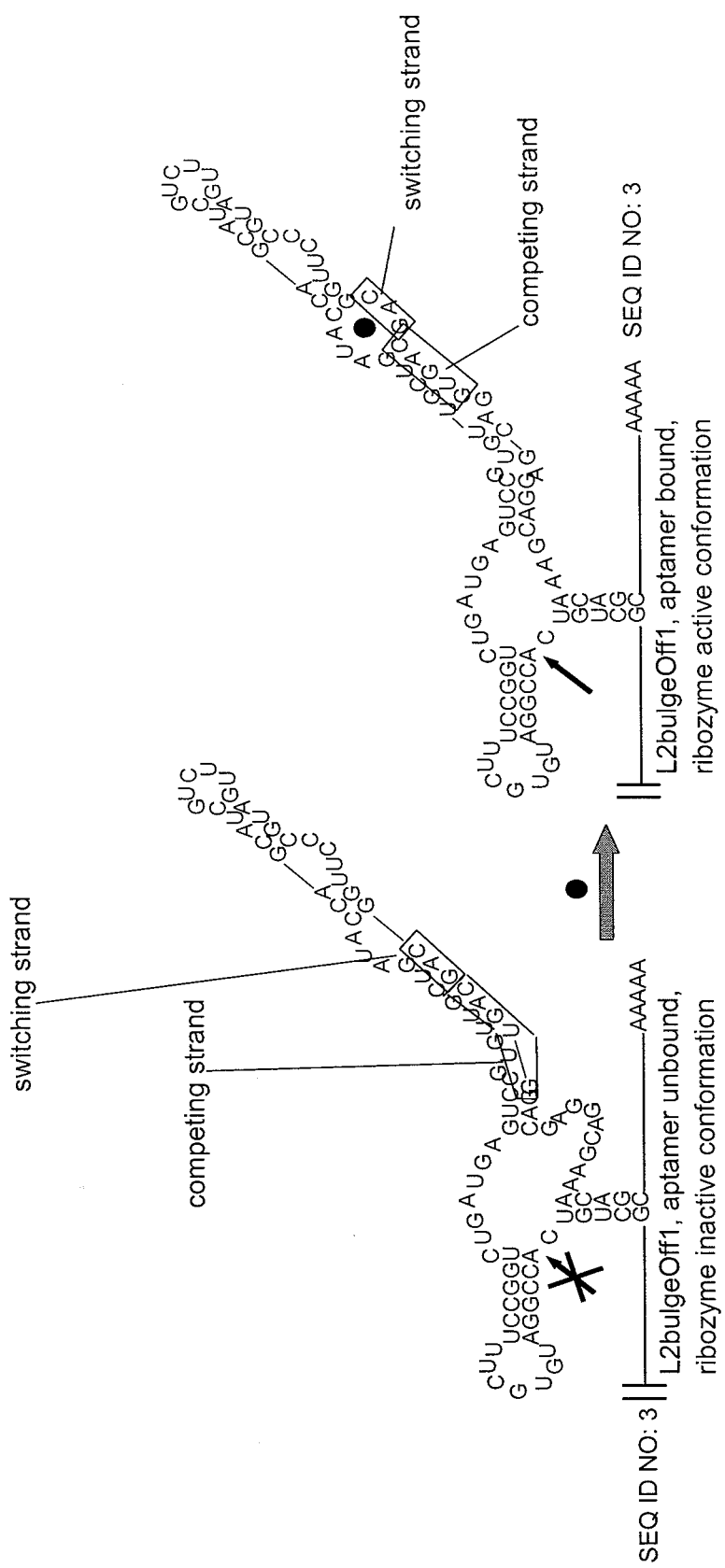
Figure 2C:
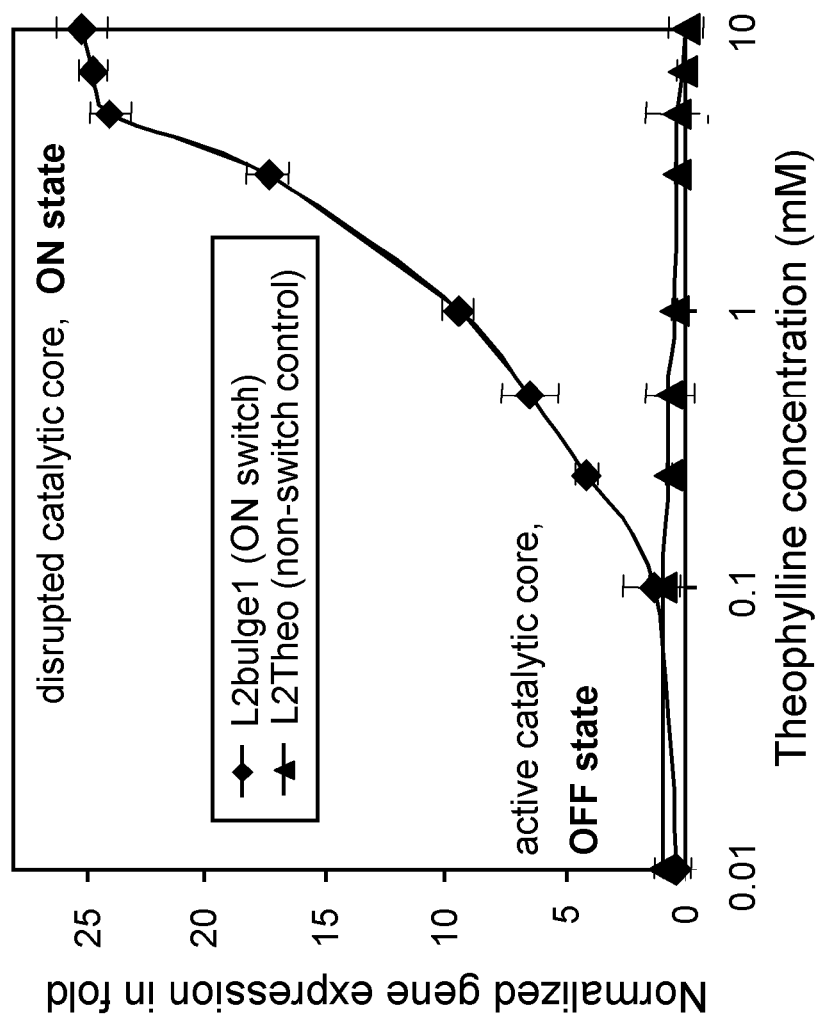
Figure 2D:
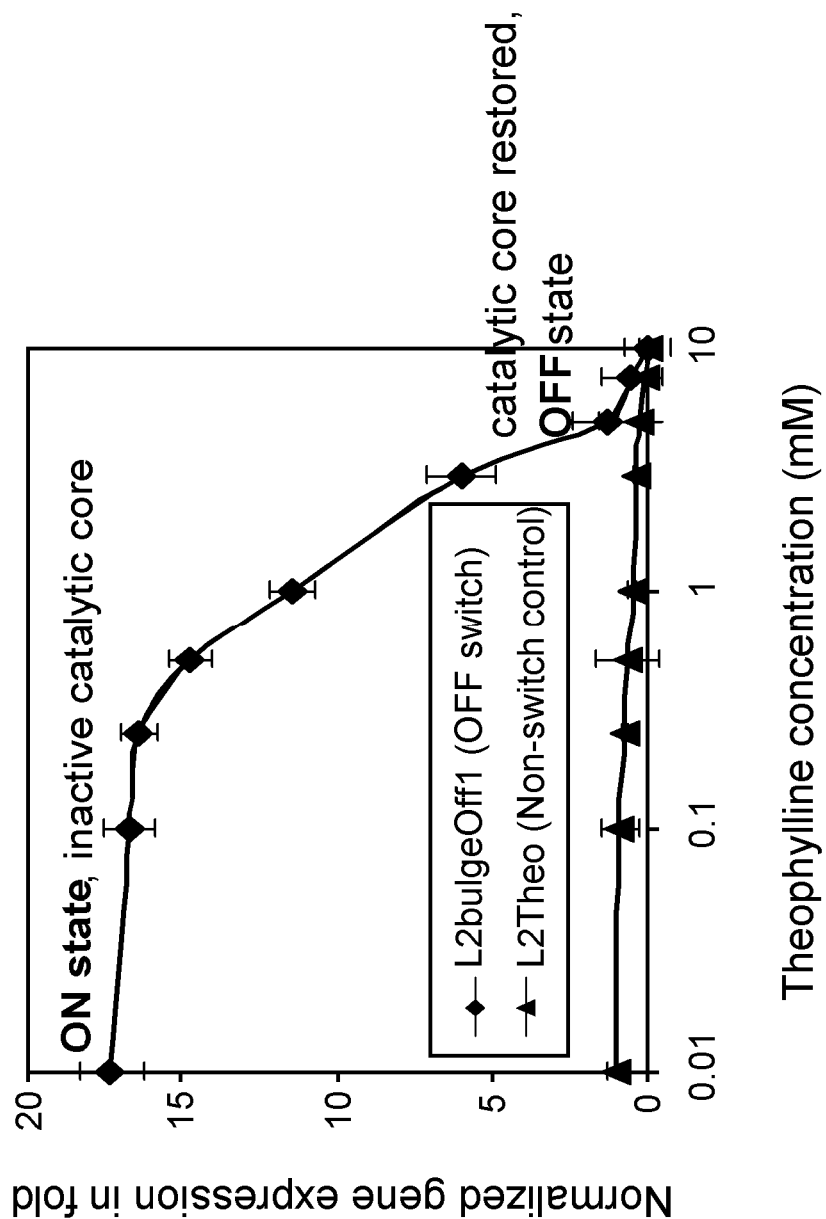
Figure 8:
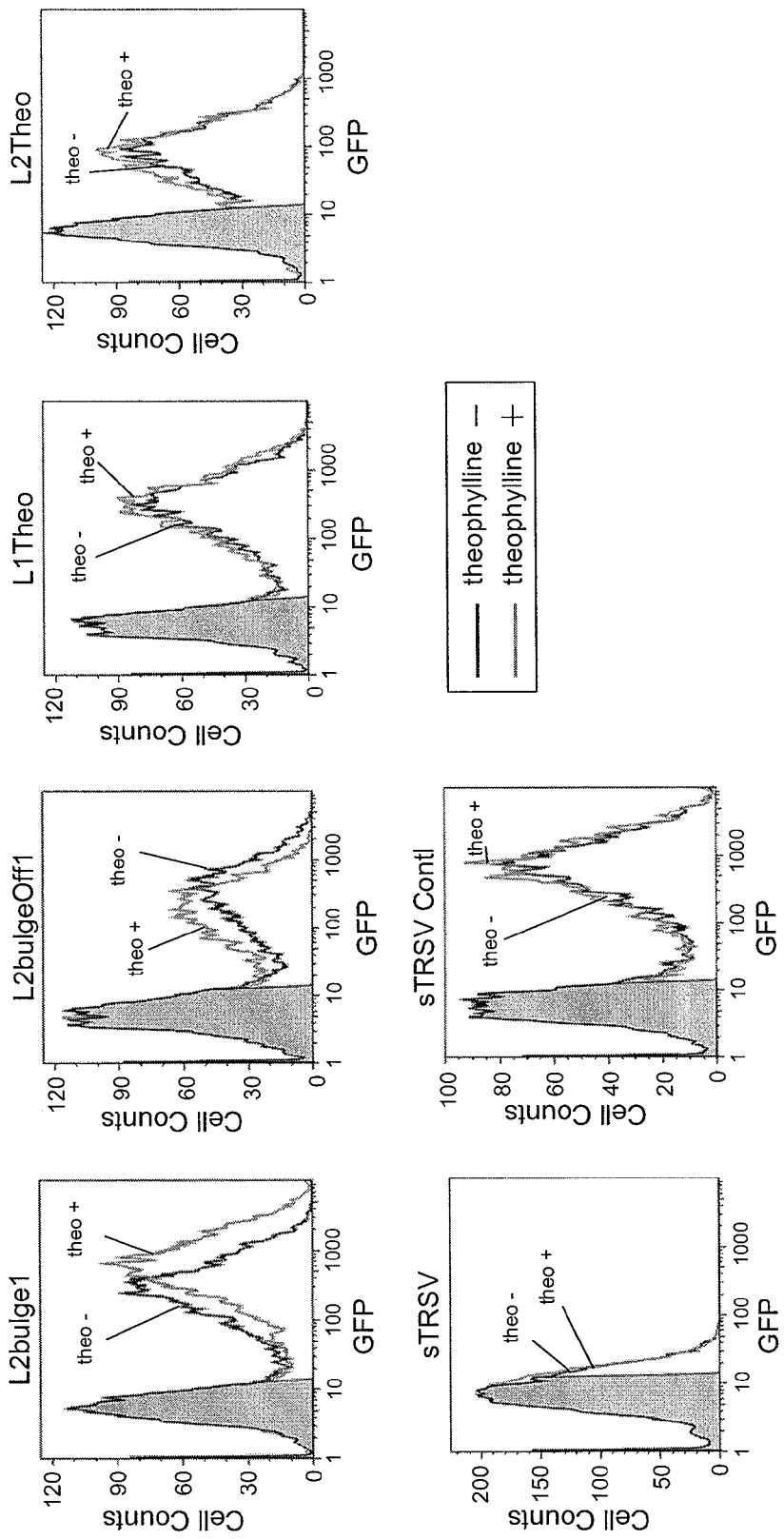
FIG. 8. Flow cytometry histograms of L2bulge1, L2bulgeOff1, and the ribozyme control cell populations grown in the presence (+) and absence (−) of 5 mM theophylline. Dark gray line: cell populations grown in the absence of theophylline; light gray line: cell populations grown in 5 mM theophylline; shaded population: cell populations indicative of the non-induced cell population, shaded here to indicate the portion of cells in the population that have lost the plasmid and exhibit non-induced, or background, levels of autofluorescence. Histograms are representative of three independent experiments.

The first information transmission domain that we developed is based on a strand displacement mechanism, which involves the rational design of two sequences that compete for binding to a general transmission region (the base stem of the aptamer) (FIG. 2A, B). We employed this mechanism in engineering a ribozyme switch platform that enables both up- and down-regulation of gene expression in response to increasing effector concentrations ('ON' and 'OFF' switches, respectively). An initial ribozyme switch, L2bulge1, was constructed to up-regulate gene expression through the corresponding base platform (L2Theo, FIG. 7C) by incorporating a competing strand following the 3' end of the theophylline aptamer (24) (FIG. 2A). This competing strand is perfectly complementary to the base stem of the aptamer at the 5' end. Using the same design principles, we engineered another ribozyme switch, L2bulgeOff1 (FIG. 2B), for down-regulating gene expression. Our strand displacement strategy is based on the conformational dynamics characteristic of RNA molecules that enables them to distribute between at least two different conformations at equilibrium: one conformation in which the competing strand is not base-paired or base-paired such that the ligand-binding pocket is not formed, and the other conformation in which the competing strand is base-paired with the aptamer base stem, displacing the switching strand and thus allowing the formation of the ligand-binding pocket. Strand displacement results in the disruption (L2bulge1) or restoration (L2bulgeOff1) of the ribozyme's catalytic core. Binding of theophylline to the latter conformation shifts the equilibrium distribution to favor the aptamer-bound form as a function of increasing theophylline concentration. An increase in target expression levels (induction in fold 25) at 5 mM theophylline relative to those in the absence of effector was observed in L2bulge1 (FIG. 2C and FIG. 8). In contrast, a reduction in expression levels (reduction in fold 18) at 5 mM theophylline relative to those in the absence of effector was observed in L2bulgeOff1 (FIG. 2D and FIG. 8). Through our strand displacement mechanism, we have engineered ribozyme switches de novo that provide allosteric regulation of gene expression and function as 'ON' and 'OFF' switches.

Figure 3A:
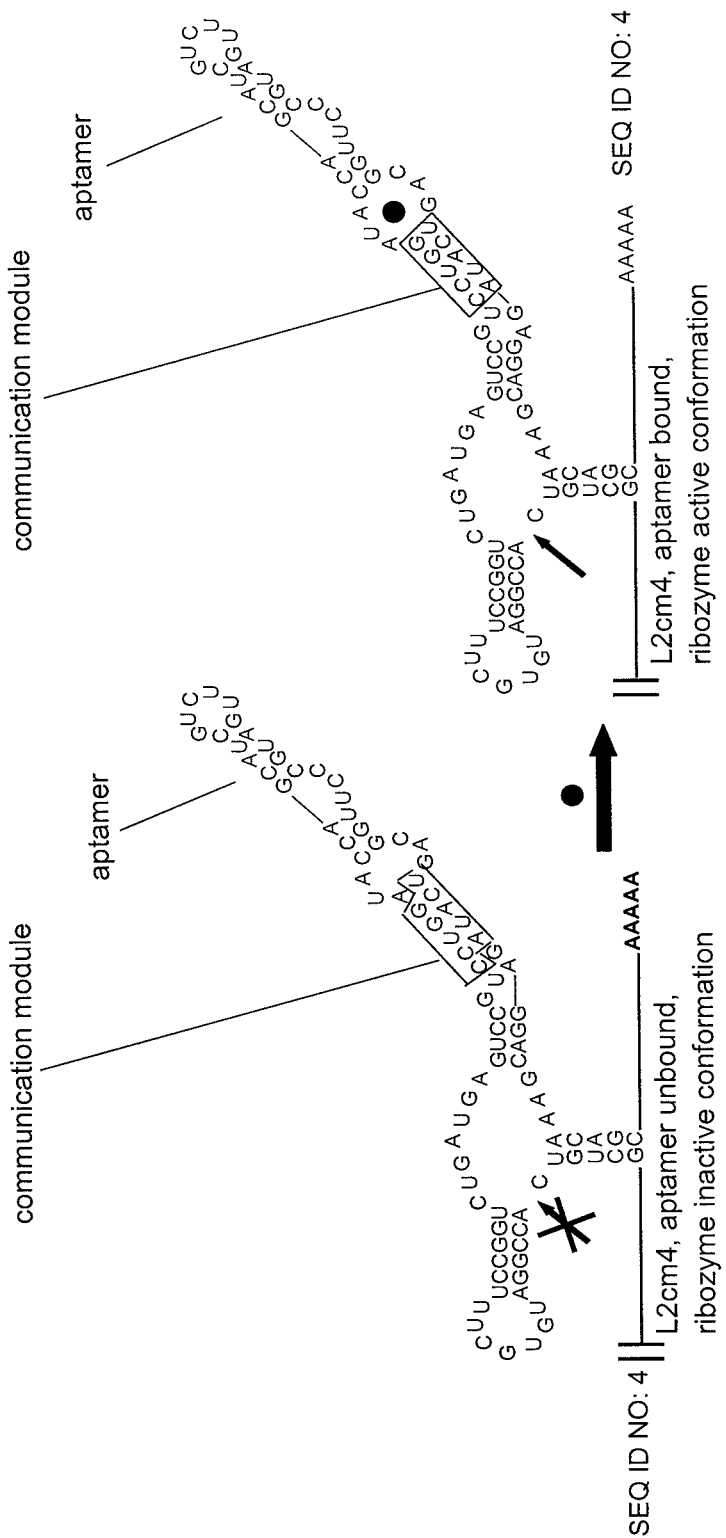
FIG. 3. Regulatory properties of the helix slipping information transmission mechanism. (A) Gene expression 'OFF' ribozyme switch platform based on helix slipping, L2 cm4. The base stem of the aptamer is replaced with a communication module. (B) Regulatory activities of helix slipping-based ribozyme switches. Gene regulatory effects of the 'OFF' switches at 5 mM theophylline are reported in fold repression relative to expression levels in the absence of effector. The corresponding communication module sequences are indicated. Gene expression levels are reported as described in FIG. 2.
Figure 3B:
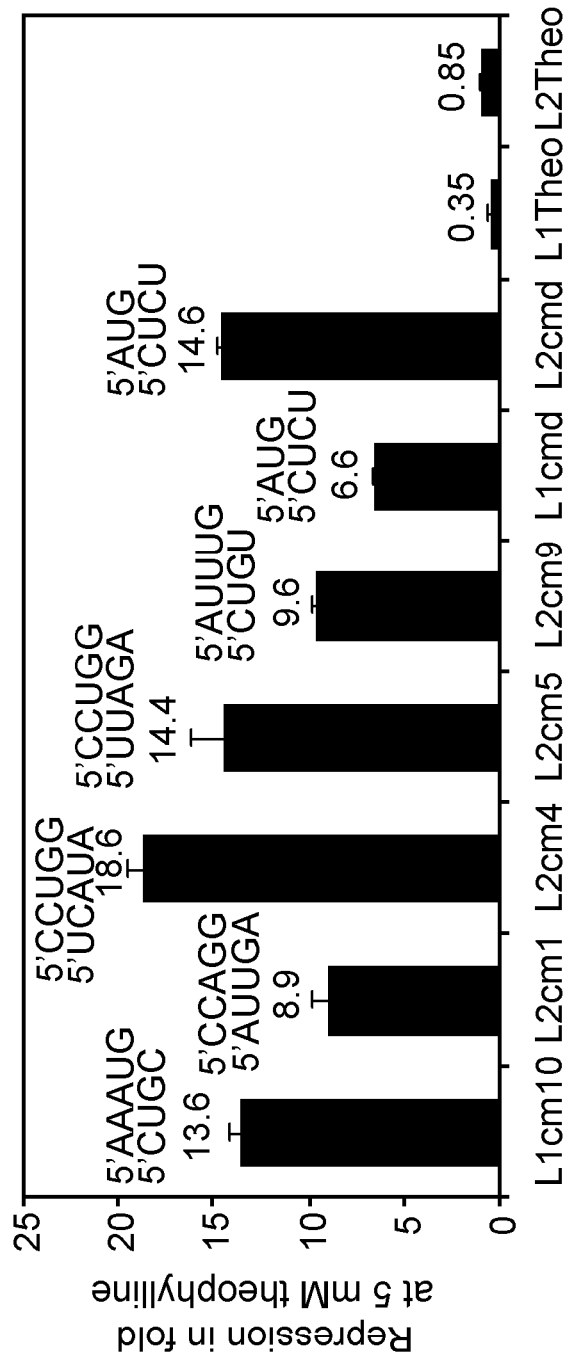
Figure 9:
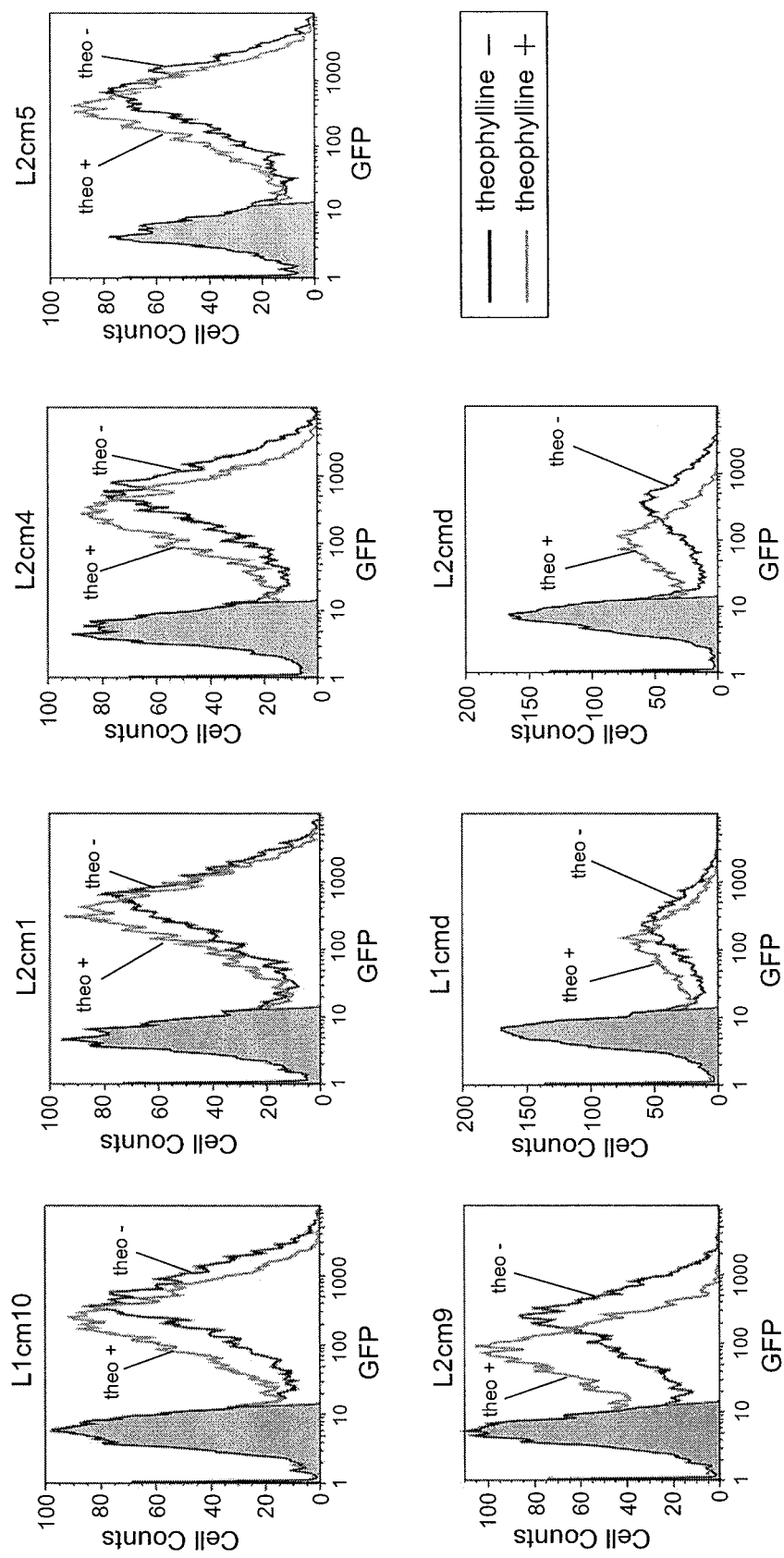
FIG. 9. Flow cytometry histograms of the helix slipping-based ribozyme switch cell populations grown in the presence (+) and absence (−) of 5 mM theophylline. Population data is measured and reported as described in FIG. 8. Histograms are representative of three independent experiments.
Figure 11:
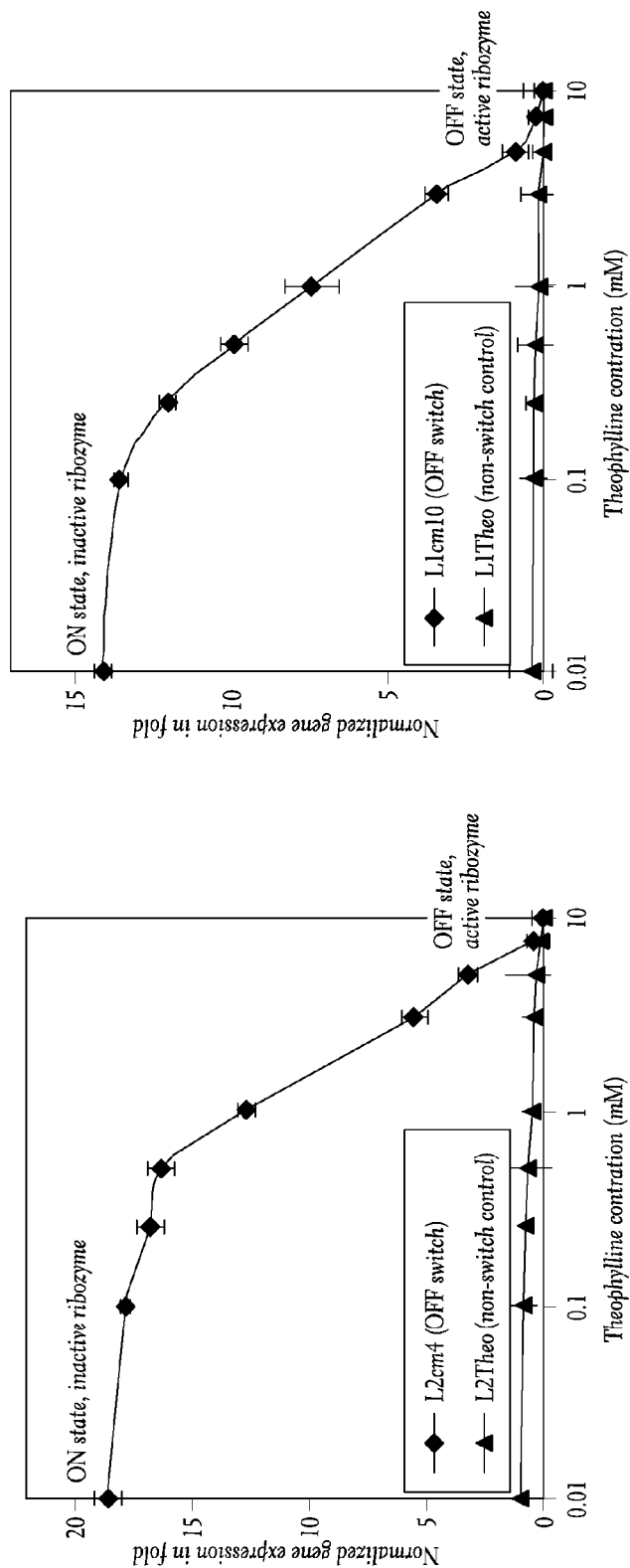
FIG. 11. Regulatory properties of the helix slipping information transmission mechanism. The theophylline-dependent gene regulatory behavior of L2 cm4 and L1cm10. Gene expression levels are reported as described in FIG. 2, except that L1 Theo is used as a non-switch control for L1cm10.

We engineered a second ribozyme switch platform to examine an alternative information transmission domain based on a helix slipping mechanism, which does not allow for rational design (FIG. 3A). This mechanism involves the functional screening of 'communication modules' (20-22) within the base stem of the aptamer. Communication modules are dynamic elements capable of transmitting the binding state of an aptamer domain to an adjacent regulatory domain through a 'slip-structure' mechanism (20), in which a nucleotide shift event is translated to a small-scale change in the conformation of the regulatory domain in a ligand-dependent manner. These elements have been developed through in vitro screening processes, and their communicative properties have been demonstrated in vitro in engineered allosteric ribozymes (19-22). We screened the in vivo functionality of previously in vitro selected communication modules (20-22) by assaying the activity of these sequences within L1 Theo and L2Theo. A critical difference between the design of the previously developed in vitro allosteric ribozymes, from which these communication modules were generated, and that of our engineered ribozyme switches is the coupling strategies between the aptamer and ribozyme domains and their effects on the in vivo activity of the ribozyme domain as described previously (FIG. 1B). Among the thirteen communication modules (20-22) screened for in vivo activity, five (cm1, cm4, cm5, cm9, and cmd) exhibit down-regulation of expression levels through loop II, whereas only two (cm10 and cmd) exhibit such regulation through loop I (FIG. 3B). The regulatory activities of two helix slipping-based ribozyme switches, L2 cm4 and L1cm10 (FIGS. 9, 11), were characterized across a range of theophylline concentrations and exhibit substantial regulatory effects. Although the helix slipping constructs are comprised of identical aptamer and catalytic core sequences, they exhibit different extents of regulation. This variability suggests that each construct contains a different equilibrium distribution between the adoptable conformations and that the energy required for structural switching between the conformations is also different.

Figure 12:
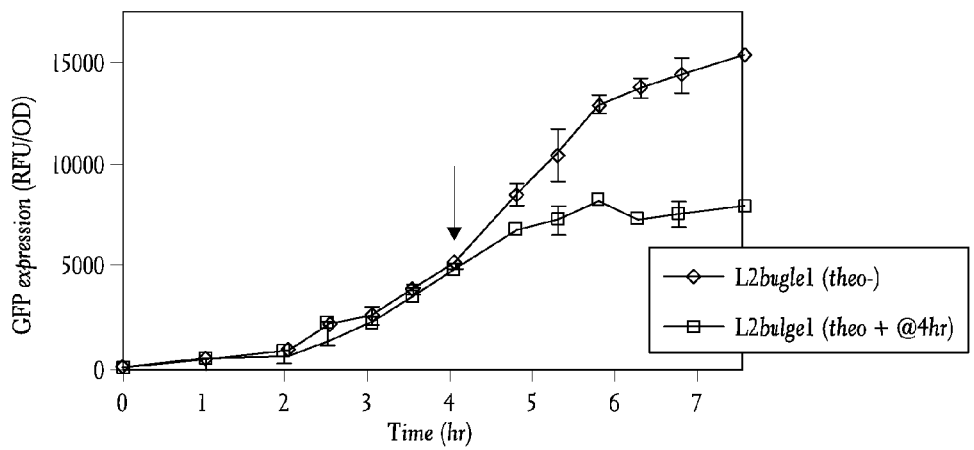
FIG. 12. Temporal responses of L2bulge1, L1cm10, and L2 cm4 in response to the addition of 5 mM theophylline (final concentration). The time point at which theophylline was added to the cultures is indicated by an arrow. Squares: 5 mM theophylline added to growing cultures; diamonds: no theophylline added to growing cultures. Gene expression levels are reported as RFU/OD by dividing fluorescence units by the $OD_{600}$ of the cell sample and subtracting the background fluorescence level. L2bulge1 exhibits up-regulation of GFP levels in response to the addition of theophylline; L1cm10 and L2 cm4 exhibit down-regulation of GFP levels in response to theophylline addition. The mean±s.d. from at least three independent experiments is shown for all graphs.
Figure 12:
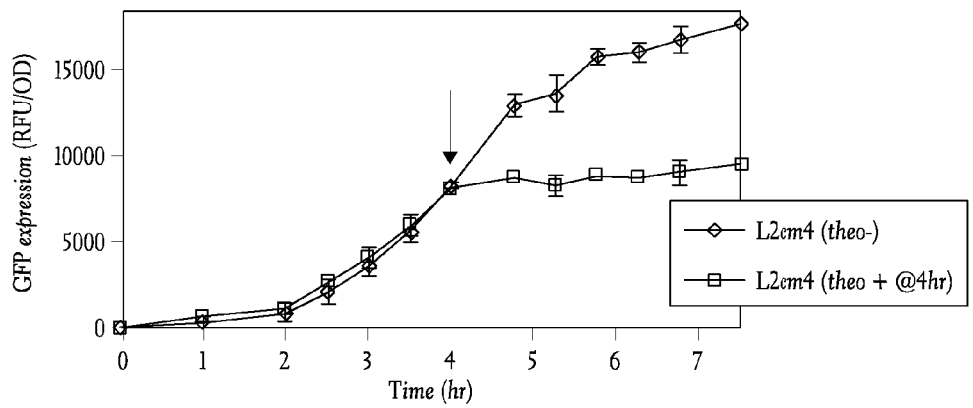
Figure 12:
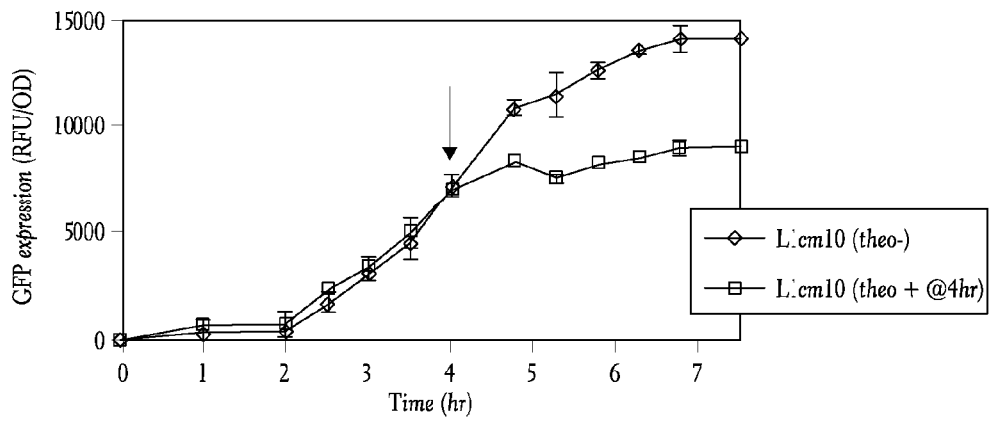

We validated the regulatory mechanisms of representative strand displacement- and helix slipping-based switches. Relative steady-state transcript levels in the absence and presence of effector are consistent with corresponding fluorescent protein levels, indicating that cleavage in the 3' UTR results in rapid decay and inactivation of the target transcript. In addition, we demonstrated that changes in expression levels are induced shortly after effector addition (FIG. 12), indicating that the response of the regulatory elements to changes in effector levels is relatively rapid.

Rational Tuning Strategies Enable Programming of Switch Regulatory Response

Figure 4A:
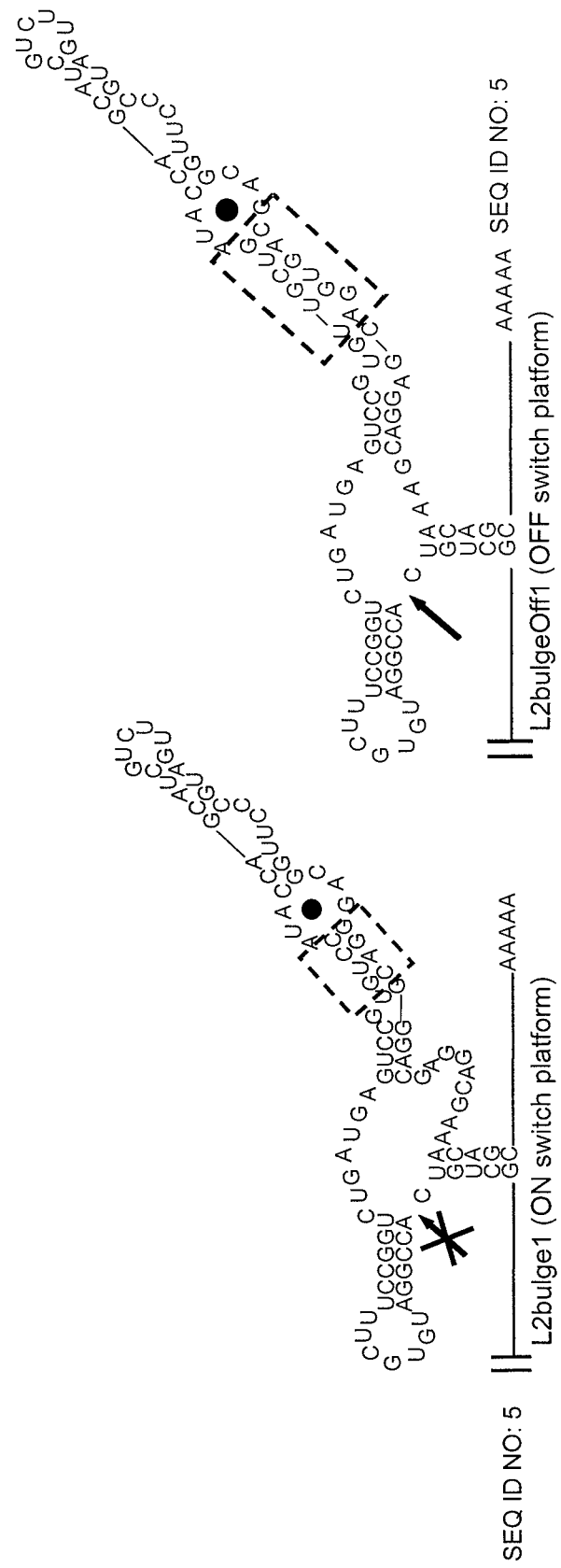
FIG. 4. Tunability of the strand displacement-based ribozyme switches. (A) Sequences targeted by the rational tuning strategies are indicated in the dashed boxes on the effector-bound conformations of L2bulge1 (ribozyme inactive) and L2bulgeOff1 (ribozyme active). Regulatory activities of tuned strand displacement-based (B) 'ON' and (C) 'OFF' ribozyme switches. Gene regulatory effects of these switches at 5 mM theophylline are reported in fold induction for 'ON' switches and fold repression for 'OFF' switches relative to the expression levels in the absence of theophylline as described in FIG. 2.
Figure 4B:
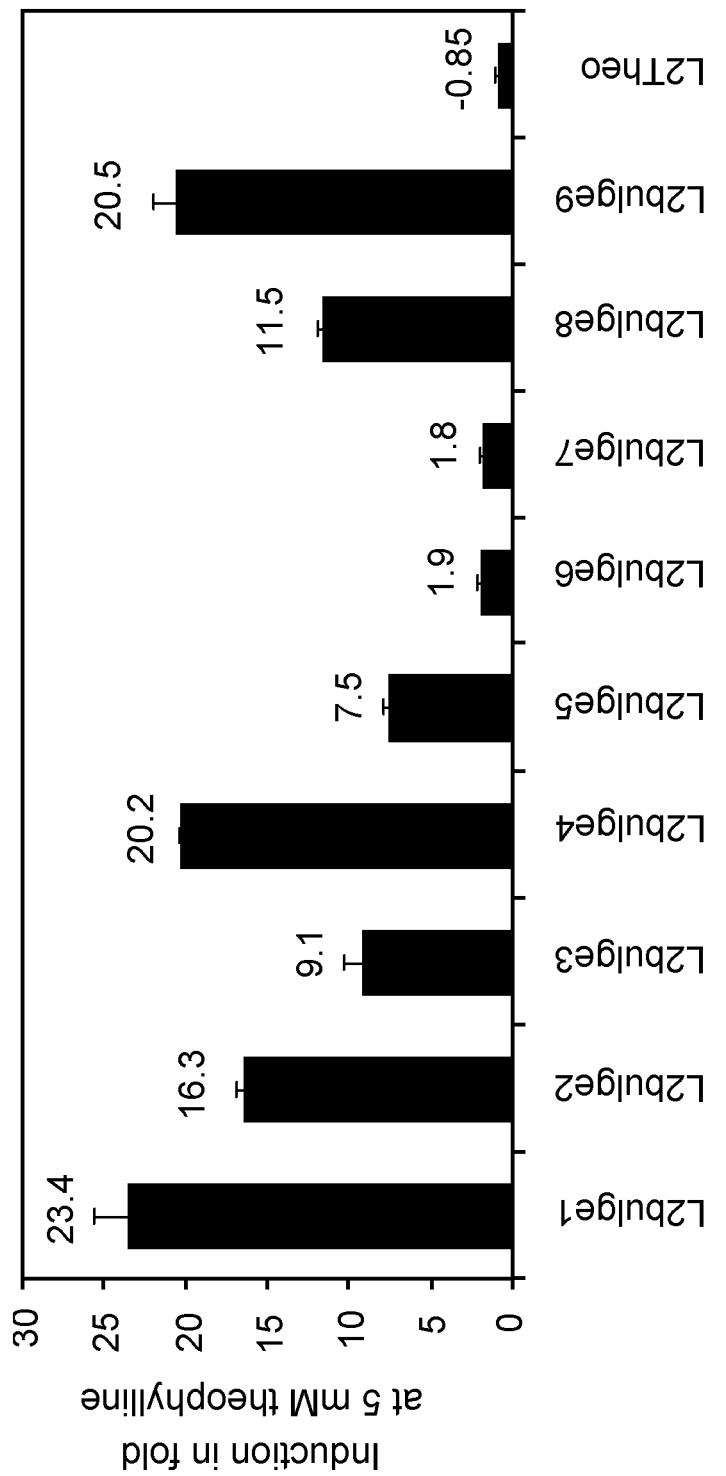
Figure 10:
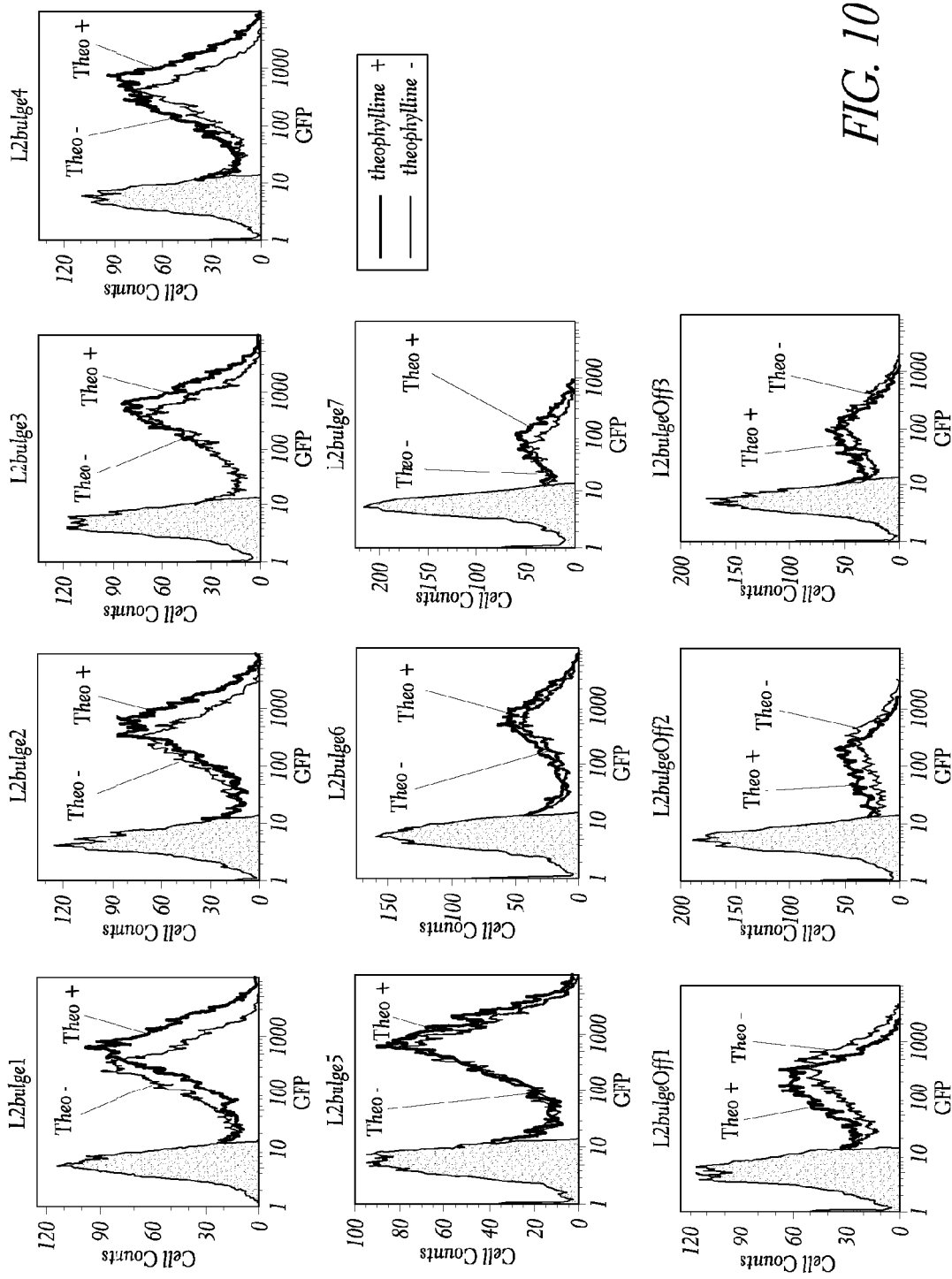
FIG. 10. Flow cytometry histograms of the tuned ribozyme switch series cell populations grown in the presence (+) and absence (−) of 5 mM theophylline. Population data is measured and reported as described in FIG. 8. Histograms are representative of three independent experiments.

The ability to program the regulatory response of a universal switch platform is an important property in tuning the platform performance to comply with the design specifications for a particular application. We demonstrate that our strand displacement-based switch platform incorporates an information transmission mechanism that is amenable to rational tuning strategies for programming response properties. Programming of new regulatory information is achieved by sequence alteration resulting in a change in the molecule's structural stability, which may affect its switching dynamics if the molecule can adopt multiple conformations. These rational sequence modification tuning strategies are not applicable to communication module-based switches due to an inability to predict their activities. A more complete description of our tuning strategies is provided in Example 2, FIGS. 13-14. Briefly, our rational tuning strategies target alteration of the nucleotide composition of the base stem of the aptamer domain to affect the stabilities of individual constructs and the energies required for the construct to switch between two adoptable conformations. Using these strategies, we rationally engineered a series of tuned 'ON' and 'OFF' switches from L2bulge 1 and L2bulgeOff1, respectively (FIG. 4A). These tuned switches exhibit different regulatory ranges in accordance with our rational energetic tuning strategies (FIGS. 4B, C, and FIG. 10).

The Ribozyme Switch Platform Exhibits Component Modularity and Specificity

Figure 5A:
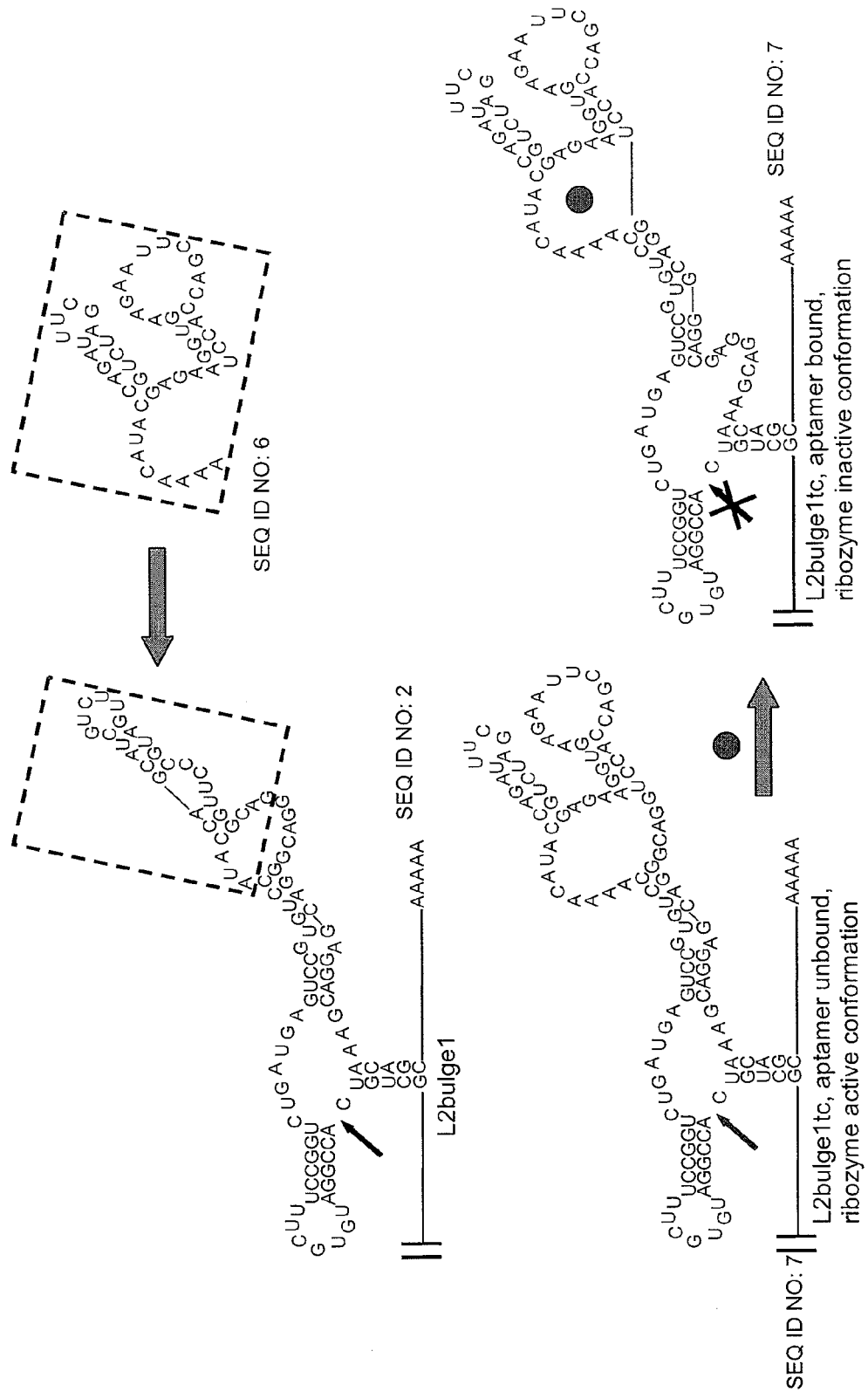
FIG. 5. Modularity and specificity of the strand displacement-based ribozyme switches. (A) Modular design strategies for the construction of new ribozyme switches. The theophylline (left dashed box) and tetracycline (right dashed box) aptamers are shown. (B) Regulatory activities of the modular ribozyme switch pair, L2bulge1 and L2bulge1tc, in response to their respective ligands, theophylline (theo) and tetracycline (tc), and closely-related analogues, caffeine (caff) and doxycycline (doxy). Regulatory effects are reported in fold induction relative to the expression levels in the absence of effector as described in FIG. 2.
Figure 5B:
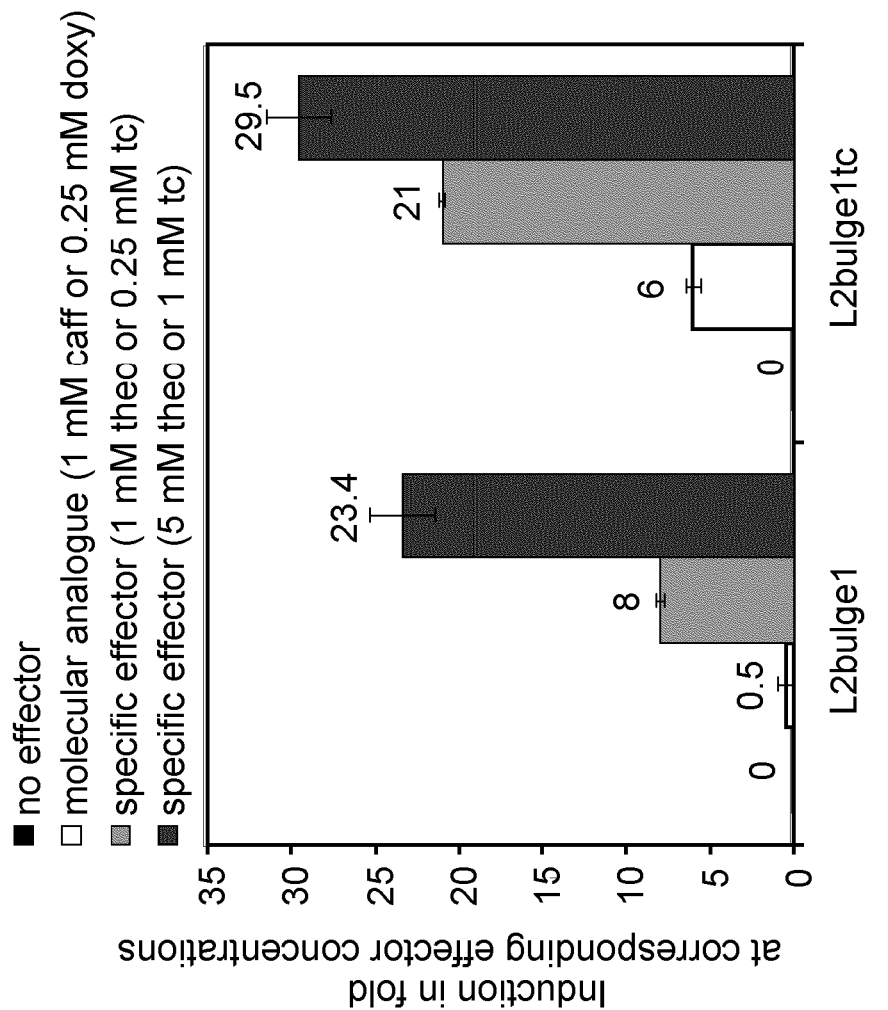

In implementing a standardized mechanism through which to transmit information between the domains of a switch platform (DP5), we needed to confirm that the modular coupling between the aptamer and ribozyme domains is maintained (DP4). We performed modularity studies on our strand displacement-based ribozyme switch platform, in which aptamers possessing sequence flexibility in their base stems can be swapped into the sensor domain. To begin to demonstrate that ribozyme switch activity may be controlled by different effector molecules we replaced the theophylline aptamer of L2bulge1 with a tetracycline mini-aptamer (25) to construct a tetracycline-responsive 'ON' switch (L2bulge1tc) (FIG. 5A). Despite similar aptamer ligand affinities (24, 25), the extent of up-regulation with L2bulge1tc was greater than that with L2bulge1 at the same extracellular concentration of their respective ligands (FIG. 5B). This is likely due to the high cell permeability of tetracycline (26) compared to theophylline (27). These results demonstrate that our strand displacement-based switch platform maintains modularity between the aptamer and ribozyme domains. We also performed similar modularity studies on the helix slipping-based switch platform by replacing the theophylline aptamer of L1cm10, L2 cm4 and L2 cm5 with the tetracycline mini-aptamer (L1cm10, L2 cm4tc and L2 cm5tc, respectively). These constructs do not exhibit effector-mediated gene regulatory effects (data not shown). We also demonstrated that the aptamer sequences (theophylline and tetracycline) incorporated into our ribozyme switch platforms maintain highly specific target recognition capabilities in vivo similar to their in vitro specificities generated during the selection process against corresponding molecular analogues (caffeine and doxycycline, respectively) (24, 25) (FIG. 5B). This is an important property in implementing these platforms in cellular engineering applications that involve complex environments where molecular species similar to the target ligand may be present.

Component Modularity Enables Implementation of Ribozyme Switches as Regulatory Systems in Diverse Applications To demonstrate the scalability and utility of these switch platforms as application-specific control systems, we demonstrate the implementation of ribozyme switches in two distinct cellular engineering application areas. First, utility (DP3) and the ability to respond to and control cellular information is demonstrated by the application of ribozyme switches to small molecule-mediated regulation of cell growth. Second, scalability (DP1) and the ability to respond to and report on cellular information is demonstrated by the implementation of ribozyme switches as non-invasive in vivo sensors of metabolite production.

Figure 6A:
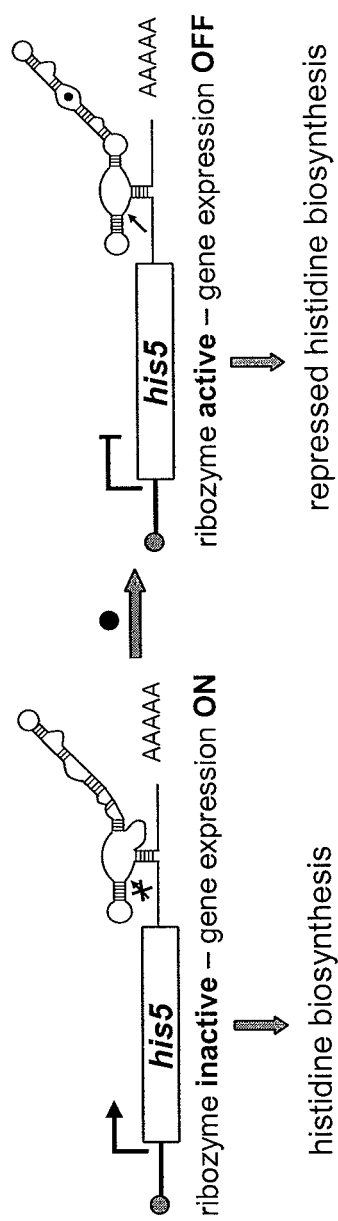
FIG. 6. System modularity of ribozyme switches enables implementation in diverse cellular engineering applications. (A) System design for ribozyme switch-based regulation of cell growth. Small molecule-mediated regulation of a gene required for cell growth is illustrated for a strand displacement-based 'OFF' switch. (B) Theophylline-mediated ribozyme switch-based regulation of cell growth. Changes in growth are reported as $OD_{600}$ values for cells grown in 5 mM 3AT in media lacking histidine. (C) System design for ribozyme switch-based in vivo sensing of metabolite production. Xanthine is synthesized from fed xanthosine and product accumulation over time is detected through a strand displacement-based xanthine-responsive 'ON' switch coupled to the regulation of a reporter protein. (D) Ribozyme switch-based xanthine synthesis detection through L2bulge9. Metabolite sensing through L2bulge9 is reported in fold induction of GFP levels relative to the expression levels in the absence of xanthosine feeding as described in FIG. 2. Expression data for experiments performed with L2bulge 1 exhibit similar induction profiles and levels (data not shown).
Figure 6B:
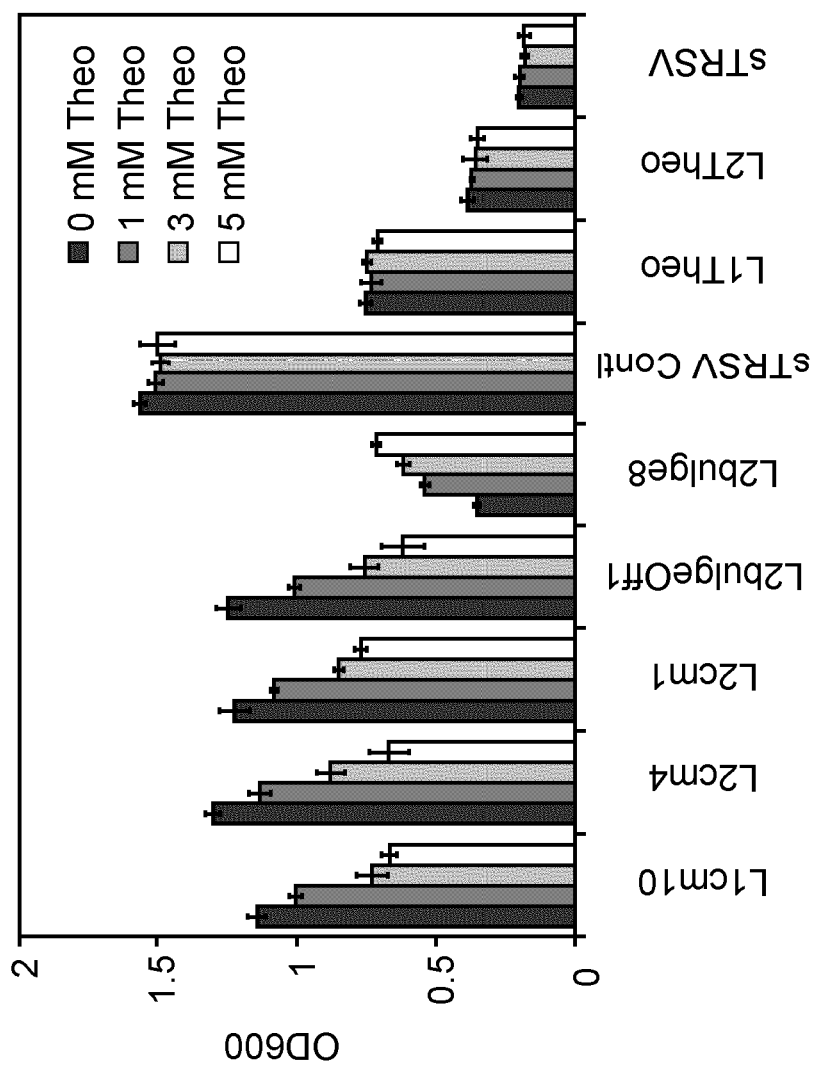
Figure 15:
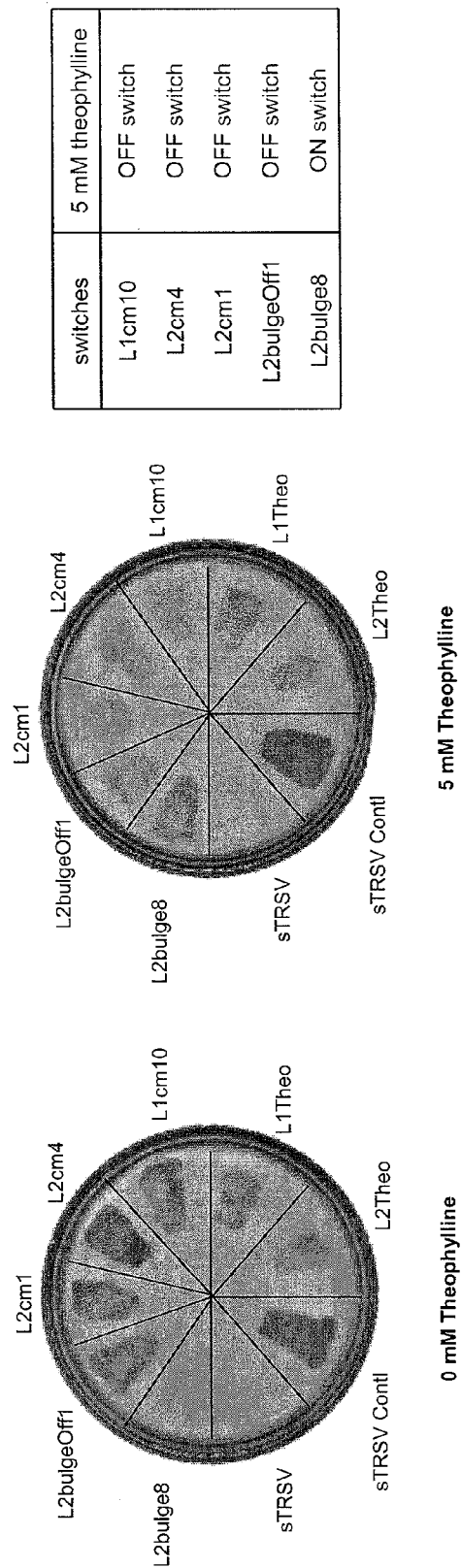
FIG. 15. Demonstration of theophylline-regulated cell growth by ribozyme switches through plate-based assays. Cells harboring ribozyme switches and control constructs were streaked on two plates containing the same medium except different effector concentrations (0 mM versus 5 mM theophylline). OFF switches (L1cm10, L2 cm4, L2 cm1, L2bulgeOff1) exhibit suppressed cell growth on the plate containing 5 mM theophylline while an ON switch (L2bulge8) exhibits a higher growth level on the plate containing 5 mM theophylline. The control constructs (L1Theo, L2Theo, sTRSV Contl, and sTRSV) exhibit similar growth levels on both plates. sTRSV exhibits no cell growth due to its efficient cleavage activity and sTRSV Contl exhibits the highest levels of growth due to its lack of cleavage activity.

The first system explores the application of our ribozyme switches to the regulation of a survival gene, where modification of expression levels is expected to produce an observable and titratable phenotypic effect on cell growth. The reporter gene within the original constructs was replaced with a growth-associated gene (his5) responsible for the biosynthesis of histidine in yeast (28) (FIG. 6A). We performed growth regulation assays across various effector concentrations using representative switch constructs and demonstrated that these switches mediate cell growth in a highly effector-dependent manner (FIG. 6B and FIG. 15). This application demonstrates the utility (DP3) of our switch platform, in which the control system exhibits modularity to the functional level components in the regulatory system.

Figure 6C:
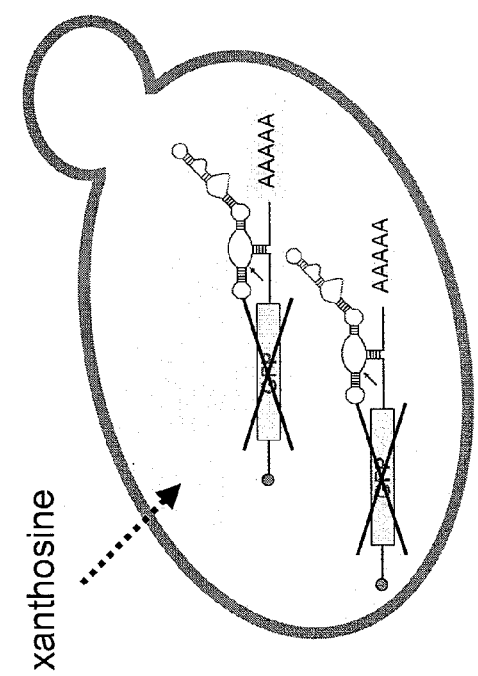
Figure 6C:
Figure 6C:
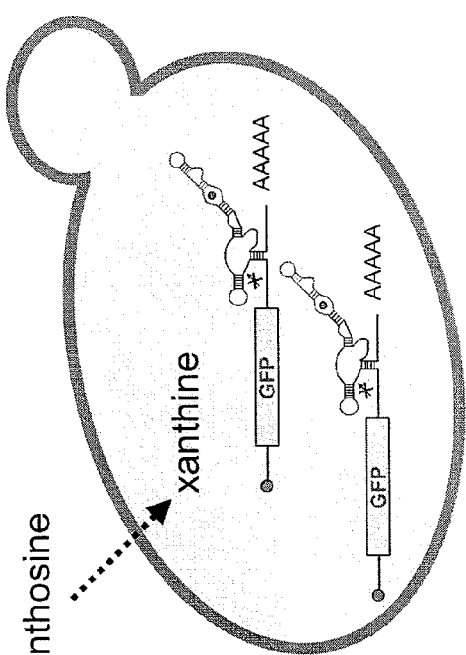
Figure 6D:
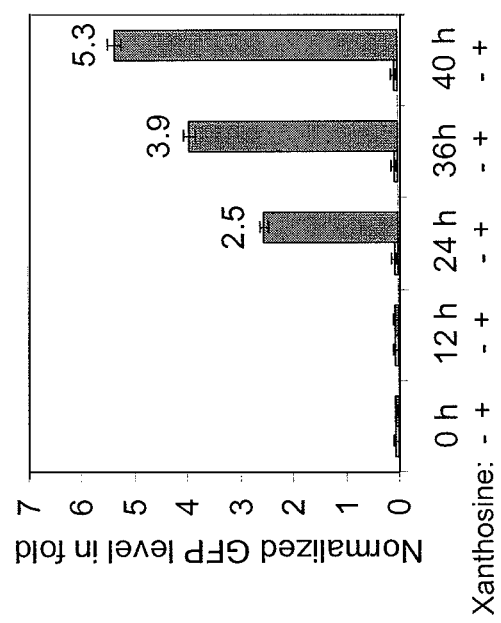
Figure 16:
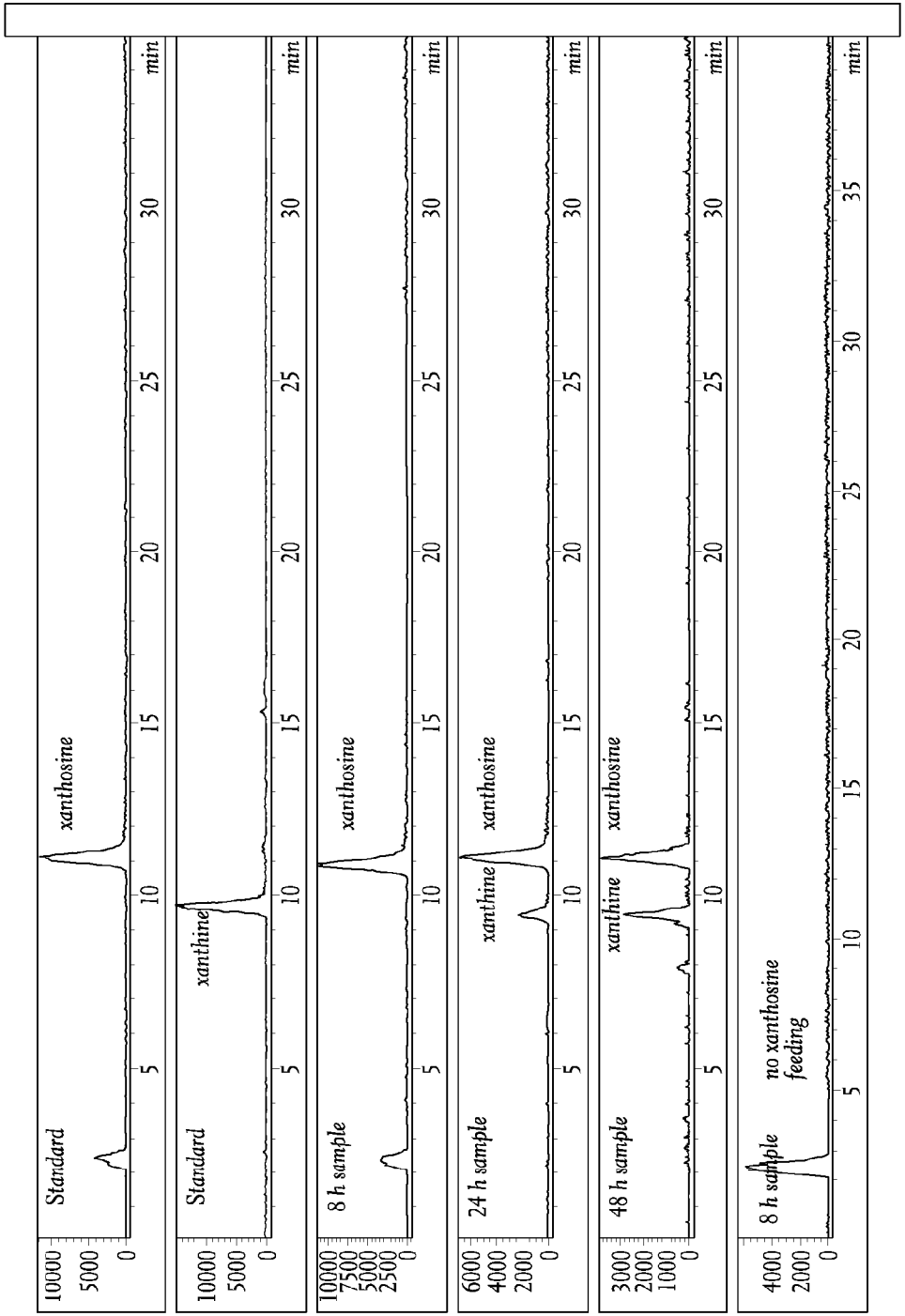
FIG. 16. Detection of intracellular accumulation of the substrate xanthosine and the product xanthine over three different time points. Accumulation of xanthosine is observed at earlier time points. Conversion of xanthosine to xanthine was detected at 24 h after substrate feeding and a higher accumulation of xanthine was detected at 48 h after substrate feeding.

The second system explores the application of these ribozyme switches to the in vivo sensing of metabolite production to demonstrate that these switches provide a non-invasive mechanism through which to transmit molecular information from cells. Nucleoside phosphorylase activities resulting in N-riboside cleavage of purine nucleosides have been identified in various organisms (29). We observe that feeding xanthosine to our yeast cultures results in the production of xanthine, a product synthesized through riboside cleavage of xanthosine. The theophylline aptamer employed in our switch platforms possesses a reduced binding affinity for xanthine (27-fold lower than theophylline) (24). We employed two 'ON' switch constructs (L2bulge1 and L2bulge9) for the in vivo detection of xanthine production in cultures fed xanthosine (FIG. 6C). GFP levels in cells fed xanthosine rose steadily between 24-40 h post-feeding in correlation with HPLC data (FIG. 6D and FIG. 16), illustrating the non-invasive metabolite-sensing capabilities of these switches through transmitting changes in metabolite accumulation to changes in reporter expression levels. This application demonstrates the scalability (DP1) of our switch platform, in which the unique properties of the sensing platform employed in this control system enable broad implementation in diverse applications not generally accessible by other regulatory systems.

Materials and Methods

Plasmid and Switch Construction. Using standard molecular biology techniques (30), a characterization plasmid, pRzS, harboring the yeast-enhanced green fluorescence protein (yEGFP) (31) under control of a GAL1-10 promoter, was constructed. For the ribozyme switch-mediated growth studies, the yegfp gene was replaced with the his5 gene (28). See Example 2 for details.

RNA Secondary Structure Prediction and Free Energy Calculation. RNAstructure 4.2 (on the World Wide Web at rna.urmc.rochester.edu/rnastructure.html) was used to predict the secondary structures of all switch constructs and their thermodynamic properties. RNA sequences that are predicted to adopt at least two stable equilibrium conformations (ribozyme inactive and active) were constructed and examined for functional activity.

Ribozyme Characterization, Cell Growth Regulation, and Metabolite Sensing Assays. See Example 2 for details. Briefly, cells harboring appropriate plasmids were grown in the absence and presence of corresponding ligands or substrates and characterized for ligand-regulated ribozyme switch activity, cell growth, and metabolite sensing.

Fluorescence quantification. See Example 2 for details.

Quantification of Cellular Transcript Levels. See Example 2 for details. Briefly, total RNA was extracted employing standard acid phenol methods (32) followed by cDNA synthesis and PCR amplification.

REFERENCES CITED IN EXAMPLE 1

1. Endy D (2005) Nature 438:449-53.
2. Voigt C A (2006) Curr Opin Biotechnol 17:548-57.
3. Kobayashi H, Kaern M, Araki M, Chung K, Gardner T S, Cantor C R, Collins J J (2004) Proc Natl Acad Sci USA 101:8414-9.
4. Gossen M, Bujard H (1992) Proc Natl Acad Sci USA 89:5547-51.
5. Lutz R, Bujard H (1997) Nucleic Acids Res 25:1203-10.
6. Mandal M, Breaker R R (2004) Nat Rev Mol Cell Biol 5:451-63.
7. Kim D S, Gusti V, Pillai S G, Gaur R K (2005) RNA 11:1667-77.
8. An C I, Trinh V B, Yokobayashi Y (2006) RNA 12:710-6.
9. Bayer T S, Smolke C D (2005) Nat Biotechnol 23:337-43.
10. Isaacs F J, Dwyer D J, Collins J J (2006) Nat Biotechnol 24:545-54.
11. Bunka D H, Stockley P G (2006) Nat Rev Microbiol 4:588-96.

12. Tuerk C, Gold L (1990) Science 249:505-10.
13. Ellington A D, Szostak J W (1990) Nature 346:818-22.
14. Hermann T, Patel D J (2000) Science 287:820-5.
15. Birikh K R, Heaton P A, Eckstein F (1997) Eur J Biochem 245:1-16.
16. Marschall P, Thomson J B, Eckstein F (1994) Cell Mol Neurobiol 14:523-38.
17. Khvorova A, Lescoute A, Westhof E, Jayasena S D (2003) Nat Struct Biol 10:708-12.
18. Yen L, Svendsen J, Lee J S, Gray J T, Magnier M, Baba T, D'Amato R J, Mulligan R C (2004) Nature 431:471-6.
19. Koizumi M, Soukup G A, Kerr J N, Breaker R R (1999) Nat Struct Biol 6:1062-71.
20. Soukup G A, Breaker R R (1999) Proc Natl Acad Sci USA 96:3584-9.
21. Soukup G A, Emilsson G A, Breaker R R (2000) J Mol Biol 298:623-32.
22. Kertsburg A, Soukup G A (2002) Nucleic Acids Res 30:4599-606.
23. Pelletier J, Sonenberg N (1985) Cell 40:515-26.
24. Jenison R D, Gill S C, Pardi A, Polisky B (1994) Science 263:1425-9.
25. Berens C, Thain A, Schroeder R (2001) Bioorg Med Chem 9:2549-56.
26. Hanson S, Berthelot K, Fink B, McCarthy J E, Suess B (2003) Mol Microbiol 49:1627-37.
27. Koch A L (1956) J Biol Chem 219:181-8.
28. Nishiwaki K, Hayashi N, Irie S, Chung D H, Harashima S, Oshima Y (1987) Mol Gen Genet. 208:159-67.
29. Ogawa J, Takeda S, Xie S X, Hatanaka H, Ashikari T, Amachi T, Shimizu S (2001) Appl Environ Microbiol 67:1783-7.
30. Sambrook J, Russell D W (2001) Molecular cloning: a laboratory manual (Cold Spring Harbor Laboratory Press, Cold Spring Harbor, N.Y.
31. Mateus C, Avery S V (2000) Yeast 16:1313-23. 32. Caponigro G, Muhlrad D, Parker R (1993) Mol Cell Biol 13:5141-8.

EXAMPLE 2

Supplemental Data for Aptamer-Regulated Cis-Ribozymes

Figure 7A:
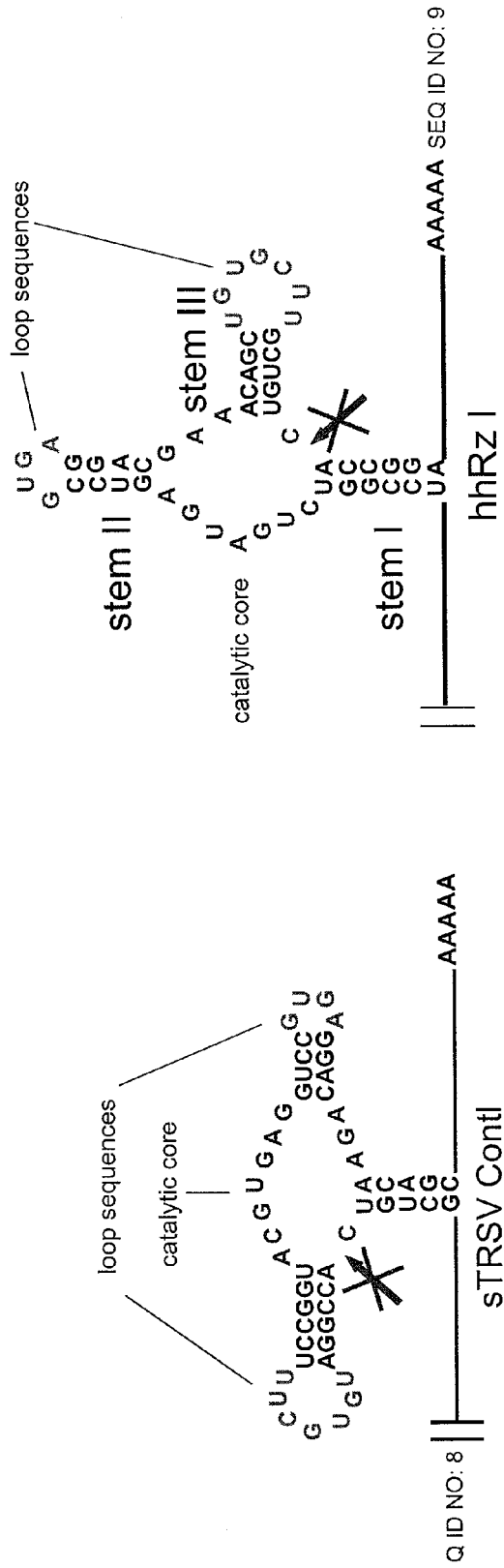
FIG. 7. Control constructs supporting the design strategy for engineering ligand-regulated ribozyme switches. (A) The arrow indicates the cleavage site. Sequences of the ribozyme (sTRSV Contl) and stem integration (hhRz I) controls. (B) Sequences of the loop sequence controls in which the loop I and II sequences are replaced by the theophylline aptamer (L1R and L2R, respectively). (C) Sequences of the loop sequence controls in which the theophylline aptamer is connected directly to the loop I nucleotides through L1.3 and L1.4 (L1Theo) and the loop II nucleotides through L2.2 and L2.3 (L2Theo). (D) Gene expression levels (in fold) of the control constructs. 1-fold is defined as the reporter gene expression level of sTRSV relative to that of the background fluorescence level. The mean+s.d. from at least three independent experiments is shown.
Figure 7B:
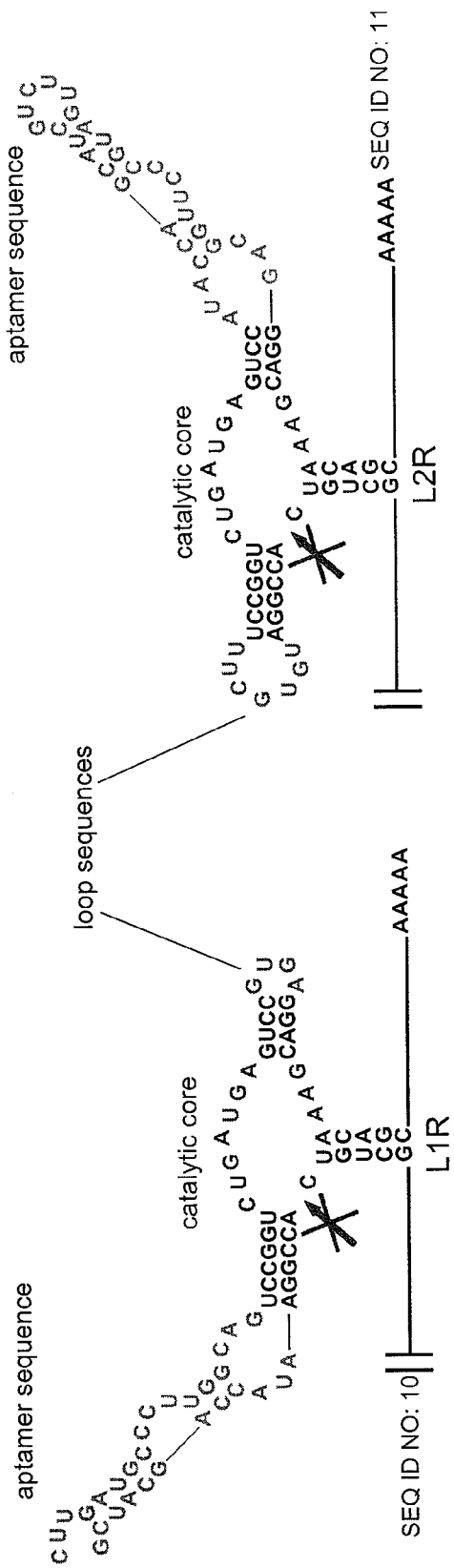
Figure 7C:
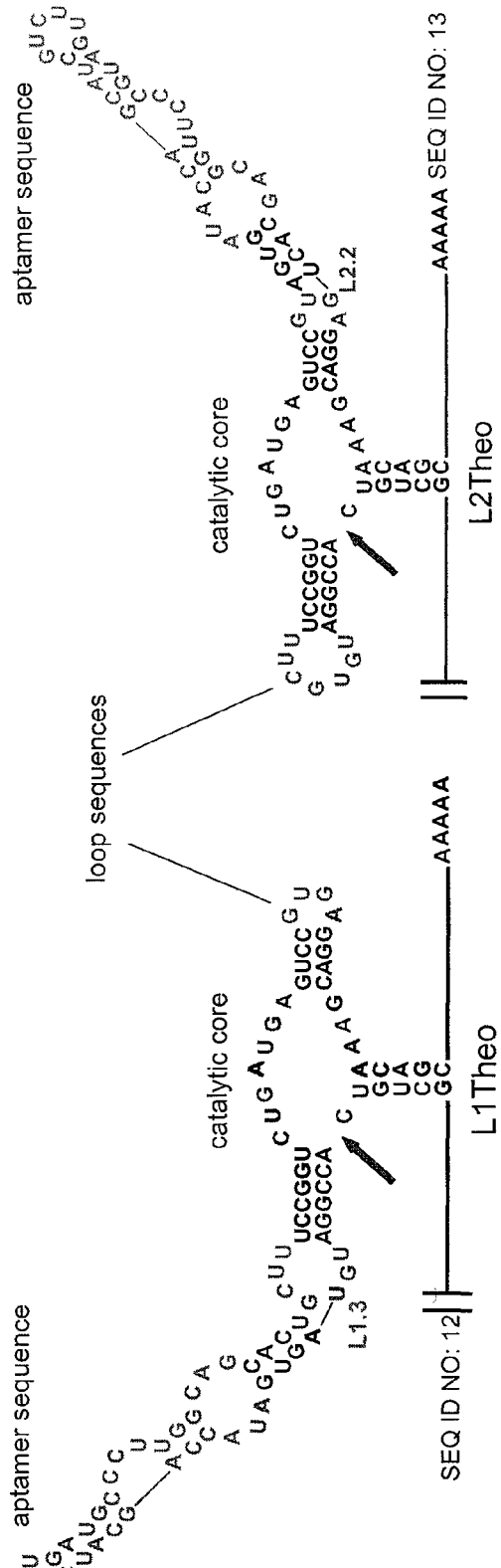
Figure 7D:
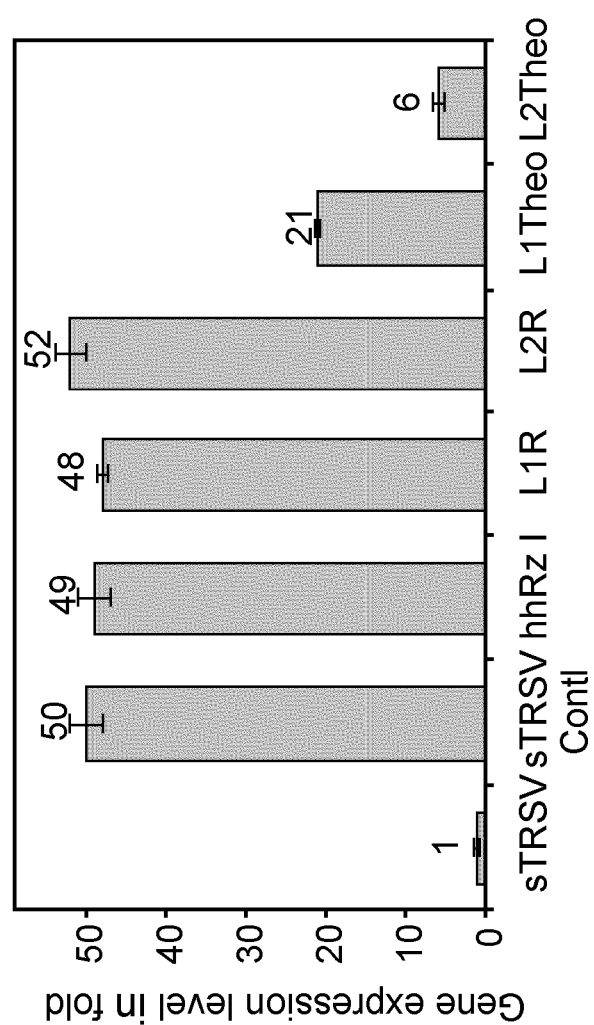

Ribozyme Control Constructs for Loop Sequence Coupling and Stem Integration Controls To establish and make useful our design strategy we constructed and characterized a series of ribozyme controls. We characterized the regulatory activity of our ribozyme constructs within a modular ribozyme characterization system in the eukaryotic model organism *Saccharomyces cerevisiae* (FIG. 1A). First, an inactive ribozyme control (sTRSV Contl) was constructed to adopt the same structural motif as sTRSV (FIG. 1A), while carrying a scrambled catalytic core sequence (FIG. 7A). Second, a synthetic sTRSV ribozyme (hhRz I) that contains closed loops in stems II and III and is embedded through stem I was constructed as a stem integration control (FIG. 7A). Finally, we constructed four loop sequence controls. In one set, stem loops I and II (L1R and L2R, respectively) were replaced by the theophylline aptamer TCT8-4 (S1) (FIG. 7B), and in another set, the theophylline aptamer was coupled directly to sequences in loops I and II (L1Theo and L2Theo, respectively) (FIG. 7C). sTRSV exhibits a 50-fold reduction in target expression levels relative to sTRSV Contl (FIG. 7D). HhRz I, UR, and L2R exhibit similar target expression levels to that of sTRSV Contl, suggesting that ribozyme activity was abolished in these constructs. In contrast, L1Theo and L2Theo exhibit significantly lower target expression levels relative to sTRSV Contl. L1Theo and L2Theo were employed as the primary base constructs in engineering our synthetic ribozyme switch platforms. In addition, scrambled core versions of L1Theo and L2Theo exhibit no theophylline-dependent shifts in gene expression (data not shown), indicating that theophylline binding in that region of the transcript alone is not responsible for the observed regulatory effects. Taken together, we find that our design strategy enables the construction of a universal ribozyme switch platform that satisfies the design principles of portability, utility, and composability.

Rational Tuning Strategies for Strand Displacement-Based Switches

A series of nine tuned 'ON' switches were constructed from L2bulge1 as a base structure by employing rational energetic tuning strategies developed in this work. This strategy is based on the effects of altering the predicted free energies of a particular conformation ($-\Delta G$) and the predicted difference between the free energies of two conformations ($\Delta\Delta G$) on RNA conformational dynamics, or the ability of the RNA molecule to distribute between these two conformational states. Lowering values for either of these energetic measurements ($-\Delta G$ or $\Delta\Delta G$) is expected to make it easier for a particular RNA molecule to switch between the conformational states in question. Therefore, there is an anticipated optimum conformational energy and energetic difference between conformations to achieve the desired range of switching in response to effector concentration (i.e., energy measurements too high will result in stable non-switch designs, and energy measurements or energy difference measurements too low will result in fairly equal distributions between the two conformational states and lower switching capabilities). It is also expected, then, that one can "push" switches into a non-switch state by moving away from this energetic optimum. This strategy was examined in a series of tuning experiments described below.

Figure 13:
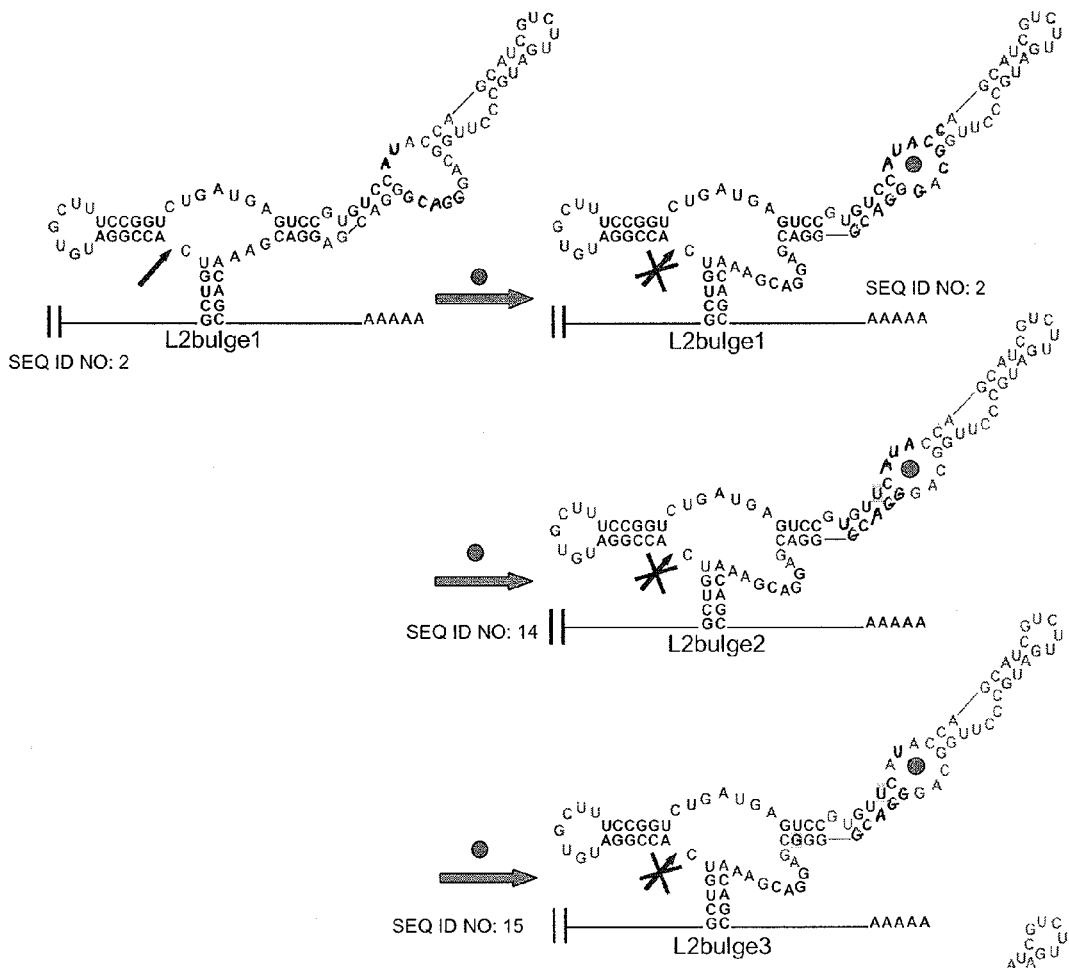
FIG. 13. Sequences and structures of tuned ribozyme switches in the L2bulge and L2bulgeOff series'. The nucleotides altered from the parent constructs, L2bulge1 and L2bulgeOff1, are highlighted. The two stable equilibrium conformations, ribozyme active and inactive conformations, are indicated for the parent ribozyme switches. The ribozyme active conformations of L2bulge2-5 are not shown as they are similar to L2bulge1. L2bulge6 and L2bulge7 assume a single predominant conformation, ribozyme inactive and ribozyme active, respectively, and do not undergo theophylline-induced conformational switching. L2bulge8 and L2bulge9, modified from L2bulge7 by reducing the stability of the ribozyme active conformation and the energy difference between the two conformations of L2bulge7, now become capable of switching. For these two modified switch constructs, only the ribozyme active conformations are shown, as their ribozyme inactive conformations are similar to those of the other switches illustrated. The ribozyme inactive conformations of L2bulgeOff2-3 are not shown as they are similar to L2bulgeOff 1.
Figure 1:
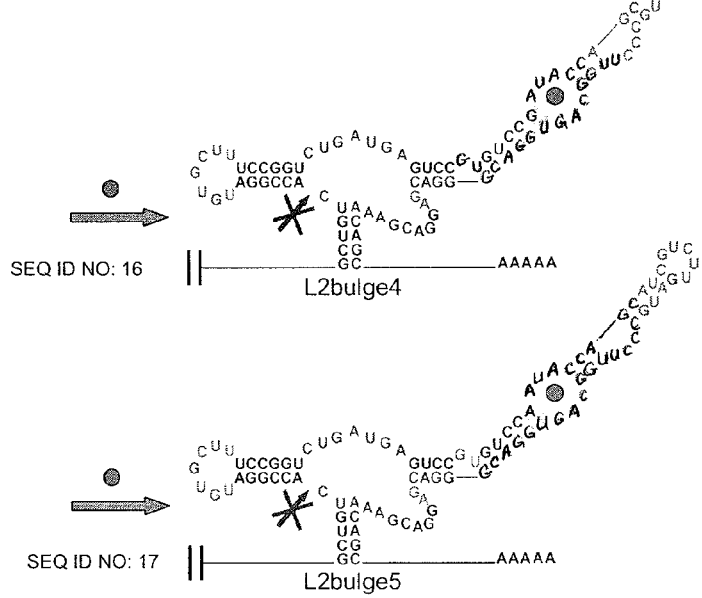
Figures 2, 13:
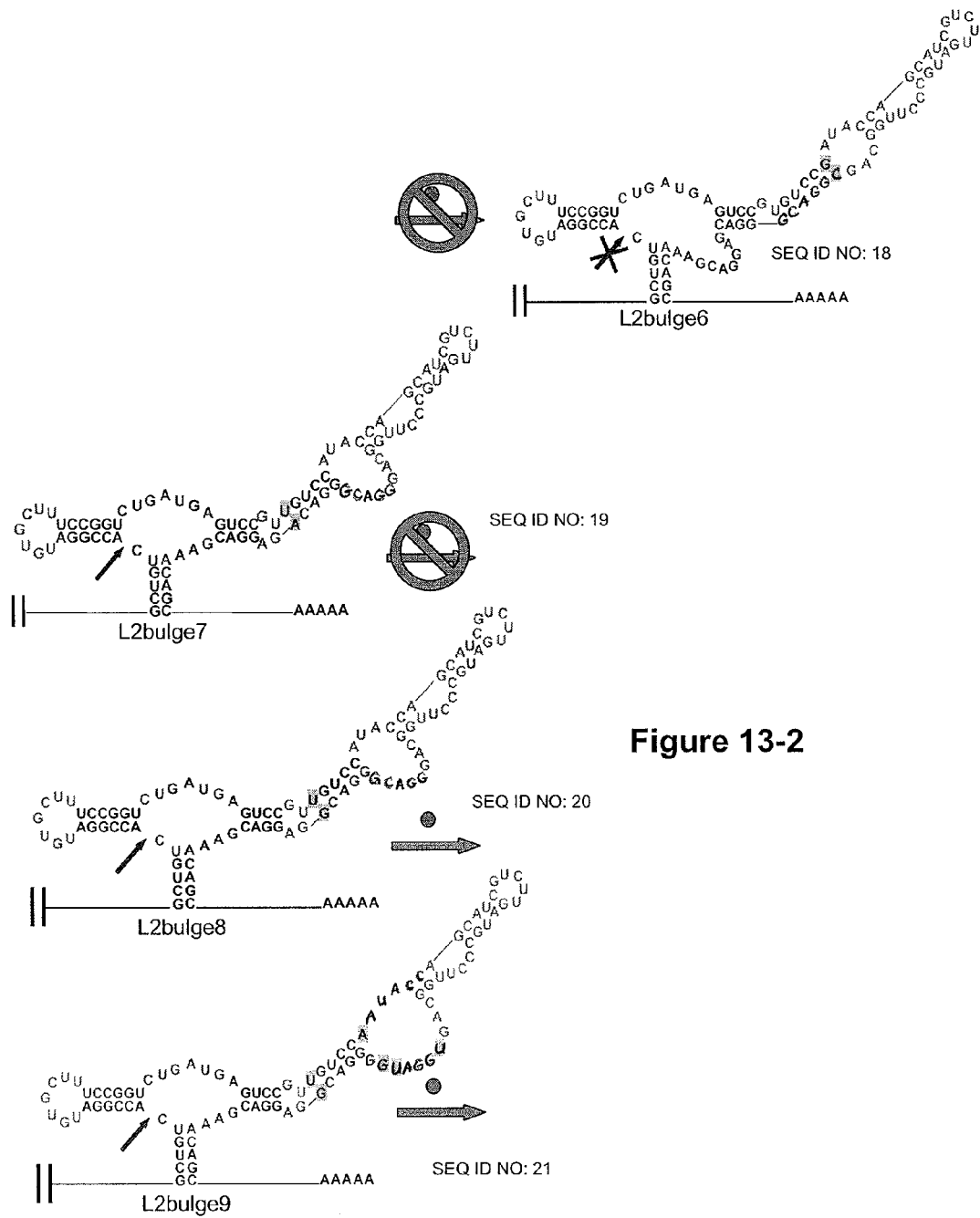
Figures 3, 13:
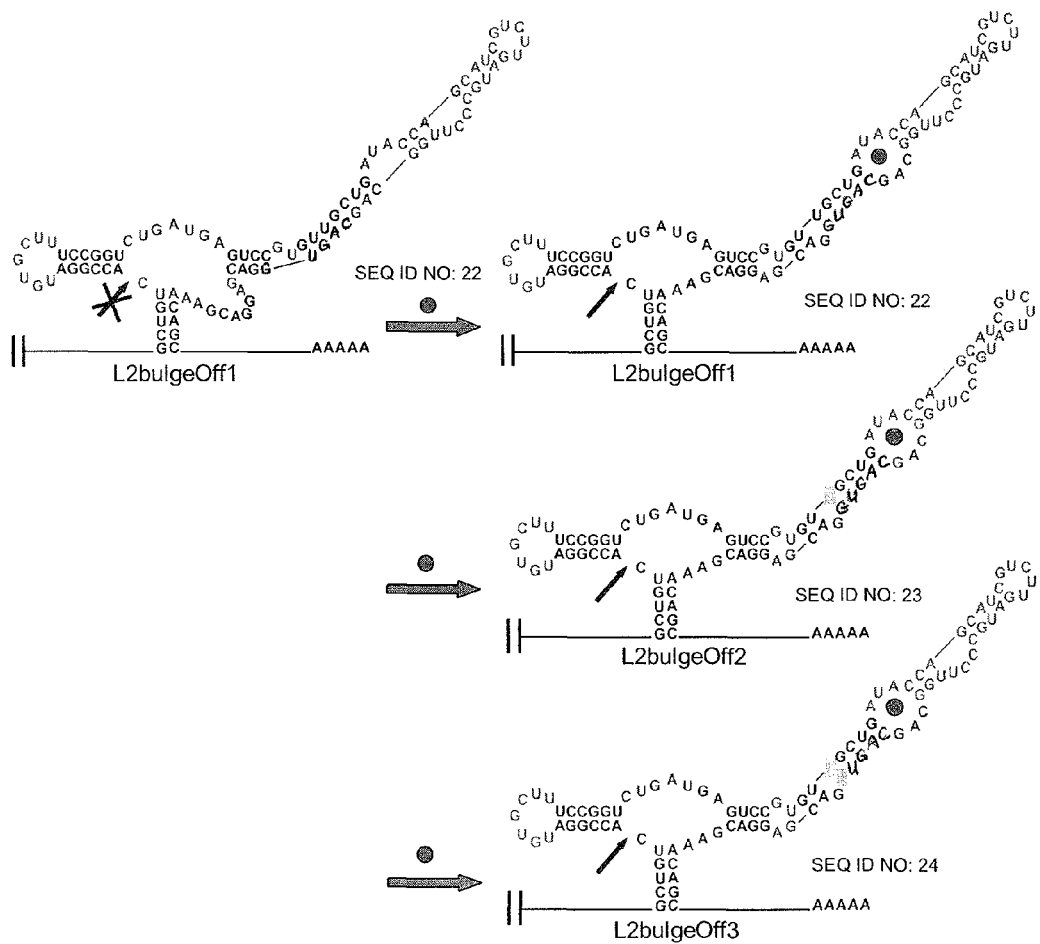
Figure 14:
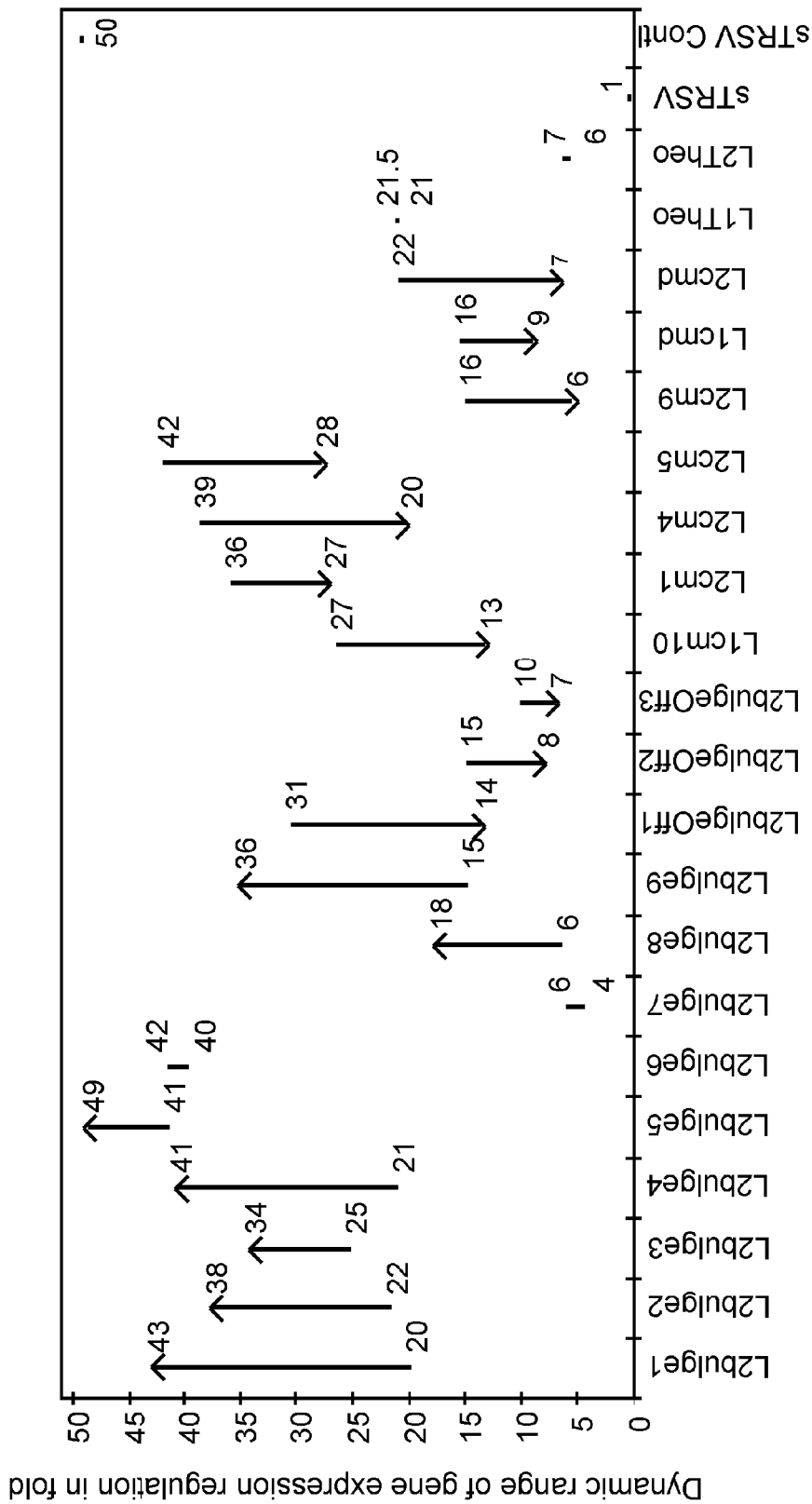
FIG. 14. Dynamic regulatory ranges of the ribozyme switches and controls engineered in this work. The regulatory effects at 5 mM theophylline are reported on a full transcriptional range spectrum scale without normalization to the corresponding base expression level of each switch in the absence of effector (0 mM). Little or no effector-mediated gene regulatory effect is observed in the non-switch control constructs. Gene expression fold is defined as previously where 1 fold is equivalent to the reporter gene expression level of sTRSV relative to the background fluorescence level. sTRSV is the most active ribozyme construct exhibiting the lowest gene expression level and sTRSV Contl is the most inactive ribozyme construct exhibiting the highest gene expression level, providing a 50 fold range as the full spectrum. Arrows indicate the direction of regulation as an increasing concentration of theophylline. These switches offer diverse dynamic ranges of regulation and thus provide a broader utility to fit specific applications of interest. Data are reported from three independent experiments.

L2bulge2 and L2bulge3 (FIG. 13) replace canonical base pairs in the aptamer base stem of the ribozyme inactive conformation of L2bulge1 with U-G wobble pairs. As a result of these destabilizing alterations, both equilibrium conformations (ribozyme active and ribozyme inactive) become less thermodynamically stable than those of L2bulge1, as estimated from their predicted free energies ($-\Delta G$). In addition, the energy required to switch between the two equilibrium conformations was maintained similar to that of L2bulge1, as estimated by the difference between the free energies of the two conformations ($\Delta\Delta G$). Ribozyme assays indicate that both L2bulge2 and L2bulge3 exhibit smaller dynamic ranges than that of L2bulge1 (FIG. 4B and FIG. 14). It is proposed that the lower stabilities of the conformational states enable more frequent dynamic switching between the two equilibrium conformations and therefore lower the difference in distribution favoring one state over the other.

L2bulge4 (FIG. 13) incorporates an additional G-U wobble pair within the aptamer base stem of the ribozyme inactive conformation of L2bulge1. However, this aptamer stem extension does not result in an appreciable predicted change in the thermodynamic stabilities of the equilibrium conformations or the energy required to switch between the two equilibrium conformations when compared to L2bulge1. Ribozyme assays indicate that L2bulge4 exhibits a dynamic range in response to theophylline levels similar to that of L2bulge1 (FIG. 4B and FIG. 14).

L2bulge5 (FIG. 13) incorporates an additional canonical base pair (A-U) within the aptamer base stem of L2bulge1. As a result of this stabilizing alteration, the conformation of the ribozyme switch, in which the aptamer structure is formed and the catalytic core is disrupted (ribozyme inactive), is increased in stability and as stable as the conformation in which the catalytic core is not disrupted (ribozyme active). The increased stability of the ribozyme inactive conformation in L2bulge5 in comparison to L2bulge1 and L2bulge4 indicates that the equilibrium distribution between these two conformations will shift to favor the ribozyme inactive conformation. Ribozyme assays indicate that L2bulge5 exhibits significantly higher GFP expression levels in the absence and presence of theophylline compared to those of L2bulge1 and L2bulge4, such that the theophylline-regulated increase in gene expression is similar to that of L2bulge3 but different in regulatory dynamic ranges (FIG. 4B and FIG. 14).

Two switches in this series, L2bulge6 and L2bulge7, were constructed to demonstrate the ability of this tuning strategy to "push" the ribozyme switch constructs out of a switchable energetic range and approach non-switching extremes. L2bulge6 (FIG. 13) was designed to energetically favor the conformation, in which the aptamer structure is formed and the catalytic core is disrupted, (ribozyme inactive) in the absence of theophylline by introducing a stabilizing G-C base pair into the aptamer stem of this conformation. Since the aptamer conformation is expected to be favored in L2bulge6, the presence of theophylline is expected to have little or no effect on the conformational dynamics of this switch. L2bulge7 (FIG. 13) was designed to energetically favor the conformation, in which the aptamer structure is not formed and the catalytic core is undisrupted (ribozyme active), by introducing a stabilizing U-A base pair into the stem extending from loop II in this conformation. As the stability of the ribozyme active conformation is significantly higher than that of the ribozyme inactive conformation for L2bulge7, the presence of theophylline is expected to have little effect on the conformational dynamics of this ribozyme switch. Ribozyme assays indicate that L2bulge7 exhibits very low GFP expression levels and L2bulge6 exhibits very high GFP expression levels in the presence and absence of theophylline (FIG. 14). As rationally designed, both constructs exhibit little increase in target expression levels in response to theophylline by energetically favoring one of the two conformational states (FIG. 4B).

L2bulge8 (FIG. 13) was modified from L2bulge7 by replacing the canonical base pair (U-A) with a wobble base pair (U-G), thereby reducing the stability of the ribozyme active conformation of L2bulge7 and allowing it to adopt the ribozyme inactive conformation. Similarly, L2bulge9 (FIG. 13) was modified in such a way to reduce the energy difference between the two conformations of L2bulge7. Ribozyme assays indicate that L2bulge8 and L2bulge9 exhibit theophylline-dependent up-regulation of target gene expression in accordance with the reduced stabilities of the ribozyme active conformations and energy differences between the two adoptable conformations for each of these switch constructs (FIG. 4B and FIG. 14).

Figure 4C:
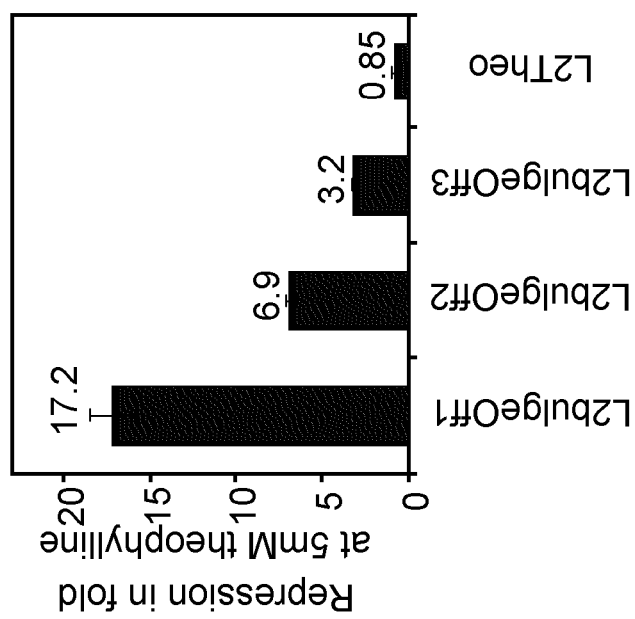

In addition, a series of three tuned 'OFF' switches were constructed by using rational energetic tuning strategies from L2bulgeOff 1 as a base structure. L2bulgeOff2 and L2bulgeOff3 were constructed to demonstrate tunability of the 'OFF' switch platform using similar energetic design strategies (FIG. 13). These switch variants exhibit different theophylline-responsive dynamic ranges from that of L2bulgeOff1 (FIG. 4C and FIG. 14).

Flow cytometry analysis of the tuned ribozyme switch series demonstrate that the tuned switches exhibit corresponding shifts in the mean fluorescence of the cell populations in the presence and absence of theophylline (FIG. 10). The relative dynamic ranges of the switches across the full regulatory range bracketed by the ribozyme active and inactive controls, sTRSV and sTRSV Cont1 respectively, are presented in FIG. 14.

Among the twelve tuned switches (both 'ON' and 'OFF'), the dynamic regulatory ranges of most of these switches are in agreement with our rational tuning strategies based on the $-\Delta G$ and $\Delta\Delta G$ values predicted by RNAstructure 4.2. Two exceptions are noted: L2bulge9 and L2bulgeOff3. L2bulge9 exhibits a larger dynamic regulatory effect despite its higher $\Delta\Delta G$ than L2bulge8. L2bulgeOff3 exhibits a smaller dynamic regulatory effect despite its smaller $\Delta\Delta G$ than L2bulgeOff2. However, it is more difficult to make a direct comparison between L2bulgeOff2 and L2bulgeOff3, as both conformations of L2bulgeOff3 are significantly more stable than those of L2bulgeOff2, likely resulting in L2BulgeOff3 less frequently switching between its two conformations and thus enabling this molecule to get 'trapped' in its lower free energy states. In addition, outliers may also arise because the RNAstructure program predicts these energy values based on the secondary structure of a particular conformation and does not take into consideration energy contributions from tertiary interactions (that have been observed in prior work (S2)) in estimating these energies. Nevertheless, we demonstrate that energetic predictions based solely on secondary structure are useful for our rational tuning design strategies. The different dynamic regulatory ranges exhibited by our tuned switches in response to their specific effector (FIG. 14) validate that such response programming can be achieved by altering the nucleotide composition of the information transmission region within a switch, thereby demonstrating the interdependence between RNA sequence, structure, and function.

Detailed Methods and Materials

Plasmid and Switch Construction. The modular plasmid, pRzS, was constructed and employed as a universal vector for the characterization of all ribozyme switches. The engineered ribozyme constructs were generated by PCR amplification using the appropriate oligonucleotide templates and primers. All oligonucleotides were synthesized by Integrated DNA Technologies. All engineered ribozyme constructs were cloned into two unique restriction sites, AvrII and XhoI, 3 nucleotides downstream of the yEGFP stop codon and upstream of an ADH1 terminator. Cloned plasmids were transformed into an electrocompetent *Escherichia coli* strain, DH10B (Invitrogen) and all ribozyme constructs were confirmed by subsequent sequencing (Laragen, Inc). Confirmed plasmid constructs were transformed into a *S. cerevisiae* strain (W303 MAT a his3-11,15 trpl-1 leu2-3 ura8 3-1 ade2-1) using standard lithium acetate procedures (S3).

Ribozyme Characterization Assays. *S. cerevisiae* cells harboring the appropriate plasmids were grown in synthetic complete medium supplemented with an appropriate drop-out solution and sugar (2% raffinose, 1% sucrose) overnight at 30° C. Overnight cultures were back diluted into fresh medium to an optical density at 600 nm ($OD_{600}$) of approximately 0.1 and grown at 30° C. An appropriate volume of concentrated effector stock (to the appropriate final concentration of theophylline or tetracycline) dissolved in medium or an equivalent volume of the medium (no effector control) was added to the cultures at the time of back dilution. In addition, at this time an appropriate volume of galactose (2% final concentration) or an equivalent volume of water were added to the cultures for the induced and non-induced controls, respectively. For specificity assays, an appropriate volume of a concentrated caffeine or doxycycline stock (final concentrations of 1 mM and 250

µM, respectively) was added to a separate culture. Cells were grown to an $OD_{600}$ of 0.8-1.0 or for a period of approximately 6 h before measuring GFP levels on a Safire fluorescent plate reader (Tecan) and/or on a Cell Lab Quanta SC flow cytometer (Beckman Coulter). For temporal response assays, cultures were grown as described above in the absence of the appropriate effector and fluorescence data were taken every 30 min. After 4 h growth, appropriate volumes of the concentrated effector stock or plain medium were added to the cultures and fluorescence was monitored for several hours thereafter.

Cell Growth Regulation Assays. For liquid culture assays, S. cerevisiae cells carrying appropriate plasmids were back diluted and grown according to procedures described above with minor modifications. A competitive inhibitor of the his5 gene product, 3-amino-triazole (3AT), was added to a final concentration of 5 mM to increase the threshold level of histidine required for cell growth. Cultures were grown in various theophylline concentrations and the growth of each sample was monitored over a 24 h period. The theophylline-regulated growth at 24 h is reported in terms of $OD_{600}$ readings measured on the Tecan. For plate-based assays, 10 µL of the back diluted culture samples was streaked on plates containing 0 and 5 mM theophylline. A higher concentration of 3AT (25 mM) was used in the plate-based assays to optimize visual assessment of theophylline-regulated cell growth.

Metabolite Sensing Assays. S. cerevisiae cells carrying appropriate plasmids were back diluted and grown according to procedures described above with minor modifications. Cultures were grown in the absence and presence of xanthosine (250 µM final concentration). To account for inducer depletion, galactose was added to the cultures at 8 h time intervals to a 2% final concentration. Fluorescence levels of the samples were monitored over a 48 h period according to procedures described above. For HPLC analysis, cell extracts were prepared after appropriate growth periods following xanthosine feeding by rapid freezing of cell cultures in liquid nitrogen in the form of beads. Frozen cell beads were subsequently lysated by grinding using a mortar and pestle followed by extraction with methanol. Intracellular metabolite levels were analyzed using an HPLC system integrated with a mass spectrometer (HPLC-MS) (Agilent Technologies), which enables confirmation of metabolite peaks based on their corresponding molecular weights.

Fluorescence Quantification. The population-averaged fluorescence of each sample was measured on a Safire fluorescence plate reader with the following settings: excitation wavelength of 485 nm, an emission wavelength of 515 nm, and a gain of 100. Fluorescence readings were normalized to cell number by dividing fluorescence units by the $OD_{600}$ of the cell sample and subtracting the background fluorescence level to eliminate autofluorescence. Fluorescence distributions within the cell populations were measured on a Quanta flow cytometer with the following settings: 488 nm laser line, 525 nm bandpass filter, and PMT setting of 5.83. Fluorescence data was collected under low flow rates for approximately 30,000 cells. Viable cells were selected and fluorescence levels were determined from 10,000 counts in this selected population. A non-induced cell population was used to set a 'negative GFP' gate. Cells exhibiting fluorescence above this negative gate are defined as the 'positive GFP' cell population.

Similar to previous reports (S4, S5), we report gene expression levels as 'fold', where 1 fold is defined as the reporter gene expression level of sTRSV relative to the background fluorescence level. Ligand-directed regulatory effects are reported as fold gene expression levels normalized to the levels in the absence of effector. All fluorescence data and mean±s.d. are reported from at least three independent experiments.

Quantification of Cellular Transcript Levels. cDNA was synthesized using gene-specific primers and Superscript III Reverse Transcriptase (Invitrogen) following manufacturer's instructions. Relative transcript levels were quantified from the cDNA samples by employing an appropriate primer set and the iQ SYBR Green Supermix (BioRAD) according to manufacturer's instructions on an iCycler iQ qRT-PCR machine (BioRAD). The resulting data were analyzed with the iCycler iQ software according to manufacturer's instructions. Transcript levels of switch constructs were normalized to that of the endogenous actI gene (S6) using actI-specific primers. All data are reported from three independent experiments.

REFERENCES CITED IN EXAMPLE 2

S1. Jenison R D, Gill S C, Pardi A, Polisky B (1994) Science 263:1425-9.
S2. Khvorova A, Lescoute A, Westhof E, Jayasena S D (2003) Nat Struct Biol 10:708-12.
S3. Gietz R, Woods R (2002) in Guide to Yeast Genetics and Molecular and Cell Biology, Part B, eds. Guthrie C, Fink, G (Academic Press, San Diego, Vol. 350, pp. 87-96).
S4. Isaacs F J, Dwyer D J, Ding C, Pervouchine D D, Cantor C R, Collins J J (2004) Nat Biotechnol 22:841-7.
S5. Yen L, Svendsen J, Lee J S, Gray J T, Magnier M, Baba T, D'Amato R J, Mulligan R C (2004) Nature 431:471-6.
S6. Ng R, Abelson J (1980) Proc Natl Acad Sci USA 77:3912-6.

EXAMPLE 3

The Ribozyme Switch Platform Exhibits Portability Across Diverse Cellular Systems The cleavage activity of the hammerhead ribozyme is independent of cell type, as it does not require cell-specific machinery to assist its self-cleavage, thereby making this regulatory element universally applicable to different cellular systems. Therefore, in order to demonstrate that the constructed ribozyme-based switch platform retains ligand-regulated gene control activity in a cellular system different than S. cerevisiae, we implemented the strand displacement-based ON switches (L2bulge1, L2bulge8, and L2bulge9) in mammalian T cells (CTLL-2). Similar to the implementation in yeast, the ribozyme switch constructs were built by placing these switches downstream (in the 3' UTR, surrounded by spacer/insulater sequences) of a target fusion gene encoding enhanced green fluorescence protein (EGFP) and interleukin-2 (IL-2). An increase in target gene expression levels was observed in the presence of 1 mM theophylline in all ON switches, relative to those in the absence of effector (FIG. 17), exhibiting a ligand-dependent up-regulation of gene expression by this ON switch in mammalian cells and demonstrating the switch platform portability across different cellular systems.

Alternative Strategies for Programming the Dynamic Range of Switch Response

Figure 17:
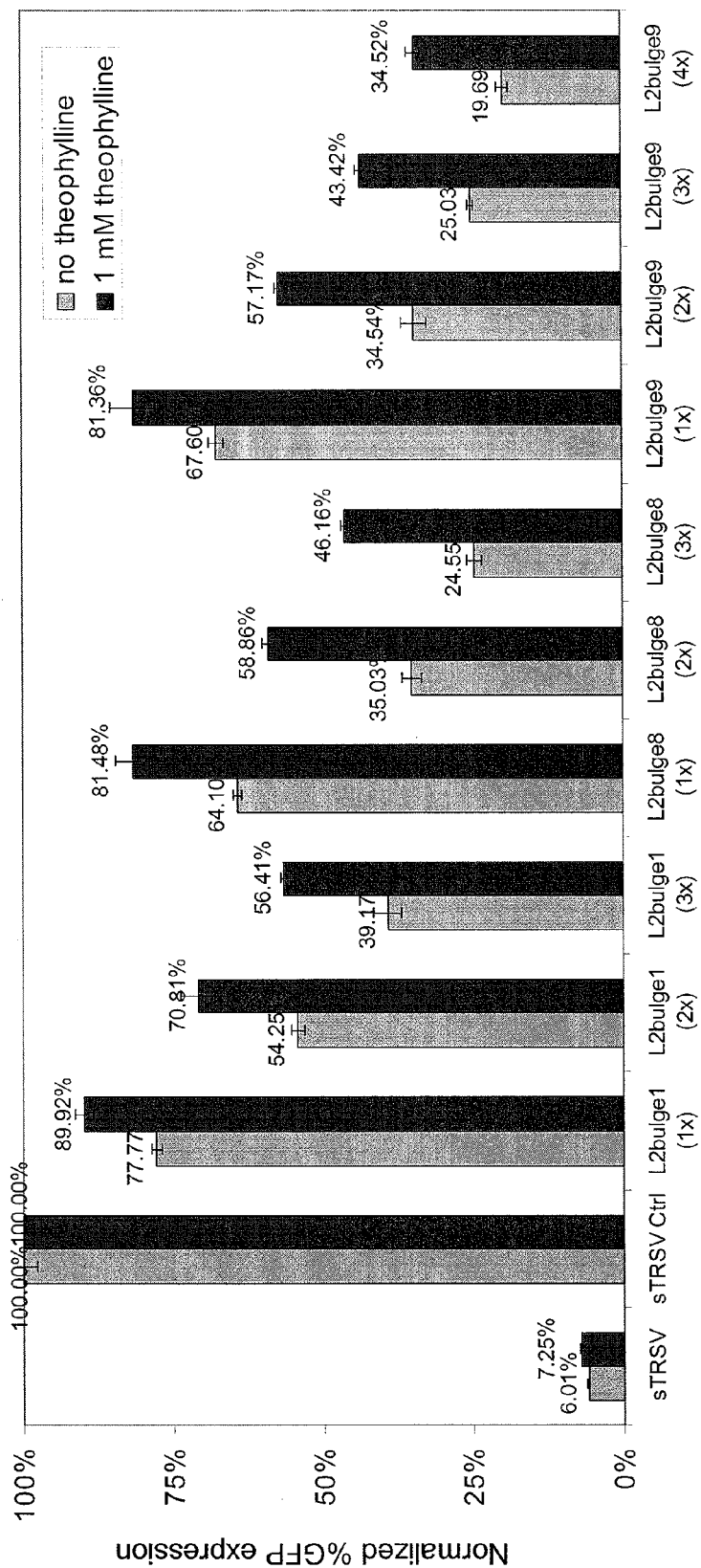
FIG. 17. Ligand-regulated gene control of the ribozyme switch platform in mammalian cells, demonstrating platform portability across different cellular systems. All switches exhibit higher gene expression levels in the presence of 1 mM theophylline compared to those in the absence of theophylline, while the ribozyme control constructs show little difference in expression levels in the absence and presence of theophylline. (#x) indicates the number of independent ribozyme switches placed in the 3' UTR of the target transcript (see next section).
Figure 18:
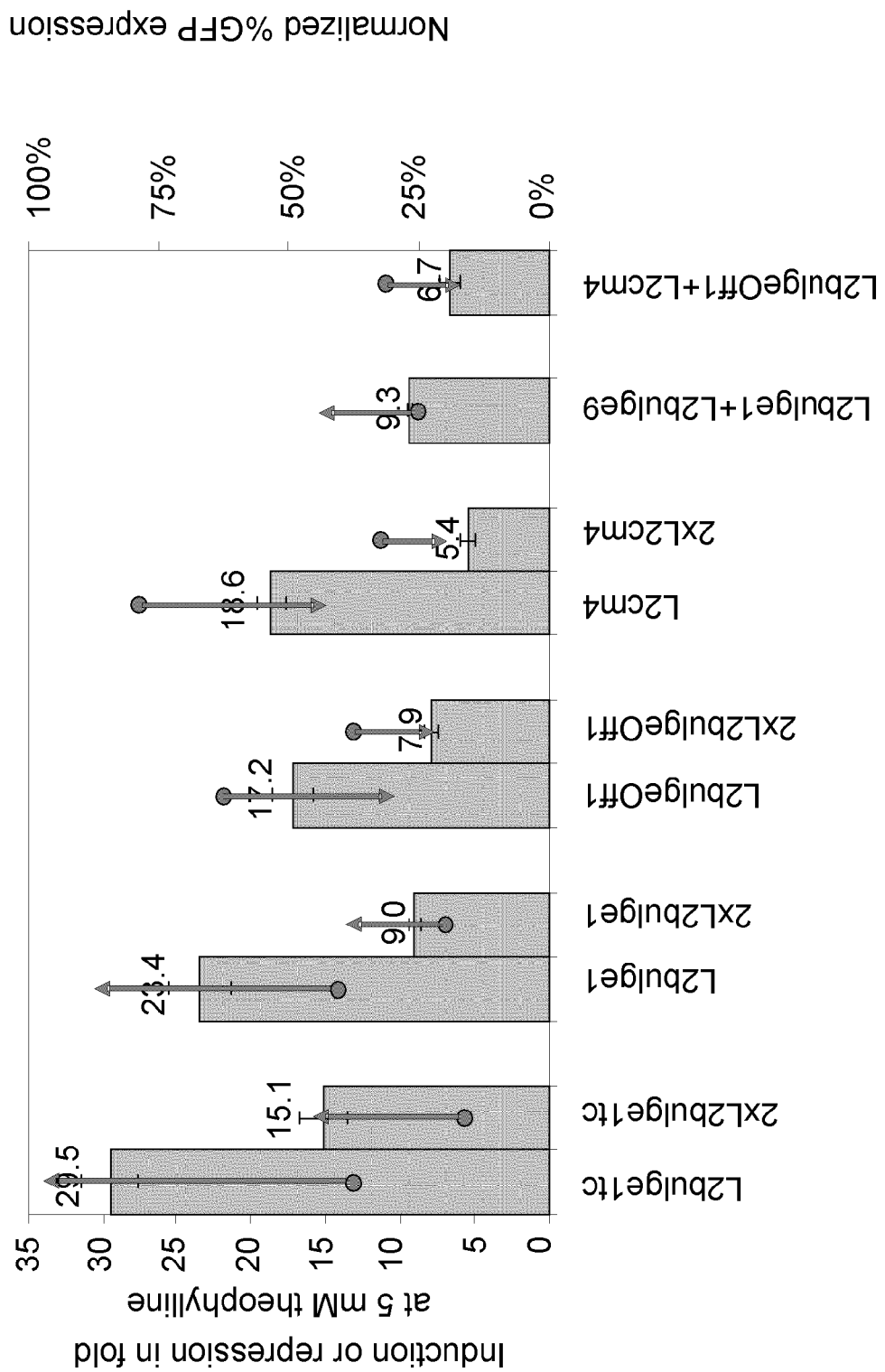
FIG. 18. Ligand-regulated gene regulatory responses and dynamic ranges of single- and multi-copy ribozyme switch constructs. Arrows indicate the direction of regulation. (#x) indicates the number of independent ribozyme switches placed in the 3' UTR of the target transcript FIG. 19. The hammerhead ribozyme. A) The catalytic core, NUX sequence, flanking helical regions and Stem II are labeled in the figure. Ovals represent stem loops. B) Ribozyme cleavage mechanism at the NUX triplet. C) Folding of the ribozyme is thought to proceed through two magnesium binding events. D) The "Y"-shaped ribozyme is thought to be stabilized by loop interactions between unpaired bases in the stem loops.

The dynamic regulatory response of the ribozyme switch platform can be programmed to yield new regulatory response ranges through the expression of multiple copies of individual, identical switches within the 3' UTR of the target gene. For instance, when these switches were expressed in multiple copies, the ligand-regulated dynamic response ranges of these multi-copy switch constructs were observed to be different from those exhibited by single-copy switch constructs. Specifically, the multi-copy constructs exhibit lower expression levels both in the absence and presence of effector than those of the corresponding single-copy constructs due to the independent cleavage activity of each ribozyme switch, which results in higher over all cleavage activity of the combined system. This tuning method is applicable in different cellular systems as shown in FIGS. 17 and 18. Therefore, multi-copy expression of a ribozyme switch provides a programming method through which to achieve a dynamic regulatory response different from that of the single switch parent, particularly when a regulatory system resulting in a low basal expression level is desired.

EXAMPLE 4

Development of Trans-Ribozymes for In Vivo Utility

We have taken the rules for in vivo activity established for cis-ribozymes and applied them to the development of trans-ribozymes. We demonstrate that precise engineering of the intramolecular reaction between the ribozyme and target transcript is required for efficient trans-ribozymes at intracellular $Mg^{2+}$ concentrations. To improve the correlation between our in vitro and in vivo assays of ribozyme efficiency, we employed a dual cis-hammerhead ribozyme cassette to excise our trans-ribozymes designs from the ribonucleoprotein particle in vivo. Additionally, we developed an improved in vitro assay that more accurately translates in vitro cleavage efficiency into in vivo regulation of target transcripts. We anticipate that these newly constructed fast, efficient trans-hammerhead ribozymes will efficiently regulate gene expression in vivo.

Ribozymes as Actuators

Ribozymes are RNA molecules that catalyze a variety of chemical reactions such as self-cleavage or ligation [13]. Various naturally occurring ribozymes have been identified in viruses, viroids, and protozoans. One of the first catalytic RNAs was discovered in the satellite RNA of the tobacco ring spot viroid (sTRSV) [14]. In vivo this pathogenic viroid was shown to act in cis and self-cleave during replication. Since the discovery of the first ribozyme, various classes of natural ribozymes, including hairpin and hammerhead ribozymes, have been identified and extensively characterized.

The hammerhead ribozyme (hRz) is one of the most extensively studied ribozymes [13, 15-17]. It is comprised of three helical regions that converge on a highly conserved catalytic core of eleven nucleotides (nts) (FIG. 19A) [18, 19]. Cleavage is sequence-specific and targets a 5'-NUX-3' triplet, where N is any base, U is uracil, and X is any base except guanine. The optimal NUX for efficient and fast cleavage is GUC. Ribozyme cleavage is catalyzed when the 2' hydroxyl group from X directly 3' of the cleavage site is deprotonated. This nucleophile then attacks the scissile phosphate and, through a penta-coordinated trigonal bi-pyramidal transition state, produces a 5' and 3' product (FIG. 19B) [17].

Figure 19:
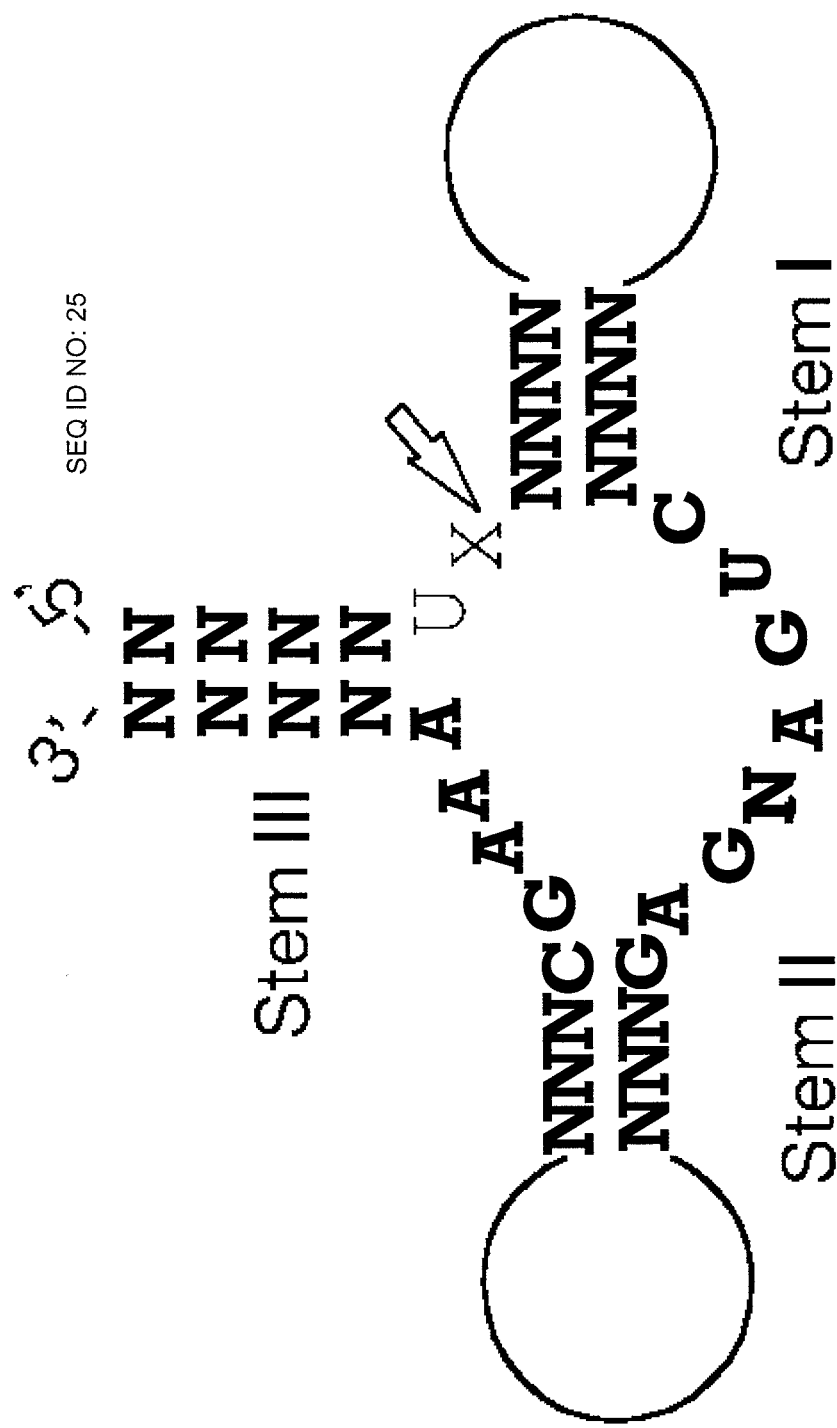
Figure 19B:
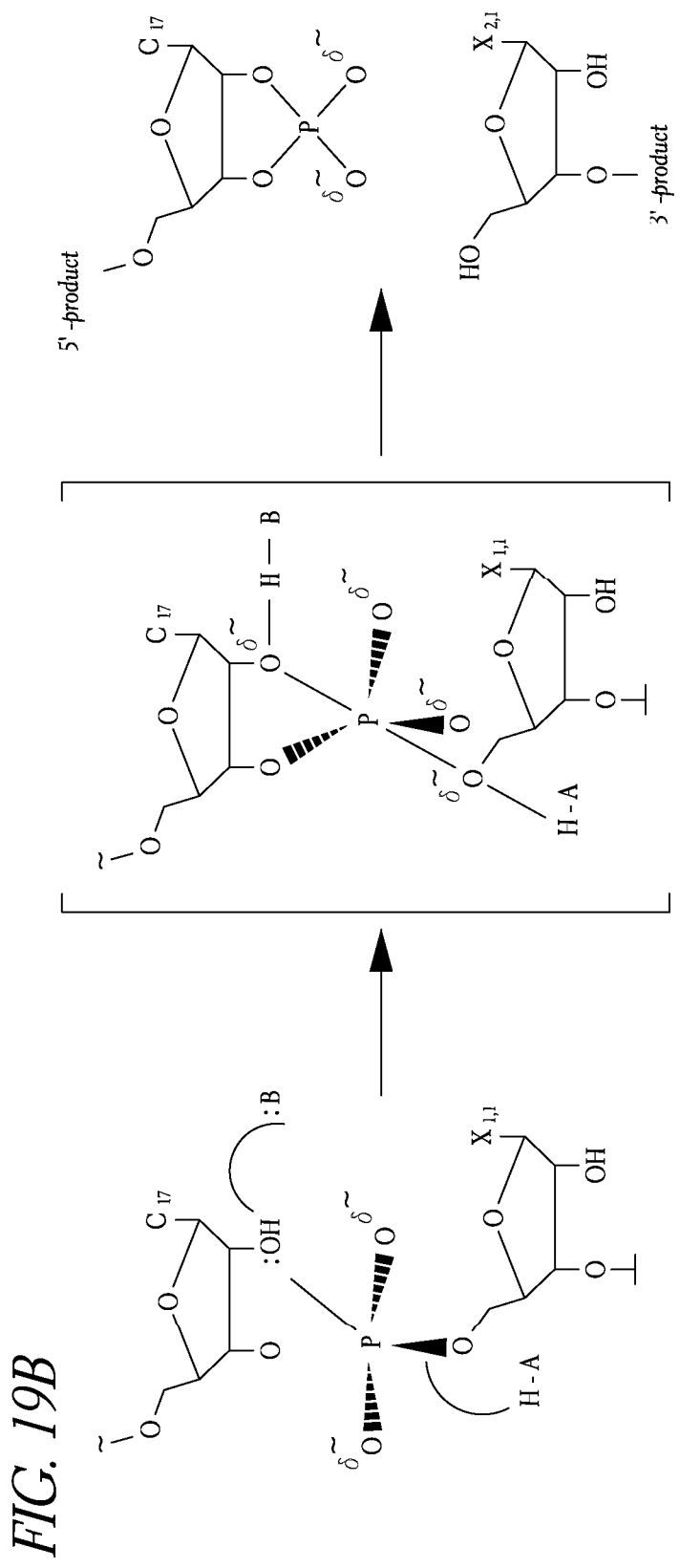
Figure 19:
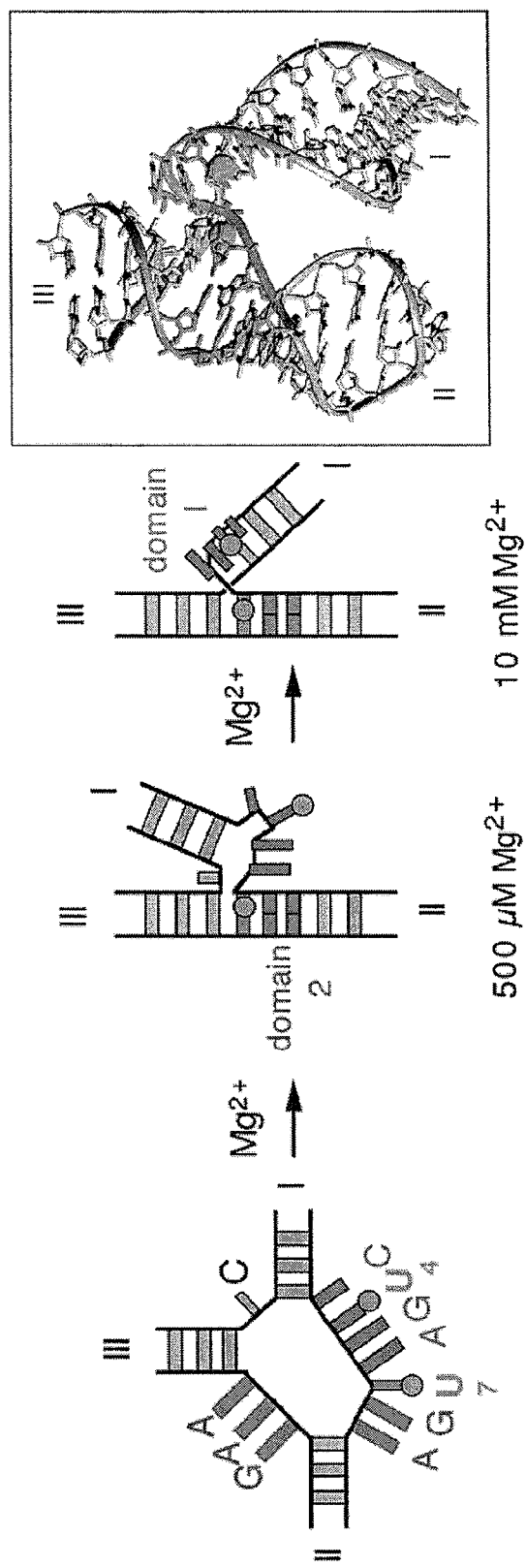
Figure 19:
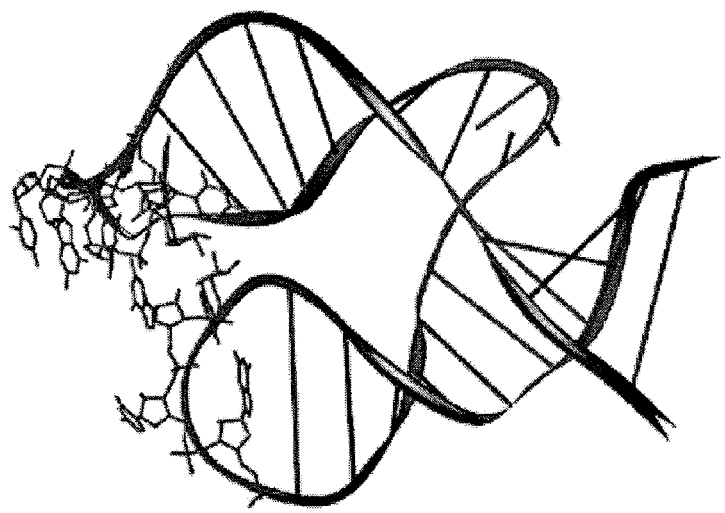
Figure 19:
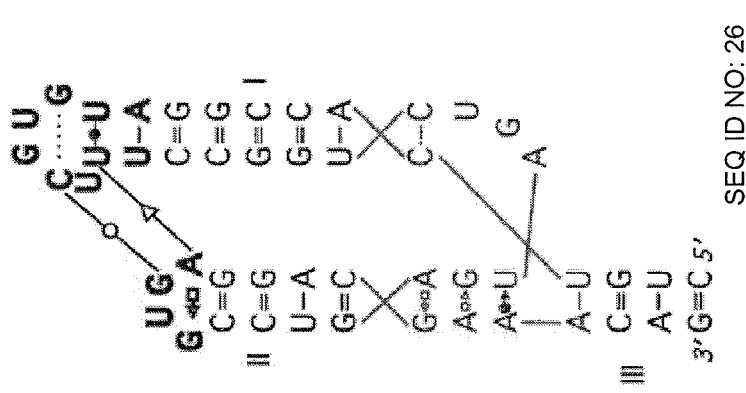

Folding of the hRz into an active conformation is postulated to proceed through dual divalent ion binding events (FIG. 19C). A high affinity binding event occurs at 500 µM and orders the first set of tertiary interactions. The second low affinity addition of ion occurs at 10 mM and restructures the hRz stem orientations such that helix I folds away from helix III and interacts with helix II [16]. HRzs with conserved catalytic cores that do not maintain specific stem loops are called minimal hammerhead ribozymes (mhRzs). While mhRzs are active at high divalent ion concentrations (10 mM), at lower concentrations mhRzs are effectively inert [14, 18]. Crystal structures of natural hRz depict a "Y"-shaped molecule that has two of the stem loops interacting as "kissing loops" (FIG. 19D) [15]. These tertiary interactions between unpaired bases in the stem loops are proposed to stabilize the catalytically active conformation and obviate high divalent ion conditions. Researchers have demonstrated restored in vitro catalytic activity at biologically-relevant divalent ion concentrations, between 100 and 500 µM, by reincorporating the loops into mhRz designs [14, 18, 20-23]. Through elucidation of the design rules for in vivo catalytic activity, hRz are now poised to be effective regulators of gene expression.

We have taken the rules established for in vivo activity of cis-hRzs (chRz) and applied them to the development of trans-hRz (thRz). We demonstrate additional design constraints for efficient thRz cleavage in engineering the intramolecular binding event between the ribozyme and target transcript. In particular, we demonstrate that engineering the stem loops and the length of the targeting arms of the thRz is necessary to achieve efficient cleavage of the target transcript in vitro. This work represents the first attempt to regulate gene expression via thRz in the model eukaryotic organism S. cerevisiae. In future work, we expect the newly designed ribozymes to yield the first demonstration of in vivo regulation of gene expression via thRz. Additionally, the development of this regulatory platform poises it for the development of thRz-based ligand-responsive gene regulatory systems, or switches, through the adoption of design rules previously elucidated for chRzs [8].

Initial ThRz Designs Demonstrate In vivo Limitations

Figure 20:
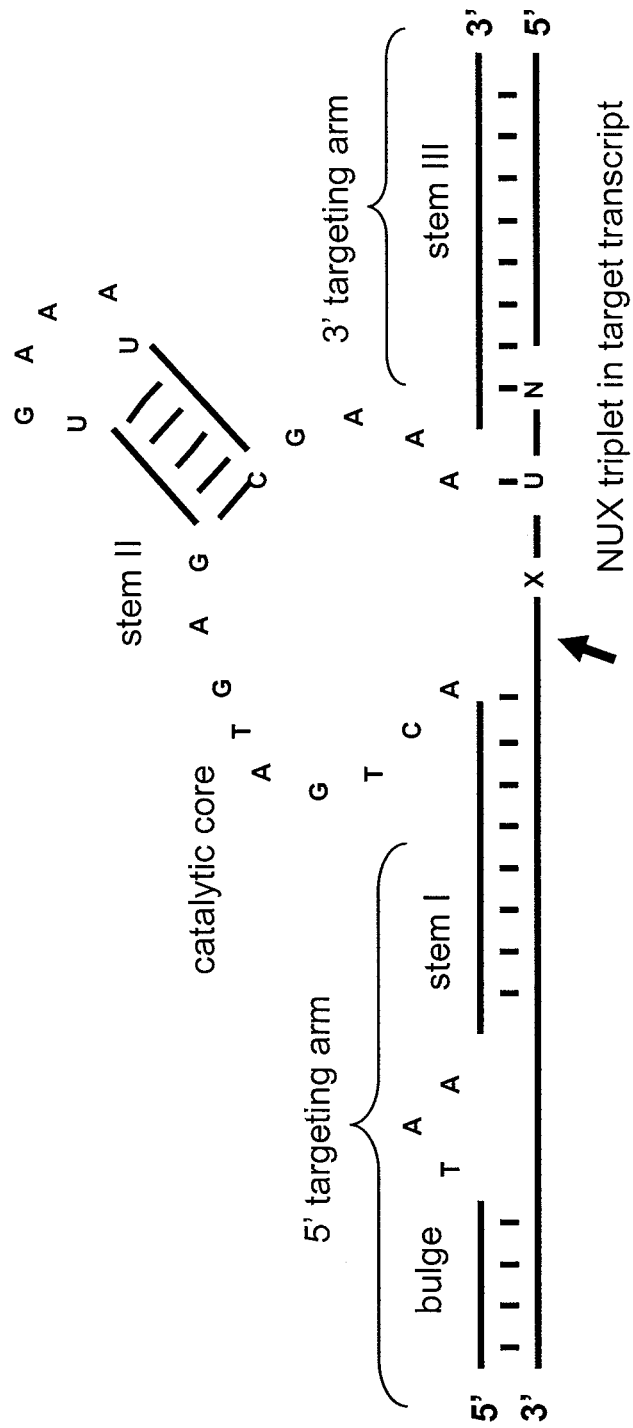
FIG. 20. The anatomy of a thRz with target transcript. The catalytic core is labeled in the figure. At low $Mg^{2+}$ concentrations, the bulge in stem I and stem loop II, interact to stabilize the active conformation. These interactions are found in natural chRzs and have been adapted for engineered thRzs.
Figure 21:
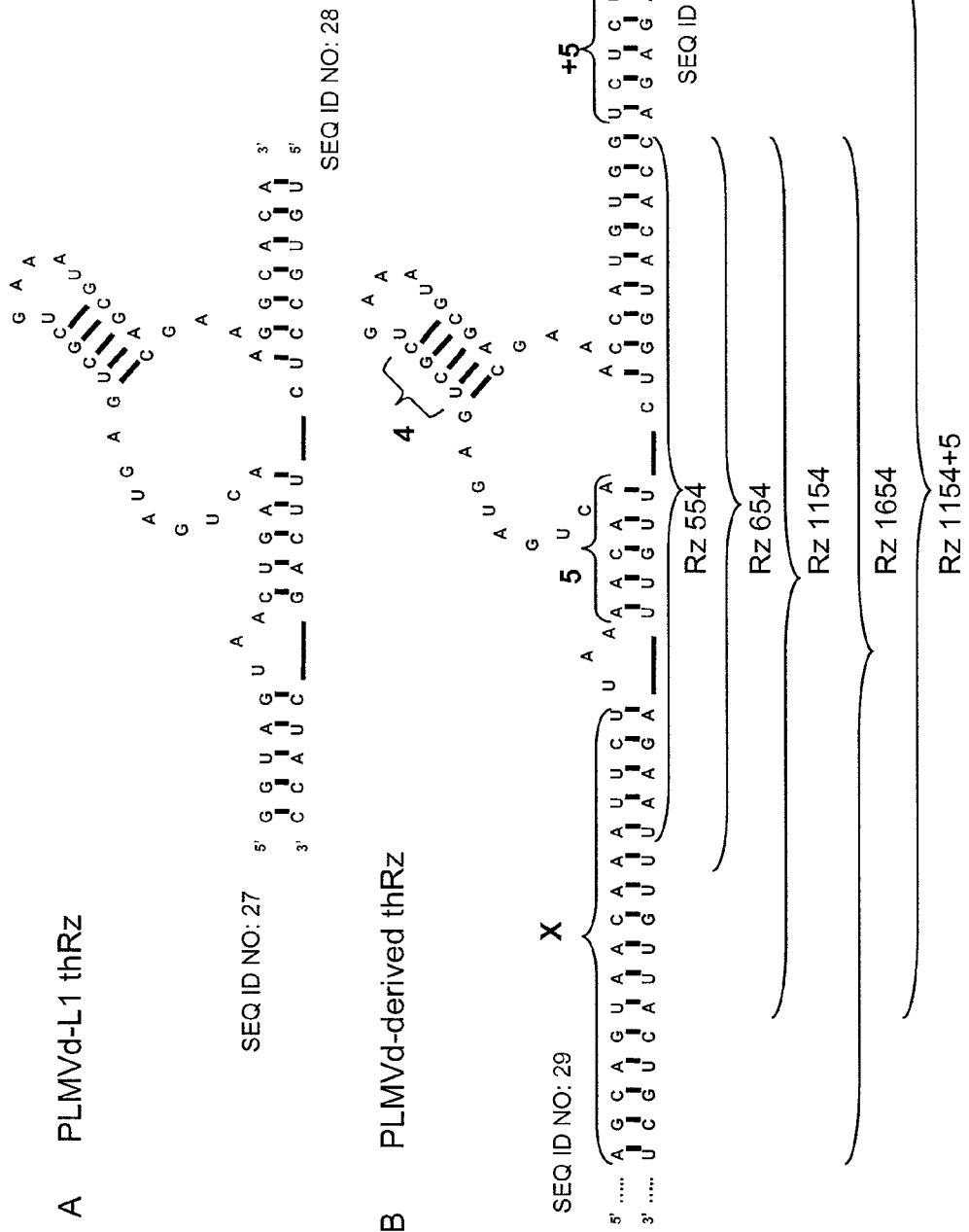
FIG. 21. Various thRz designs. A) Previous in vitro studies focused on incorporating the PLMVd-derived stem loops into thRz targeted a segment of HIV 1 mRNA, PLMVd-L1 thRz. B) By redesigning the targeting arms, we constructed a series of PLMVd-derived thRzs targeting a sequence in yEGFP.

ThRz designs were adapted from previous in vitro studies [23] to target a region in the yEGFP (yeast enhanced green fluorescent protein) transcript (FIGS. 20, 21). While we anticipate that the targeting arms will prove to be amenable to targeting a variety of sequences, developing thRzs that specifically target yEGFP is particularly useful for two reasons. First, targeting yEGFP allows us to directly monitor gene expression through fluorescence-based assays. Second, yEGFP is used to monitor various endogenous proteins via protein fusions. Thus, by developing a ribozyme that targets the expression of yEGFP it will be possible to regulate the expression of any mRNA tagged with the yEGFP target sequence without subsequent redesign of the ribozyme. The ribozyme designs observe the following composition rules. First, the catalytic core must be conserved to maintain activity (FIG. 20). Second, the target transcript must contain a NUX triplet, where N is any base, U is uracil, and X is any base but guanine. Finally, for in vivo activity, the catalytically active "Y" shaped conformation must be formed. To achieve this requirement at physiological $Mg^{2+}$ concentrations, the bulge in stem I and stem loop II, are designed to interact to stabilize the active conformation. These stem loop sequences are derived from those found in the peach latent mosaic viroid (PLMVd) ribozyme, a natural chRz. Adopting these loops requires careful design considerations when selecting a target sequence. The bulge region must maintain unpaired nucleotides requiring that the corresponding region of the target transcript does not have sequence complimentary. Additionally, canonical PLMVd ribozymes exhibit particular stem lengths between the stem I loop, the stem II loop, and the catalytic core. In stem I, 5 base pairs separate the bulge sequence from the catalytic core. In stem II, 4 base pairs separate the catalytic core and the stem loop sequence. Thus, canonical ribozymes will adopt the following nomenclature "X54" where X denotes the number of base pairs formed between the targeting arm sequence and the transcript 5' of the bulge (FIG. 21B).

Figure 22:
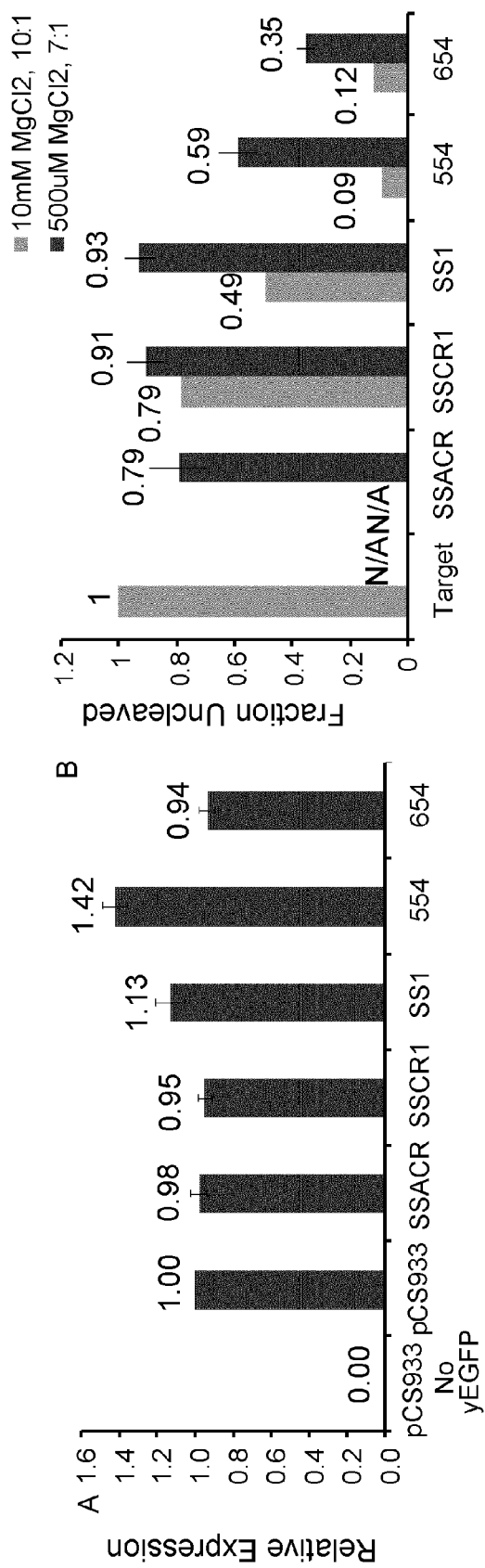
FIG. 22. Initial ribozyme designs. A) In vivo fluorescence levels of S. cerevisiae strains expressing yEGFP and various trans-ribozyme controls and constructs. pCS933 is the plasmid only control in both yEGFP (negative control) and no yEGFP (positive control). SSACR represents an off-target control in which the ribozyme core is maintained while the targeting arms are scrambled. SSCR1 represents an antisense control in which the targeting arms are maintained and the catalytic core is scrambled. SS1 represents a mRz control. B) In vitro cleavage assays after 1 hr at various $Mg^{2+}$ concentrations. Target represents the target transcript alone without the ribozymes added. All other samples are denoted by the ribozyme added to a reaction mix with target.

The initial thRz designs were characterized through in vitro cleavage assays. We modified our cleavage assay from previous examples to facilitate a more accurate correlation between in vitro results and in vivo activity. To develop this method we extended the length of the target transcript beyond the region that binds to the targeting arms. By including the peripheral regions, we are able to recapitulate the folding microenvironment of the full-length transcript for the region of interest. By targeting RNA that resembles in vivo transcripts, in vitro cleavage assays are expected to reflect in vivo cleavage efficiencies more accurately. In these assays both the thRz and 137 nts of the target gene, yEGFP, were transcribed separately in vitro and subsequently incubated together for different time periods to allow cleavage to proceed. Following incubation, cleaved and non-cleaved products were quantified through gel analysis. At 10 mM $MgCl_2$, the canonical ribozymes, 554 and 654, cleave ~90% of the target (FIG. 22B). The mRz, SS1, cleaves ~50% of target. At $Mg^{2+}$ concentrations comparable to physiological levels, the activity of SS1 is completely abolished whereas the canonical ribozymes maintain significant activity.

Figure 23:
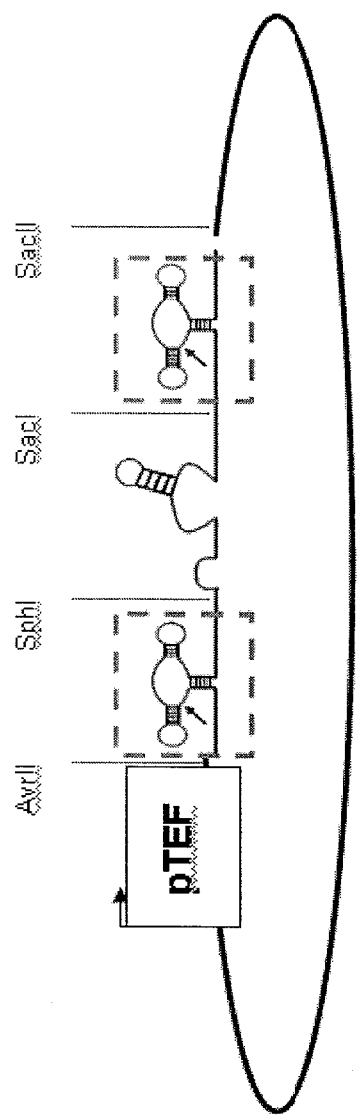
FIG. 23. Redesigned expression system. The chRz processing cassette was cloned into pCS933 through AvrII and SacII sites to construct pCS975. thRbz were subsequently cloned between SphI and SacI. This construct expresses the trans-ribozyme with flanking cis-ribozymes (dashed boxes) on either side of the trans-ribozyme transcript designed to trim transcript tails, removing the 5' cap and poly-A tail.

For this ribozyme to function optimally in vivo as well as in vitro, we made several alterations. While not wishing to be bound by any particular theory, we postulate that ribozymes may encounter interference in binding to their target transcripts through circularization of the ribonucleoprotein particle (RNP) in export from the nucleus. The ribozymes are expressed from a pol II promoter. During transcription, a modified nucleotide called the 5' cap is added to the 5' end of the mRNA transcribed from pol II promoters. As protein factors assemble onto the cap structure of the transcript, this complex binds to proteins assembled on the poly-A tail and circularizes the transcript. While not wishing to be bound by any particular theory, we postulate that in the RNP, ribozymes may be inhibited from binding to the target transcript by the topological constraints imposed by circularization of the transcript. Additionally, ribosome loading onto the transcript may occlude the targeting arms from binding the target transcript. Implementation of Improved Expression System Facilitates Correlation Between In Vitro and in vivo ThRz Cleavage Efficiency To test this hypothesis, we designed and cloned a flanking chRz cassette (into pCS933 through AvrII and SacII restriction sites) to construct pCS975 (FIG. 23). The cassette contains two chRz, previously shown to be highly efficient at self-cleaving in vivo [14, 18], separated by two unique restriction sites, SacI and SphI, for the rapid cloning of thRzs between these two elements.

The chRzs are expected to excise the thRz from the RNP through self-cleavage resulting in removal of the transcript tails containing the 5' cap and the poly-A tail. Removal of the 5' cap and poly-A tail will also prevent ribosomes from loading onto this regulatory RNA. By isolating the liberated transcript from promoter- and terminator-specific transcript tails, the chRz processing cassette will facilitate thRz portability across a range of expression systems.

Figure 24A:
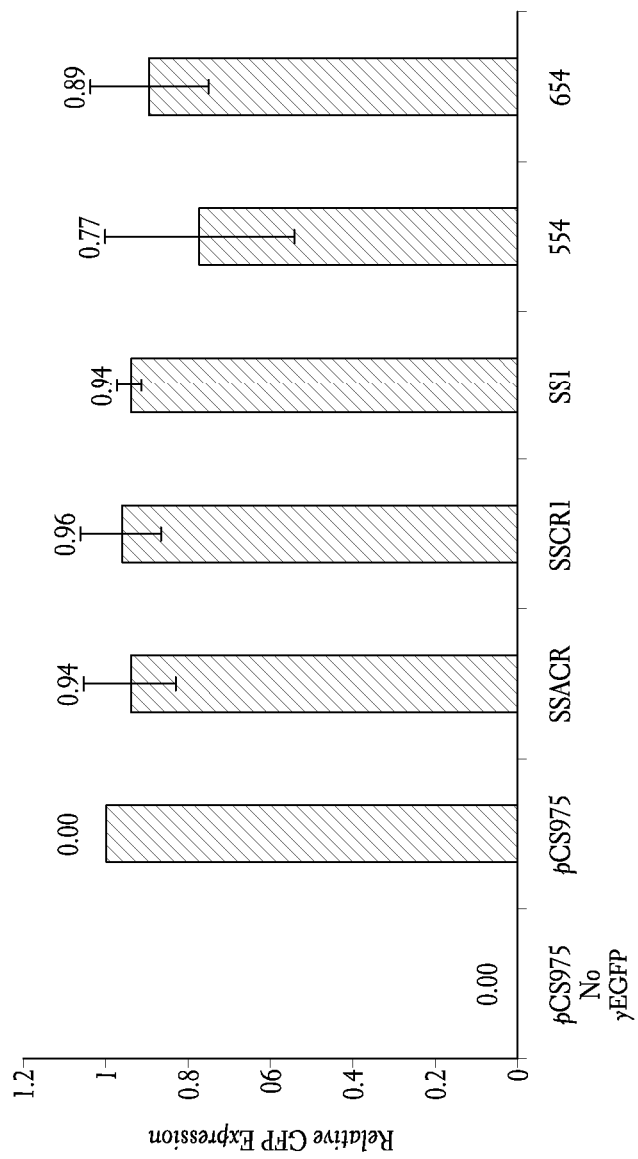
FIG. 24. Initial ribozyme designs with chRz processing cassette. A) In vivo fluorescence levels of S. cerevisiae strains expressing yEGFP and various trans-ribozyme controls and constructs. B) In vitro cleavage assays after 1 hr at various $Mg^{2+}$ concentrations.
Figure 24B:
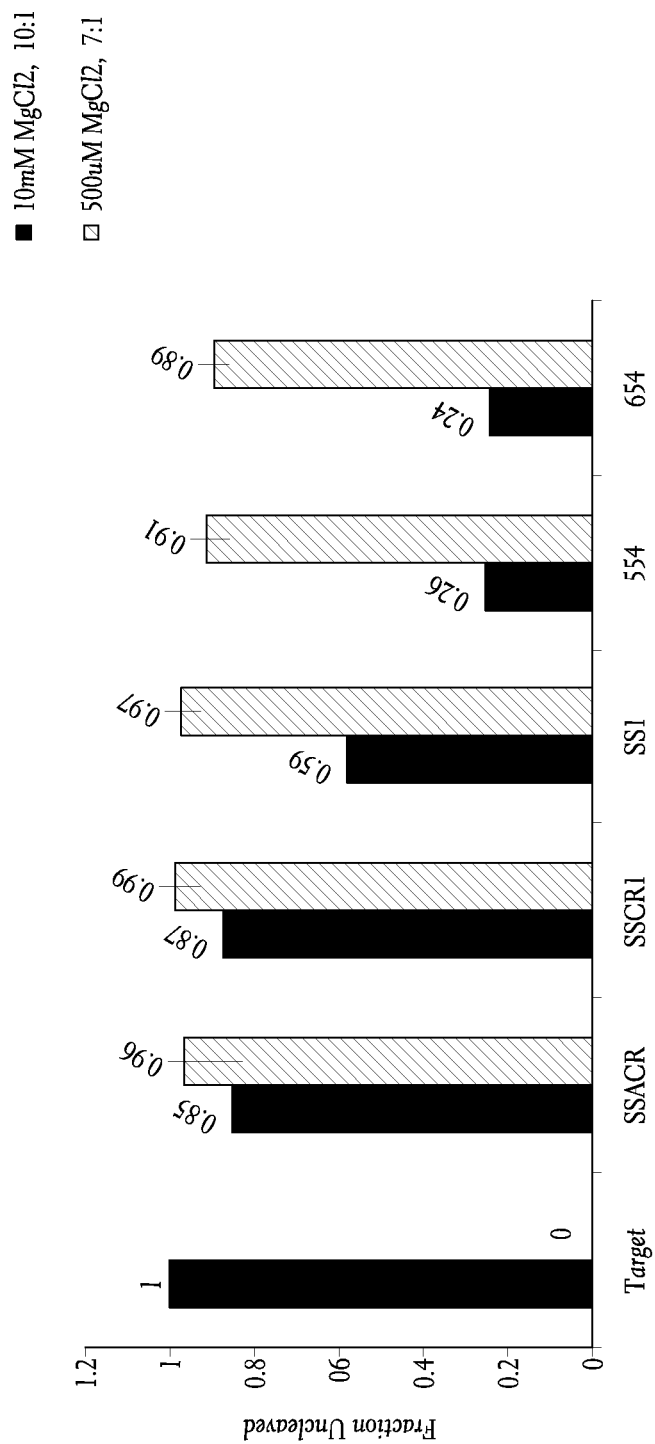

In vivo expression of the ribozymes from the redesigned plasmid system demonstrated 5-10% knockdown of gene expression (FIG. 24A). To separate the issues of catalytic efficiency of chRzs and thRzs and the efficiency of ribozyme targeting in vivo, the ribozymes were transcribed from pCS975 with promoter- and terminator-tails, as well as the chRz cassette. In vitro cleavage assays confirmed that the chRz cleaved with near perfect efficiency during transcription (data not shown). The resulting thRzs with chRz tails were incubated with target at various $Mg^{2+}$ concentrations. The thRzs flanked by the chRzs demonstrated lower overall activity while maintaining similar trends in cleavage efficiencies (FIG. 24B). At high $Mg^{2+}$ concentrations, cleavage efficiency dropped ~10% compared to the thRzs without the flanking chRz elements. At low $Mg^{2+}$, the thRzs with the chRz cassette cleave ~5-10% of that target which is 30-50% less efficient than the ribozymes without the chRz cassette. These data suggest that the chRz tails that remained following cis-cleavage interfere with thRz activity. Investigating the folded sequences in RNAstructure 4.3, a program for determining the expected secondary structure of RNA molecules, we hypothesized that the chRzs' tails interfered with thRz binding to the target by preferentially promoting formation of Watson-Crick base paring between the target sequence and the catalytic core. Competition of the core region and targeting arms for the target sequence is postulated to decrease the activity of the ribozymes. This effect may be magnified at low $Mg^{2+}$ concentrations, where proper folding of the ribozyme is not aided by increased levels of this ion. While the in vitro results confirmed the low activity of the thRzs, they also demonstrated that the thRz activity observed in vitro is translated to in vivo regulatory function. Thus, addition of the chRz cassette translates efficiencies demonstrated in vitro into in vivo results.

The in vitro results from the canonical thRz designs suggest that efficient cleavage requires high affinity of the targeting arms. At high $Mg^{2+}$ concentrations the loop interactions should have little effect on the rate of cleavage since sufficient $Mg^{2+}$ is present to stabilize the catalytically active conformation. Thus, observed differences between the mhRz's and the canonical thRzs' cleavage efficiencies at high $Mg^{2+}$ may be a result of differing binding affinities. Ribozyme binding affinity is expected to correlate with the length of the targeting arms. As length increase, affinity should increase. The targeting arms of SS1 are 4 nts and 5 nts shorter than 554 and 654, respectively. At 10 mM, this difference in affinity yields a 40% difference in cleavage efficiency between SS1 and the canonical ribozymes (FIG. 22B). At 500 µM, the difference in the length of the targeting arms is magnified. Ribozyme 654, which only differs from 554 by a single nucleotide in the targeting arms, is ~25% more efficient. These results strongly suggest that increasing the length of the targeting arms may significantly increase the observed ribozyme cleavage efficiency. Additionally, increasing the targeting arm length should favor proper ribozyme binding to the target by limiting the competition from the core region binding to the transcript as shown in RNAstructure 4.3.

Figure 25:
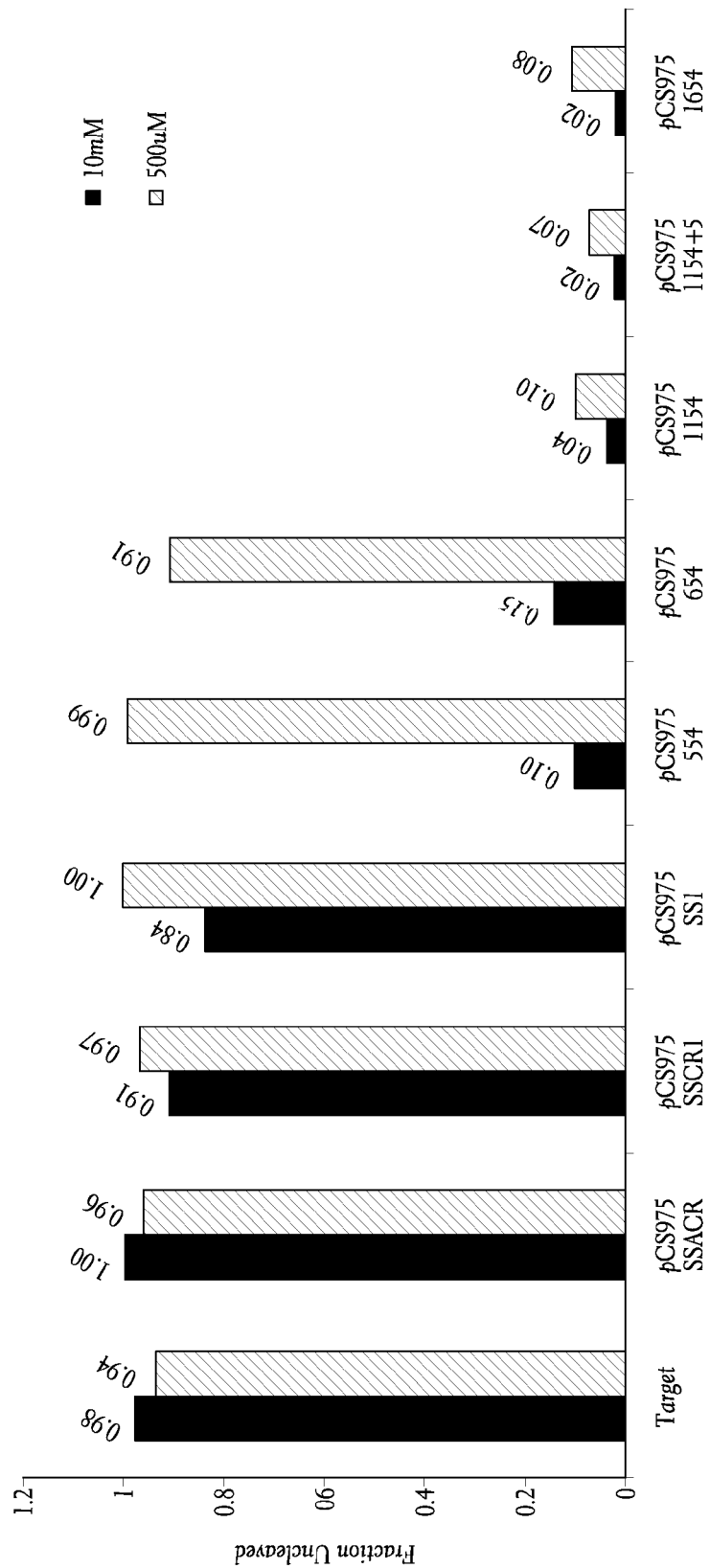
FIG. 25. Ribozymes with extended targeting arms in chRz processing cassette. In vitro cleavage assays after 1 hr at various Mg²⁺ concentrations. At intracellular Mg²⁺ concentrations after 1 hr, the thRz designs with extended arms have processed 80-90% more target than the previous thRzs.
Figure 27:
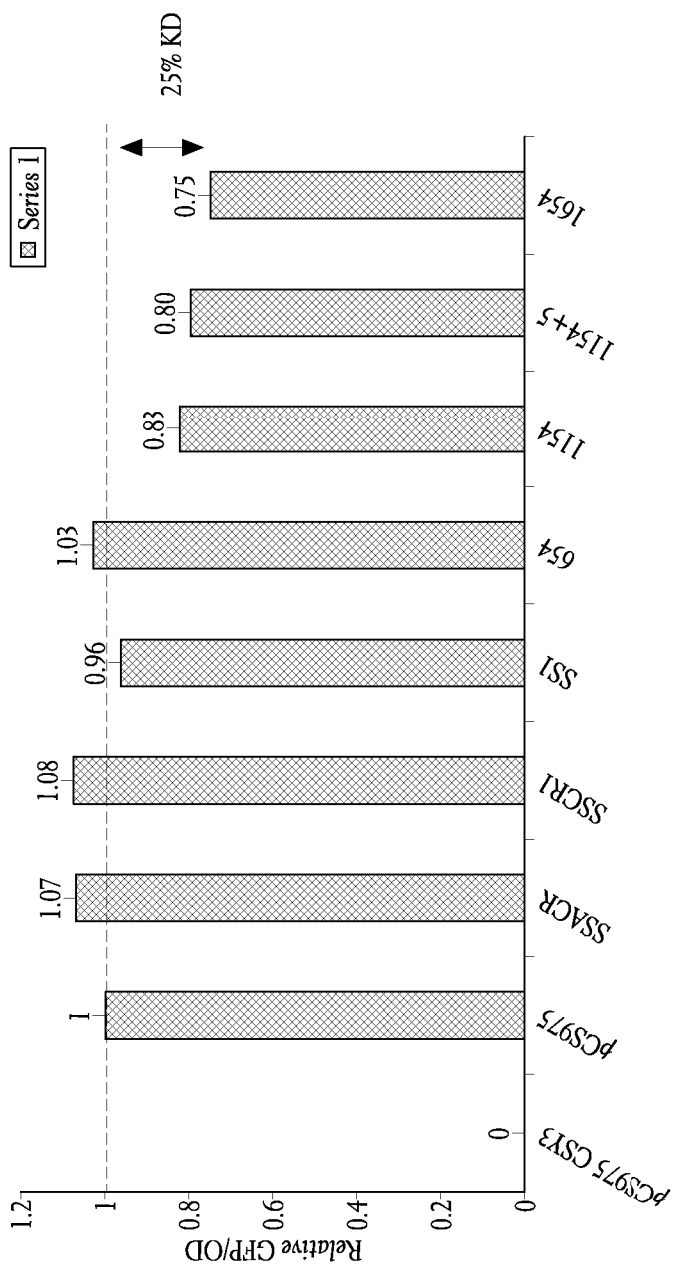
FIG. 27. Ribozymes with extended targeting arms in chRz processing cassette. In vivo fluorescence levels of *S. cerevisiae* strains expressing yEGFP and various trans-ribozyme controls and constructs. The thRz designs with extended arms (1154, 1154+5, 1654) exhibit greater inhibition of expression than the earlier designs.

Optimization of ThRz Targeting Arms Leads to Fast, Efficient Cleavage at Low $MgCl_2$ Concentrations To test this hypothesis, we constructed three new thRz designs with lengthened targeting arms (FIG. 21B). One design increased the length of the 5' arm by 5 nts, 1154. The second (1154+5) and third (1654) designs built on the first, adding 5 nts to the 3' and 5 nts to the 5' end, respectively. When folded in RNAstructure 4.3 with the 137 nt target sequence, the proper ribozyme-binding-to-target fold dominated the energy landscape as the minimum free energy (MFE) structure and was the only fold found in the 20 lowest free energy structures. When tested in vitro the canonical ribozymes with increased targeting arm length, show near 100% efficiency at 10 mM $Mg^{2+}$ and greater than 90% at physiological $Mg^{2+}$ concentrations (FIG. 25). The thRzs with increased targeting arm length exhibit greater cleavage efficiencies at low $Mg^{2+}$ than the previous canonical thRz design at high $Mg^{2+}$. Furthermore, in vivo assays indicate that the thRz designs with extended arms (1154, 1154+5, 1654) exhibit greater inhibition of reporter gene expression than the earlier designs (FIG. 27). These results indicate that the limiting step in the cleavage event is the intramolecular binding event between the thRz and target sequences. Formation of the catalytically active conformation appears to occur readily once the target is found as indicated by the difference between 654 and 1154. However, increased targeting arm lengths may also contribute to increased cleavage efficiency by increasing the stability of the active tertiary conformation, as well as the formation of the correct secondary structure.

Figure 26:
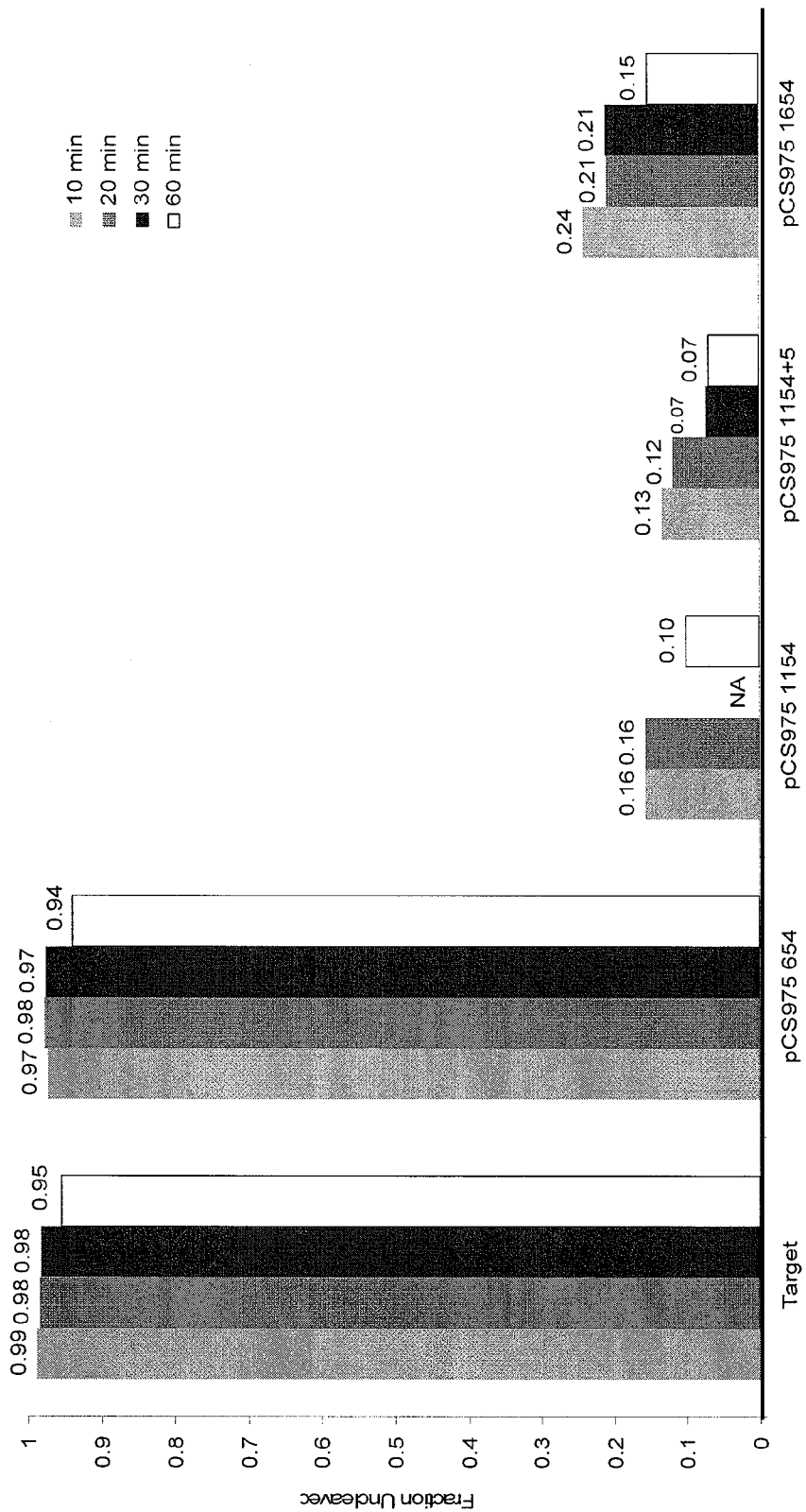
FIG. 26. In vitro time points for thRzs with extended targeting arms in chRz processing cassette are fast and highly efficient compared to previous designs. In vitro cleavage assays after 10, 20, 30, and 60 min at 37° C. and 500 µM MgCl₂.

In vitro cleavage assays demonstrate that lengthening the targeting arms facilitates rapid cleavage of the target transcript (FIG. 26). Within 10 minutes, all of the redesigned thRzs reach greater than 75% cleavage efficiency and one achieves 87%. For in vivo application it is important that the ribozymes act on biologically-relevant time scales (~several minutes). While previous in vitro studies have demonstrated fast and efficient thRz cleavage at higher $Mg^{2+}$ concentrations (1 mM), these results strongly suggest that full-kinetic evaluation will prove these designs to be faster and more efficient even at 500 µM. From initial indications, these may be the fastest thRzs ever reported and by far the most biologically-relevant.

Discussion

Through the rational design of trans-ribozyme targeting arms aided by computational models of RNA secondary structures, in vitro thRz activity at intracellular $Mg^{2+}$ concentrations was significantly increased. Additionally, by modifying our in vitro cleavage assay from previous examples, we have developed a more instructive in vitro assay for evaluating the potential of thRz designs to efficiently cleave target transcripts in vivo. Also, we have demonstrated that implementation of a chRz processing cassette that releases the thRz from the RNP facilitates improved correlation between in vitro and in vivo cleavage efficiencies. Finally, the in vitro thRz kinetics at intracellular $Mg^{2+}$ concentrations dictate that efficient cleavage reactions proceed on biologically-relevant timescales. With these results in hand, the subsequent in vivo application of the redesigned thRzs is extremely promising.

Development of this trans-ribozyme platform represents an opportunity to regulate the expression of target transcripts without the modification of existing, endogenous cellular components such as binding sites, promoters, repressors, and other cis-acting regulatory elements. By developing control elements that modulate gene expression without modification of the natural context of the target system, more powerful and less-invasive cellular programming strategies can be developed. Obviating the need to modify cis-regulatory elements will advance control strategies that can be more quickly transferred to multi-cellular organisms where such targeted genetic manipulation is often difficult.

The systems and methods described herein enable the development and characterization of thRz switches as control elements that regulate gene expression of target proteins in response to exogenous and endogenous ligands, using the rational coupling of aptamers and thRz domains. Such ligand-controlled riboregulators are termed ribozyme switches. The Smolke laboratory has recently developed and demonstrated a modular and extensible framework for engineering in vivo ligand-regulated ribozyme switches [8]. The described switch platforms contain three distinct functional domains: a ligand-binding or sensor domain, comprised of an aptamer sequence, a regulatory or actuator domain, comprised of a chRz sequence, and an information transmission domain, comprised of a sequence that transmits information between the sensor and the actuator domain (FIG. 2A). Small molecule-dependent regulation of gene expression was demonstrated on various heterologous genes. The platforms enabled the construction of riboswitches exhibiting up- and down-regulation of target expression levels (FIGS. 2B, C). The constructed cis-riboswitches represent a versatile platform for implementing ligand-controlled gene regulation in various applications including the programming of cellular control strategies.

ThRz switches offer a significant advantage over cis control strategies because they are able to target endogenous proteins without modifying the natural context of the target gene. This is advantageous because altering a cell's genome can often be difficult and result in off-target effects. The emergence of ligand-responsive control elements that act in trans significantly improve our ability to study natural metabolic and regulatory networks, as well as impose exogenous control and engineer new connections into these systems. By providing a modular interface between engineered gene networks and endogenous circuitry, these technologies significantly advance our ability to program cellular behavior.

Materials and Methods

Plasmid and Ribozyme Construction. The thRz expression construct, pCS933, was constructed using standard molecular biology techniques [31]. Briefly, two sets of TEF promoters and CYC1 terminators with intervening unique restriction sites were cloned into the plasmid backbone. A version of RFP, tdimer2, was cloned into the SalI and NotI restriction sites downstream of the second TEF promoter and served as a transformation control signal. The pCS933 engineered ribozyme constructs were generated by cloning the appropriate thRz constructs into the unique restriction sites, AvrII and SacII, downstream of the first TEF promoter. The thRz with flanking chRzs construct, pCS975, was constructed by cloning a cassette containing two chRzs with two intervening unique restriction sites, SphI and SacI, into AvrII and SalI. The pCS975 engineered ribozyme constructs were generated by cloning the appropriate thRz constructs into the SphI and SacI sites. All oligonucleotides were synthesized by Integrated DNA Technologies (Coralville, Iowa). Cloned plasmids were transformed into an electrocompetent *E. coli* strain, DH10B (Invitrogen, Carlsbad, Calif.), and all cloned ribozyme constructs were confirmed by sequencing (Laragen, Los Angeles, Calif.). Confirmed plasmid constructs were transformed into a *S. cerevisiae* strain W303 harboring a chromosomally-integrated GFP target construct (MATa his3-11,15 trpl-1 leu2-3 ura3-1 ade2-1, pTEF-yEGFP-PEST) using standard lithium acetate procedures [32].

In vitro cleavage assay. All ribozymes were PCR amplified from their plasmids along with the 23 nts upstream transcribed from the TEF promoter. A 137 nt region of the target yEGFP sequence was amplified by PCR. The forward primer in each of these amplification reactions harbors the T7 polymerase sequence at its 5' end such that a fusion between the desired sequence and the T7 promoter region is constructed. Sequences were transcribed using an Ampliscribe T7 kit (Epicentre Technologies, Madison, Wis.) and transcription reactions were purified through a NucAway column (Ambion, Foster City, Calif.), following manufacturer's instructions. The target yEGFP sequence was labeled with [$\alpha$-$^{32}$P]-GTP. Cleavage reactions were performed at 50 mM Tris-Cl pH 7.0, 100 mM NaCl, and the specified $MgCl_2$ concentration. The ratio of ribozyme to target was 10:1 and 7:1 as specified. Reactions were incubated at 95° C. for 5 min, cooled at room temp for 15 min, and placed for 1 hr at 37° C. Reactions were quenched with the addition of RNA loading buffer, heated at 65° C. for 5 min, and chilled at 4° C. for 5 min. Reaction products were separated on a denaturing PAGE gel and visualized on a phosphorimager (BioRAD).

Ribozyme Characterization. *S. cerevisiae* cells harboring the appropriate plasmids were grown in synthetic complete medium supplemented with an appropriate dropout solution and sugar [2% (wt/vol) dextrose] overnight at 30° C. Overnight cultures were back-diluted into fresh medium to an optical density at 600 nm ($OD_{600}$) of ~0.1 and grown at 30° C. Cells were grown to an $OD_{600}$ of 0.8-1.0 or for a period of ~6 hr before measuring GFP levels on a Cell Lab Quanta SC flow cytometer (Beckman Coulter, Fullerton, Calif.).

Fluorescence Quantification. Populations average fluorescence values were measured on a Quanta flow cytometer with the following settings: 488-nm laser line, 525-nm bandpass filter, and photomultiplier tube setting of 7.53 on FL1 (GFP) and 6.53 on FL3 (RFP). Fluorescence data were collected under low flow rates for ~20,000 viable cells. Cells bearing plasmids not expressing RFP were used to set a "RFP negative" gate. Viable cells bearing the plasmid were selected by gating for cells with fluorescence values on FL3 greater than the RFP negative gate. Fluorescence levels were determined from 10,000 counts in this selected population. Since the pTEF-yEGFP cassette is integrated into the chromosome, the FL1 values from entire population of viable, RFP positive cells were averaged to calculate the sample's GFP fluorescence value. All fluorescence data and mean±SD are reported from at least three independent experiments.

REFERENCES CITED IN EXAMPLE 4

1. Isaacs, F. J., D. J. Dwyer, and J. J. Collins, RNA synthetic biology. Nat Biotechnol, 2006. 24(5): p. 545-54.
2. Kobayashi, H., et al., Programmable cells: interfacing natural and engineered gene networks. Proc Natl Acad Sci USA, 2004. 101(22): p. 8414-9.
3. Aagaard, L. and J. J. Rossi, RNAi therapeutics: principles, prospects and challenges. Adv Drug Deliv Rev, 2007. 59(2-3): p. 75-86.
4. Grimm, D., et al., Fatality in mice due to oversaturation of cellular microRNA/short hairpin RNA pathways. Nature, 2006. 441(7092): p. 537-41.
5. Hanahan, D. and R. A. Weinberg, The hallmarks of cancer. Cell, 2000. 100(1): p. 57-70.
6. Qi, M. and E. A. Elion, MAP kinase pathways. J Cell Sci, 2005. 118(Pt 16): p. 3569-72.
7. McCormick, F., Signalling networks that cause cancer. Trends Cell Biol, 1999. 9(12): p. M53-6.
8. Win, M. N. and C. D. Smolke, A modular and extensible RNA-based gene-regulatory platform for engineering cellular function. Proc Natl Acad Sci USA, 2007.
9. Grassi, G., A. Forlino, and J. C. Marini, Cleavage of collagen RNA transcripts by hammerhead ribozymes in vitro is mutation-specific and shows competitive binding effects. Nucleic Acids Res, 1997. 25(17): p. 3451-8.
10. Scherr, M., et al., Specific hammerhead ribozyme-mediated cleavage of mutant N-ras mRNA in vitro and ex vivo. Oligoribonucleotides as therapeutic agents. J Biol Chem, 1997. 272(22): p. 14304-13.
11. Pan, W. H., et al., A self-processing ribozyme cassette: utility against human papillomavirus 11 E6/E7 mRNA and hepatitis B virus. Mol Ther, 2004. 9(4): p. 596-606.
12. Weinberg, M. S., et al., Effective anti-hepatitis B virus hammerhead ribozymes derived from multimeric precursors. Oligonucleotides, 2007. 17(1): p. 104-12.
13. Long, D. M. and O. C. Uhlenbeck, Self-cleaving catalytic RNA. Faseb J, 1993. 7(1): p. 25-30.
14. De la Pena, M., S. Gago, and R. Flores, Peripheral regions of natural hammerhead ribozymes greatly increase their self-cleavage activity. Embo J, 2003. 22(20): p. 5561-70.
15. Pley, H. W., K. M. Flaherty, and D. B. McKay, Three-dimensional structure of a hammerhead ribozyme. Nature, 1994. 372(6501): p. 68-74.
16. Hammann, C., D. G. Norman, and D. M Lilley, Dissection of the ion-induced folding of the hammerhead ribozyme using $^{19}$F NMR. Proc Natl Acad Sci USA, 2001. 98(10): p. 5503-8.
17. Blount, K. F. and O. C. Uhlenbeck, The structure-function dilemma of the hammerhead ribozyme. Annu Rev Biophys Biomol Struct, 2005. 34: p. 415-40.
18. Khvorova, A., et al., Sequence elements outside the hammerhead ribozyme catalytic core enable intracellular activity. Nat Struct Biol, 2003. 10(9): p. 708-12.
19. Salehi-Ashtiani, K. and J. W. Szostak, In vitro evolution suggests multiple origins for the hammerhead ribozyme. Nature, 2001. 414(6859): p. 82-4.
20. Canny, M. D., et al., Fast cleavage kinetics of a natural hammerhead ribozyme. J Am Chem Soc, 2004. 126(35): p. 10848-9.
21. Penedo, J. C., et al., Folding of the natural hammerhead ribozyme is enhanced by interaction of auxiliary elements. Rna, 2004. 10(5): p. 880-8.
22. Saksmerprome, V., et al., Artificial tertiary motifs stabilize trans-cleaving hammerhead ribozymes under conditions of submillimolar divalent ions and high temperatures. Rna, 2004. 10(12): p. 1916-24.
23. Weinberg, M. S, and J. J. Rossi, Comparative single-turnover kinetic analyses of trans-cleaving hammerhead ribozymes with naturally derived non-conserved sequence motifs. FEBS Lett, 2005. 579(7): p. 1619-24.
24. Burke, D. H. and S. T. Greathouse, Low-magnesium, trans-cleavage activity by type III, tertiary stabilized hammerhead ribozymes with stem 1 discontinuities. BMC Biochem, 2005. 6: p. 14.
25. Elion, E. A., The Step 5p scaffold. J Cell Sci, 2001. 114(Pt 22): p. 3967-78.
26. Park, S. H., A. Zarrinpar, and W. A. Lim, Rewiring MAP kinase pathways using alternative scaffold assembly mechanisms. Science, 2003. 299(5609): p. 1061-4.
27. Liu, L., et al., Sorafenib blocks the RAF/MEK/ERK pathway, inhibits tumor angiogenesis, and induces tumor cell apoptosis in hepatocellular carcinoma model PLC/PRF/5. Cancer Res, 2006. 66(24): p. 11851-8.
28. Shapiro, P., Discovering new MAP kinase inhibitors. Chem Biol, 2006. 13(8): p. 807-9.
29. Dominguez, C., D. A. Powers, and N. Tamayo, p38 MAP kinase inhibitors: many are made, but few are chosen. Curr Opin Drug Discov Devel, 2005. 8(4): p. 421-30.
30. Dambach, D. M., Potential adverse effects associated with inhibition of p38alpha/beta MAP kinases. Curr Top Med Chem, 2005. 5(10): p. 929-39.
31. Sambrook J, R. D., Molecular Cloning: A Laboratory Manual 3rd Ed. ed. 2001, Cold Spring Harbor, N.Y.: Cold Spring Harbor Lab Press.
32. Guthrie, C. and G. Fink, Guide to Yeast Genetics and Molecular and Cell Biology, ed. J. N. Abelson and M. I. Simon. Vol. 194. 2004, London: Elsevier, Inc.

EXAMPLE 5

Design Parameters for Allosteric Trans-Hammerhead Ribozyme (ThRz) Switch Platforms Catalytic Core The catalytic core of the hammerhead ribozyme consists of twelve conserved nucleotides. From stem I, the sequence follows from stem 1 to 5'-CTAGATGAG (SEQ ID NO: 31)-stem II sequence-CGAA-3' ending at stem III. The guanine located 5' of the intervening stem II sequence forms a Watson-Crick base pair (bp) with the cytosine that is 3' of the intervening stem II sequence. This pairing isolates the catalytic core from the stem II sequence.

```
Catalytic Core:
5'-CTAGATGAG(SEQ ID NO: 31)-stem II sequence-CGAA-3'
```

Target Sequence and Targeting Arms

The target sequence can be of any length, however, the region of interest for design purposes is at least 26 by long. (Note: Where target and targeting arm lengths are defined these values represent a minimum. The length of the sequence will varying based on the GC content of the sequence surround the NUX triplet. Additionally, it is important to engineer the targeting arms to favor proper target-to-ribozyme binding.) Specifically, there are at least 15 bases 3' of the NUX triplet and at least 7 bases that are 5' of it. These bases of interest shall be specified T1 through T26, where T denotes the base specified in the target. Target sequences must contain a NUX triplet at T8-T10, where N represents any base, U represents uracil, and X stands for any base but guanine. For greatest efficiency, choose X to be cytosine and N to be guanine, GUC. Thus the sequence is specified so far as 5'-$N_7$-GUC—$N_{15}$-3'. Since the targeting arms identify targets through Watson-Crick base pairing, the NUX triplet specifies bases in the targeting arm. The 3' targeting arm of the ribozyme is immediately 3' of the ribozyme catalytic core and specified by at least 9 bases. These bases must be complementary to the T1-T9 such that the 3' targeting arm is specified as: 5'-AC-$N_7$-3'. The 5' arm is designed to by with T11-T26, but has additional bases denoted as bulge bases, B. Such that the 5' targeting arm is as follows: 5'-$N_{11}$—BBB—$N_5$-3'. Typically, BBB will be UAA a bulge sequence derived from the naturally occurring ribozyme in the Peach Latent Mosaic Viroid. (Note: if stem loops are derived from alternative natural ribozymes it will be necessary to alter the design rules for the targeting arm and target sequence.) The bulge is critical for interaction of stem I and stem II, which stabilizes the catalytically active conformation under physiological magnesium concentrations. This will be discussed more thoroughly as the design of stem II is described. The targeting arms comprise the ribozyme's contribution to the stem I and stem III region. Additionally, since it is important for the target transcript not to pair with the bulge bases, the bases T16-T18 must be specified as K'K'L' where K' is any base but uracil and L' is any base but adenine. Note that the cytosine at T10 is not base-paired and this is essential for catalytic activity.

```
Target Sequence:
5'-N₇-GUC-N₅-K'K'L'-N₈-3'

Target Arms:
5'-N₁₁-UAA-N₅-Catalytic core and stem II-AC N₇-3'
```

Stem I

Stem I is comprised of the target transcript based paired to ribozyme targeting arm. This base pairing leads to a helical three-dimensional structure and often stem I is called helix I. There are at least 16 by in this helix and 3 free bases.

Stem III

Stem III is comprised of the target transcript based paired to ribozyme targeting arm. This base pairing leads to a helical three-dimensional structure and often stem III is called helix III. This helix is at least 9 by long.

Stem II

For allosteric control, the proper design of stem II is essential. Additionally, the correct specification of the bulges, helical regions, and aptamer domains is critical for in vivo activity and efficient ribozyme cleavage.

Helical Region and Bulge

The helical region proceeds directly 5' and 3' from the catalytic core. The catalytic core ends with base pairing between the 5'G and the 3'C. From this base paired closure of the core, the stem continues with 4 additional bp. This value is flexible depending on the bulge sequences chosen. 4 is optimal for the bulges derived from the Peach Latent Mosaic Viroid (PLMVd) ribozyme. The bulge in stem II is required for in vivo activity. The interaction between the bulge bases in stem I and stem II brings the stems into closer proximity of each other and stabilizes the catalytically active ribozyme conformation at low magnesium concentration, such as persists under in vivo conditions. The bulge consists of 6 bases, 3 on each side of the helix. From the 5' helical region the sequence for the PLMVd bulge is: UAG and from the 3' helical region: UAA.

Stem II: 5' Catalytic Core-$N_4$-UAG-Aptamer Region-UAA-$N_4$-Catalytic Core-3'

Aptamer Region

Following the bulge, another helical region follows. This helical region is designed to switch between two conformations which are dependent upon ligand binding at the aptamer domain. The design of this region is critical for the development of ligand-regulated switches which standardize and amplify the conformational change associated with the ligand binding event by pairing aptamer and expression platform domains through a linker platform (information transmission domain). In these engineered switches, conformational changes associated with ligand binding to the aptamer domain are transduced to a common larger-scale conformational rearrangement in the ribozyme catalytic core, thereby regulating its conversion between an active and inactive state. Two types of information transmission domains are used for connecting the aptamer domain to stem II; communication modules act through helix slipping mechanism and strand displacement linkers act through strand displacement.

Communication Module

When the communication module is the linker chosen to connect the aptamer to stem II, the precise sequence that yields switching behavior must be chosen uniquely for each aptamer through iterative design choices. Ideally, binding at the aptamer changes base pairing through the communication module, which in turn induces a base-pair "slip" through the stem II region into the catalytic core. This slipping mechanism regulates the conversion between the active and inactive conformations.

Strand Displacement

When strand displacement is the method of choice for connecting the aptamer to stem II, this displacement can be rationally designed to accompany an array of aptamers. Strand displacement induces a larger scale change in the stem II region upon ligand binding. This larger scale conformation change makes the mechanism of transducing ligand binding into conformation changes in the ribozyme more robust.

Aptamers

A wide array of aptamers can be coupled to the stem II region via various linkers. Input ligands include small molecules, proteins, and oligonucleotides. Theoretically, an aptamer can be developed to nearly molecule through SELEX. This makes the trans-ribozyme switch platforms extremely flexible in their range of input ligands.

Stem II: 5'-Helix II-Bulge5'-linker5'-Aptamer sequence-linker 3'-Bulge3'-Helix 11-3'

Steric Hindrance Considerations

Since trans-ribozyme switch platforms act through a bimolecular reaction it is important to ensure that the tails of the transcribed ribozyme do not occlude the targeting arms. Additionally, transcription tails should not possess significant secondary structures that impede formation of the catalytically active conformation of the ribozyme. To eliminate, hairpins and other secondary structures from interfering with target binding or core formation, cis-acting ribozymes can be placed 3' and 5' of the trans-riboswitch platform to trim the transcript. This will yield the trans-ribozyme switch platform with smaller, precise tails. Additionally, the cis-ribozyme cassette isolates the trans-ribozyme from the specific sequences of the promoter and terminator. Thus, the module becomes more predictably portable across a range of expression systems. Note that it is necessary to design sequence elements outside the trans-riboswitch platform to ensure the platform is able to efficiently cleave target.

Elements Outside of Platform

With Transcript Tails:

5'-Transcript tail-trans-ribozyme switch platform-Transcript tail-3'

With Flanking Cis-Ribozymes:

Before Cleavage of Cis-Ribozymes. 5'-Transcript tail-5' cis-ribozyme-trans-ribozyme switch platform-3' cis-ribozyme-Transcript tail-3'

After Cleavage of Cis-Ribozymes. 5'-Several bases-trans-ribozyme switch platform-a few bases-3' (The dashes above generally represent restriction enzyme sites.)

Final Trans-Ribozyme Switch Platform

5'-$N_{11}$-UAA-$N_5$-CTAGATGAG (SEQ ID NO: 31)-$N_4$-UAG-linker

5'-Aptamer-linker 3'-UAA-$N_4$-CGAA-AC $N_7$-3'

Final Target Sequence Requirements

5'-$N_7$-GUC-$N_5$-K'K'L'-$N_8$-3'

---

The invention claimed is:

1. An aptamer-regulated ribozyme for cleaving a target nucleic acid, comprising
  (a) a trans-acting hammerhead ribozyme comprising catalytic core, a 5' targeting arm which hybridizes to a 3' sequence of said target nucleic acid, a 3' targeting arm which hybridizes to a 5' sequence of said target nucleic acid, and a stem duplex region extending from said catalytic core with a single-stranded loop region opposite to said catalytic core;
  (b) an information transmission domain (ITD) having a first end and a second end, which information transmission domain is directly coupled to said loop through said first end; and
  (c) an aptamer coupled to said information transmission domain through said second end, said aptamer binds to a ligand,
  wherein said ITD is between the trans-acting hammerhead ribozyme and the aptamer, and comprises:
    (i) a general transmission region,
    (ii) a switching strand that hybridizes with the general transmission region in the absence of the ligand, and,
    (iii) a competing strand that hybridizes with the general transmission region in the presence of the ligand,
    wherein the switching strand and the competing strand compete to bind to the general transmission region through hybridization interactions,
  wherein binding of said ligand to said aptamer favors a conformation change in the aptamer,
  wherein said conformation change causes the ITD to favor the binding of the general transmission region to said competing strand via a strand-displacement mechanism; and,
  wherein hybridization between the general transmission region and the competing strand causes, via the interaction of said information transmission domain with one or more of said loop, said stem or said catalytic core, said aptamer-regulated ribozyme to cleave the target nucleic acid at a rate dependent upon the presence or absence of said ligand.

2. The aptamer-regulated ribozyme of claim 1, wherein binding of said ligand to said aptamer alters the size of said loop, thereby altering the ability of said aptamer-regulated ribozyme to cleave said target nucleic acid in a manner dependent on said ligand.

3. The aptamer-regulated ribozyme of claim 1, wherein binding of said ligand to said aptamer alters the size of said catalytic core, thereby altering the ability of said aptamer-regulated ribozyme to cleave said target nucleic acid in a manner dependent on said ligand.

4. The aptamer-regulated ribozyme of claim 1, wherein the ligand is a small molecule having a molecular weight less than 2500 amu and/or is cell permeable.

5. The aptamer-regulated ribozyme of claim 1, wherein the ligand is a metal ion.

6. The aptamer-regulated ribozyme of claim 1, wherein the ligand is a natural product.

7. The aptamer-regulated ribozyme of claim 6, wherein the ligand is a signal transduction second messenger molecule.

8. The aptamer-regulated ribozyme of claim 6, wherein the ligand is a post-translationally modified protein.

9. The aptamer-regulated ribozyme of claim 1, wherein the ligand is selected from the group consisting of polypeptides, peptides, nucleic acids, carbohydrates, fatty acids and lipids, a non-peptide hormone and metabolic precursors or products thereof.

10. The aptamer-regulated ribozyme of claim 1, wherein the ligand is selected from the group consisting of enzyme co-factors, enzyme substrates and products of enzyme-mediated reactions.

11. An expression construct comprising
  (i) a coding sequence which, when transcribed to RNA, produces said aptamer-regulated ribozyme of claim 1, and
  (ii) one or more transcriptional regulatory sequences that regulate transcription of said RNA in a cell containing said expression construct.

12. A method for rendering expression of a target gene in a cell dependent on the presence or absence of a ligand, comprising introducing into the cell a trans-acting hammerhead ribozyme comprising:
  (a) a catalytic core, a 5' targeting arm which hybridizes to a 3' sequence of an mRNA transcribed from said target gene, a 3' targeting arm which hybridizes to a 5' sequence of said mRNA transcribed from said target gene, and a stem duplex region extending from said catalytic core with a single-stranded loop region opposite to said catalytic core;
  (b) an information transmission domain (ITD) having a first end and a second end, which information transmission domain is directly coupled to said loop through said first end; and
  (c) an aptamer coupled to said information transmission domain through said second end, said aptamer binds to a ligand;
  wherein said ITD is between the trans-acting hammerhead ribozyme and the aptamer, and comprises:
    (i) a general transmission region,
    (ii) a switching strand that hybridizes with the general transmission region in the absence of the ligand, and,
    (iii) a competing strand that hybridizes with the general transmission region in the presence of the ligand,
    wherein the switching strand and the competing strand compete to bind to the general transmission region through hybridization interactions,
  wherein binding of said ligand to said aptamer favors a conformation change in the aptamer,
  wherein said conformation change causes the ITD to favor the binding of the general transmission region to said competing strand via a strand-displacement mechanism; and,
  wherein hybridization between the general transmission region and the competing strand causes, via the interaction of said information transmission domain with one or more of said loop, said stem or said catalytic core, said trans-acting hammerhead ribozyme to cleave the mRNA transcribed from said target gene at a rate dependent upon the presence or absence of said ligand so as to render expression of the target gene in the cell dependent on said ligand.

13. The method of claim 12, wherein the ligand is produced by said cell.

14. The method of claim 12, wherein the ligand is a cell permeable agent that is contacted with said cell.

15. A method of determining the amount of an analyte in a cell which expresses a reporter gene, comprising:
   (i) introducing into the cell a trans-acting hammerhead ribozyme comprising
      (a) a catalytic core, a 5' targeting arm which hybridizes to a 3' sequence of an mRNA transcribed from said reporter gene, a 3' targeting arm which hybridizes to a 5' sequence of said mRNA transcribed from said reporter gene, and a stem duplex region extending from said catalytic core with a single-stranded loop region opposite to said catalytic core;
      (b) an information transmission domain (ITD) having a first end and a second end, which information transmission domain is directly coupled to said loop through said first end; and
      (c) an aptamer coupled to said information transmission domain through said second end, said aptamer selectively binds to said analyte;
   wherein said ITD is between the trans-acting hammerhead ribozyme and the aptamer, and comprises:
      (i) a general transmission region,
      (ii) a switching strand that hybridizes with the general transmission region in the absence of the ligand, and,
      (iii) a competing strand that hybridizes with the general transmission region in the presence of the ligand,
   wherein the switching strand and the competing strand compete to bind to the general transmission region through hybridization interactions,
   wherein binding of said analyte to said aptamer favors a conformation change in the aptamer,
   wherein said conformation change causes the ITD to favor the binding of the general transmission region to said competing strand via a strand-displacement mechanism; and,
   wherein hybridization between the general transmission region and the competing strand causes, via the interaction of said information transmission domain with one or more of said loop, said stem or said catalytic core, said trans-acting hammerhead ribozyme to cleave the mRNA transcribed from said reporter gene at a rate dependent upon the presence or absence of said analyte;
   (ii) measuring the amount of expression of said reporter gene; and
   (iii) correlating the amount of expression of said reporter gene with the amount of analyte, thereby determining the amount of the analyte in the cell.

16. A method for causing phenotypic regulation of cell growth, differentiation or viability in cells of a patient, comprising introducing into cells in said a patient an aptamer-regulated ribozyme of claim 1, where said aptamer binds to a ligand, the concentration of which is dependent on cellular phenotype, wherein binding of said ligand to said aptamer induces a conformational change between active and inactive forms of said trans-acting hammerhead ribozyme, and said active form of said trans-acting hammerhead ribozyme inhibits expression of said target gene to alter the regulation of cell growth, differentiation or viability in said cells.

17. A pharmaceutical preparation comprising an aptamer-regulated ribozyme of claim 1, or an expression construct which, when transcribed, produces an RNA including said aptamer-regulated ribozyme, and a pharmaceutically acceptable carrier suitable for use administration to a human or nonhuman patient.

* * * * *